United States Patent
Garrison et al.

(10) Patent No.: US 9,561,345 B2
(45) Date of Patent: Feb. 7, 2017

(54) METHODS AND SYSTEMS FOR TREATMENT OF ACUTE ISCHEMIC STROKE

(71) Applicant: Silk Road Medical, Inc., Sunnyvale, CA (US)

(72) Inventors: Michi E. Garrison, Sunnyvale, CA (US); Tony M. Chou, Sunnyvale, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 0 days.

(21) Appl. No.: 14/576,953

(22) Filed: Dec. 19, 2014

(65) Prior Publication Data

US 2015/0173782 A1 Jun. 25, 2015

Related U.S. Application Data

(60) Provisional application No. 62/083,128, filed on Nov. 21, 2014, provisional application No. 62/075,169,
(Continued)

(51) Int. Cl.
*A61M 25/01* (2006.01)
*A61B 17/22* (2006.01)
(Continued)

(52) U.S. Cl.
CPC .............. *A61M 25/01* (2013.01); *A61B 17/22* (2013.01); *A61B 17/320758* (2013.01);
(Continued)

(58) Field of Classification Search
CPC ..................... A61M 25/0053; A61M 25/0054; A61M 2025/0078; A61M 2025/0175
See application file for complete search history.

(56) References Cited

U.S. PATENT DOCUMENTS 3,631,848 A  1/1972 Muller
4,771,777 A  9/1988 Horzewski et al.
(Continued)

FOREIGN PATENT DOCUMENTS

DE 102006039236 A1 2/2008
EP 0427429 A2 5/1991
(Continued)

OTHER PUBLICATIONS

Adami, M.D., et al., (2002) "Use of the Parodi Anti-Embolism System in Carotid Stenting: Italian Trial Results" J Endovasc Ther 9:147-154.
(Continued)

*Primary Examiner* — Katrina Stransky
(74) *Attorney, Agent, or Firm* — Mintz Levin Cohn Ferris Glovsky and Popeo, P.C.

(57) ABSTRACT

A system of devices for treating an artery includes an arterial access sheath adapted to introduce an interventional catheter into an artery and an elongated dilator positionable within the internal lumen of the sheath body. The system also includes a catheter formed of an elongated catheter body sized and shaped to be introduced via a carotid artery access site into a common carotid artery through the internal lumen of the arterial access sheath. The catheter has an overall length and a distal most section length such that the distal most section can be positioned in an intracranial artery and at least a portion of the proximal most section is positioned in the common carotid artery during use.

22 Claims, 36 Drawing Sheets

Related U.S. Application Data filed on Nov. 4, 2014, provisional application No. 62/075,101, filed on Nov. 4, 2014, provisional application No. 62/046,112, filed on Sep. 4, 2014, provisional application No. 62/029,799, filed on Jul. 28, 2014, provisional application No. 61/919,945, filed on Dec. 23, 2013.

(51) Int. Cl.
| | | |
|---|---|---|
| *A61M 29/00* | (2006.01) | |
| *A61M 25/06* | (2006.01) | |
| *A61M 25/00* | (2006.01) | |
| *A61B 17/3207* | (2006.01) | |
| *A61M 25/10* | (2013.01) | |
| *A61B 17/34* | (2006.01) | |
| *A61B 17/00* | (2006.01) | |
| *A61B 17/221* | (2006.01) | |

(52) U.S. Cl.
CPC .... *A61M 25/0023* (2013.01); *A61M 25/0043* (2013.01); *A61M 25/0054* (2013.01); *A61M 25/0662* (2013.01); *A61M 29/00* (2013.01); *A61B 17/3417* (2013.01); *A61B 2017/00867* (2013.01); *A61B 2017/00991* (2013.01); *A61B 2017/2212* (2013.01); *A61B 2017/2215* (2013.01); *A61B 2017/2217* (2013.01); *A61B 2017/22038* (2013.01); *A61B 2017/22039* (2013.01); *A61B 2017/22054* (2013.01); *A61B 2017/22072* (2013.01); *A61B 2017/22079* (2013.01); *A61B 2017/22084* (2013.01); *A61B 2017/22094* (2013.01); *A61B 2017/320775* (2013.01); *A61B 2017/3484* (2013.01); *A61B 2017/3486* (2013.01); *A61B 2090/062* (2016.02); *A61M 25/007* (2013.01); *A61M 25/0041* (2013.01); *A61M 25/0068* (2013.01); *A61M 2025/0004* (2013.01); *A61M 2025/0037* (2013.01); *A61M 2025/0042* (2013.01); *A61M 2025/0175* (2013.01); *A61M 2025/0681* (2013.01); *A61M 2025/1052* (2013.01); *A61M 2210/12* (2013.01)

(56) References Cited

U.S. PATENT DOCUMENTS

| | | |
|---|---|---|
| 4,840,690 A | 6/1989 | Melinyshyn et al. |
| 4,865,581 A | 9/1989 | Lundquist et al. |
| 4,921,478 A | 5/1990 | Solano et al. |
| 4,921,479 A | 5/1990 | Grayzel |
| 4,946,440 A | 8/1990 | Hall |
| 5,135,484 A | 8/1992 | Wright |
| 5,250,060 A | 10/1993 | Carbo et al. |
| 5,312,356 A | 5/1994 | Engelson et al. |
| RE34,633 E | 6/1994 | Sos et al. |
| 5,324,262 A | 6/1994 | Fischell et al. |
| 5,328,471 A | 7/1994 | Slepian |
| 5,338,300 A | 8/1994 | Cox |
| 5,380,284 A | 1/1995 | Don Michael |
| 5,385,562 A | 1/1995 | Adams et al. |
| 5,429,605 A | 7/1995 | Richling: Bernd et al. |
| 5,437,632 A | 8/1995 | Engelson |
| 5,443,454 A | 8/1995 | Tanabe et al. |
| 5,454,795 A | 10/1995 | Samson |
| 5,476,450 A | 12/1995 | Ruggio |
| 5,484,407 A | 1/1996 | Osypka |
| 5,484,412 A | 1/1996 | Pierpont |
| 5,484,418 A | 1/1996 | Quiachon et al. |
| 5,492,530 A | 2/1996 | Fischell et al. |
| 5,496,294 A | 3/1996 | Hergenrother et al. |
| 5,522,836 A | 6/1996 | Palermo |
| 5,527,292 A | 6/1996 | Adams et al. |
| 5,542,937 A | 8/1996 | Chee et al. |
| 5,558,635 A | 9/1996 | Cannon |
| 5,573,520 A | 11/1996 | Schwartz et al. |
| 5,599,326 A | 2/1997 | Carter |
| 5,628,754 A | 5/1997 | Shevlin et al. |
| 5,658,264 A | 8/1997 | Samson |
| 5,658,309 A | 8/1997 | Berthiaume et al. |
| 5,667,499 A | 9/1997 | Welch et al. |
| 5,695,483 A | 12/1997 | Samson |
| 5,702,373 A | 12/1997 | Samson |
| 5,707,376 A | 1/1998 | Kavteladze et al. |
| 5,730,734 A | 3/1998 | Adams et al. |
| 5,749,849 A | 5/1998 | Engelson |
| 5,749,858 A | 5/1998 | Cramer |
| 5,776,141 A | 7/1998 | Klein et al. |
| 5,794,629 A | 8/1998 | Frazee |
| 5,795,341 A | 8/1998 | Samson |
| 5,810,869 A | 9/1998 | Kaplan et al. |
| 5,827,229 A | 10/1998 | Auth et al. |
| 5,833,650 A | 11/1998 | Imran |
| 5,836,926 A | 11/1998 | Peterson et al. |
| 5,846,251 A | 12/1998 | Hart |
| 5,851,210 A | 12/1998 | Torossian |
| 5,853,400 A | 12/1998 | Samson |
| 5,876,367 A | 3/1999 | Kaganov et al. |
| 5,876,386 A | 3/1999 | Samson |
| 5,882,334 A | 3/1999 | Sepetka et al. |
| 5,895,399 A | 4/1999 | Barbut et al. |
| 5,908,407 A | 6/1999 | Frazee et al. |
| 5,913,848 A | 6/1999 | Luther et al. |
| 5,916,208 A | 6/1999 | Luther et al. |
| 5,921,952 A | 7/1999 | Desmond, III et al. |
| 5,928,192 A | 7/1999 | Maahs |
| 5,935,122 A | 8/1999 | Fourkas et al. |
| 5,938,645 A | 8/1999 | Gordon |
| 5,957,882 A | 9/1999 | Nita et al. |
| 5,976,093 A | 11/1999 | Jang |
| 5,976,178 A | 11/1999 | Goldsteen et al. |
| 5,997,508 A | 12/1999 | Lunn et al. |
| 5,997,523 A | 12/1999 | Jang |
| 6,004,310 A | 12/1999 | Bardsley et al. |
| 6,013,085 A | 1/2000 | Howard |
| 6,022,340 A | 2/2000 | Sepetka et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoska et al. |
| 6,110,139 A | 8/2000 | Loubser |
| 6,139,524 A | 10/2000 | Killion |
| 6,146,370 A | 11/2000 | Barbut |
| 6,146,373 A | 11/2000 | Cragg et al. |
| 6,146,415 A | 11/2000 | Fitz |
| 6,152,909 A | 11/2000 | Bagaoisan et al. |
| 6,152,912 A | 11/2000 | Jansen et al. |
| 6,159,230 A | 12/2000 | Samuels |
| 6,161,547 A | 12/2000 | Barbut |
| 6,165,199 A | 12/2000 | Barbut |
| 6,176,844 B1 | 1/2001 | Lee |
| 6,197,016 B1 | 3/2001 | Fourkas et al. |
| 6,206,868 B1 | 3/2001 | Parodi |
| 6,210,370 B1 | 4/2001 | Chi-Sing et al. |
| 6,234,971 B1 | 5/2001 | Jang |
| 6,238,430 B1 | 5/2001 | Klumb et al. |
| 6,254,628 B1 | 7/2001 | Wallace et al. |
| 6,258,080 B1 | 7/2001 | Samson |
| 6,270,477 B1 | 8/2001 | Bagaoisan et al. |
| 6,277,139 B1 | 8/2001 | Levinson et al. |
| 6,287,319 B1 | 9/2001 | Aboul-Hosn et al. |
| 6,295,989 B1 | 10/2001 | Connors, III |
| 6,295,990 B1 | 10/2001 | Lewis et al. |
| 6,306,106 B1 | 10/2001 | Boyle |
| 6,306,163 B1 | 10/2001 | Fitz |
| 6,364,900 B1 | 4/2002 | Heuser |
| 6,368,316 B1 | 4/2002 | Jansen et al. |

(56) References Cited

U.S. PATENT DOCUMENTS

| | | |
|---|---|---|
| 6,368,344 B1 | 4/2002 | Fitz |
| 6,379,325 B1 | 4/2002 | Benett et al. |
| 6,383,172 B1 | 5/2002 | Barbut |
| 6,413,235 B1 | 7/2002 | Parodi |
| 6,423,032 B2 | 7/2002 | Parodi |
| 6,423,086 B1 | 7/2002 | Barbut et al. |
| 6,428,531 B1 | 8/2002 | Visuri et al. |
| 6,435,189 B1 | 8/2002 | Lewis et al. |
| 6,436,087 B1 | 8/2002 | Lewis et al. |
| 6,454,741 B1 | 9/2002 | Muni et al. |
| 6,458,151 B1 | 10/2002 | Saltiel |
| 6,464,664 B1 | 10/2002 | Jonkman et al. |
| 6,481,439 B1 | 11/2002 | Lewis et al. |
| 6,482,172 B1 | 11/2002 | Thramann |
| 6,482,217 B1 | 11/2002 | Pintor et al. |
| 6,508,824 B1 | 1/2003 | Flaherty et al. |
| 6,517,520 B2 | 2/2003 | Chang et al. |
| 6,527,746 B1 | 3/2003 | Oslund et al. |
| 6,533,800 B1 | 3/2003 | Barbut |
| 6,540,712 B1 | 4/2003 | Parodi et al. |
| 6,544,276 B1 | 4/2003 | Azizi |
| 6,549,800 B1 | 4/2003 | Atalar et al. |
| 6,551,268 B1 | 4/2003 | Kaganov et al. |
| 6,555,057 B1 | 4/2003 | Barbut et al. |
| 6,562,049 B1 | 5/2003 | Norlander et al. |
| 6,562,052 B2 | 5/2003 | Nobles et al. |
| 6,582,390 B1 | 6/2003 | Sanderson |
| 6,582,396 B1 | 6/2003 | Parodi |
| 6,582,448 B1 | 6/2003 | Boyle et al. |
| 6,595,953 B1 | 7/2003 | Coppi et al. |
| 6,595,980 B1 | 7/2003 | Barbut |
| 6,605,074 B2 | 8/2003 | Zadno-Azizi et al. |
| 6,612,999 B2 | 9/2003 | Brennan et al. |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,573 B1 | 11/2003 | Parodi |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,650 B2 | 12/2003 | Sepetka et al. |
| 6,663,652 B2 | 12/2003 | Daniel et al. |
| 6,676,637 B1 | 1/2004 | Bonnette et al. |
| 6,679,893 B1 | 1/2004 | Tran |
| 6,682,505 B2 | 1/2004 | Bates et al. |
| 6,685,722 B1 | 2/2004 | Rosenbluth et al. |
| 6,692,473 B2 | 2/2004 | St. Cyr et al. |
| 6,702,782 B2 | 3/2004 | Miller et al. |
| 6,711,436 B1 | 3/2004 | Duhaylongsod |
| 6,719,717 B1 | 4/2004 | Johnson et al. |
| 6,730,104 B1 | 5/2004 | Sepetka et al. |
| 6,733,517 B1 | 5/2004 | Collins |
| 6,740,104 B1 | 5/2004 | Solar et al. |
| 6,749,627 B2 | 6/2004 | Thompson et al. |
| 6,755,803 B1 | 6/2004 | Le et al. |
| 6,755,847 B2 | 6/2004 | Eskuri |
| 6,758,854 B1 | 7/2004 | Butler et al. |
| 6,764,464 B2 | 7/2004 | McGuckin, Jr. et al. |
| 6,790,204 B2 | 9/2004 | Zadno-Azizi et al. |
| 6,824,545 B2 | 11/2004 | Sepetka et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,905,505 B2 | 6/2005 | Nash et al. |
| 6,908,474 B2 | 6/2005 | Hogendijk et al. |
| 6,929,632 B2 | 8/2005 | Nita et al. |
| 6,929,634 B2 | 8/2005 | Dorros et al. |
| 6,936,060 B2 | 8/2005 | Hogendijk et al. |
| 6,958,059 B2 | 10/2005 | Zadno-Azizi |
| 6,960,189 B2 | 11/2005 | Bates et al. |
| 6,972,030 B2 | 12/2005 | Lee et al. |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 | 4/2006 | Schonholz et al. |
| 7,033,325 B1 | 4/2006 | Sullivan |
| 7,033,336 B2 | 4/2006 | Hogendijk |
| 7,033,344 B2 | 4/2006 | Imran |
| 7,048,758 B2 | 5/2006 | Boyle et al. |
| 7,063,714 B2 | 6/2006 | Dorros et al. |
| 7,083,594 B2 | 8/2006 | Coppi |
| 7,104,979 B2 | 9/2006 | Jansen et al. |
| 7,108,677 B2 | 9/2006 | Courtney et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,169,165 B2 | 1/2007 | Belef et al. |
| 7,172,621 B2 | 2/2007 | Theron |
| 7,223,253 B2 | 5/2007 | Hogendijk |
| 7,232,452 B2 | 6/2007 | Adams et al. |
| 7,250,042 B2 | 7/2007 | Kataishi et al. |
| 7,306,585 B2 | 12/2007 | Ross |
| 7,309,334 B2 | 12/2007 | von Hoffmann |
| 7,316,678 B2 | 1/2008 | Nash et al. |
| 7,367,982 B2 | 5/2008 | Nash et al. |
| 7,374,560 B2 | 5/2008 | Ressemann et al. |
| 7,374,561 B2 | 5/2008 | Barbut |
| 7,384,412 B2 | 6/2008 | Coppi |
| 7,402,151 B2 | 7/2008 | Rosenman et al. |
| 7,422,579 B2 | 9/2008 | Wahr et al. |
| 7,458,980 B2 | 12/2008 | Barbut |
| 7,497,844 B2 | 3/2009 | Spear et al. |
| 7,524,303 B1 | 4/2009 | Don Michael et al. |
| 7,534,250 B2 | 5/2009 | Schaeffer et al. |
| 7,731,683 B2 | 6/2010 | Jang et al. |
| 7,766,049 B2 | 8/2010 | Miller et al. |
| 7,766,820 B2 | 8/2010 | Core |
| 7,806,906 B2 | 10/2010 | Don Michael |
| 7,815,626 B1 | 10/2010 | McFadden et al. |
| 7,842,065 B2 | 11/2010 | Belef et al. |
| 7,854,746 B2 | 12/2010 | Dorn et al. |
| 7,867,216 B2 | 1/2011 | Wahr et al. |
| 7,905,856 B2 | 3/2011 | McGuckin, Jr. et al. |
| 7,905,877 B1 | 3/2011 | Jimenez et al. |
| 7,909,812 B2 | 3/2011 | Jansen et al. |
| 7,927,309 B2 | 4/2011 | Palm |
| 7,927,347 B2 | 4/2011 | Hogendijk et al. |
| 7,972,294 B2 | 7/2011 | Nash et al. |
| 7,972,308 B2 | 7/2011 | Putz |
| 7,998,104 B2 | 8/2011 | Chang |
| 8,021,351 B2 | 9/2011 | Boldenow et al. |
| 8,029,533 B2 | 10/2011 | Bagaoisan et al. |
| 8,048,032 B2 | 11/2011 | Root et al. |
| 8,052,640 B2 | 11/2011 | Fiorella et al. |
| 8,066,757 B2 | 11/2011 | Ferrera et al. |
| 8,142,413 B2 | 3/2012 | Root et al. |
| RE43,300 E | 4/2012 | Saadat et al. |
| 8,152,782 B2 | 4/2012 | Jang et al. |
| 8,157,760 B2 | 4/2012 | Criado et al. |
| 8,172,831 B2 | 5/2012 | Webler, Jr. |
| 8,181,324 B2 | 5/2012 | McFadden et al. |
| 8,221,348 B2 | 7/2012 | Hackett et al. |
| 8,231,600 B2 | 7/2012 | von Hoffmann |
| 8,251,978 B2 | 8/2012 | Nash et al. |
| 8,252,010 B1 | 8/2012 | Raju et al. |
| 8,292,850 B2 | 10/2012 | Root et al. |
| 8,343,089 B2 | 1/2013 | Chang |
| 8,414,516 B2 | 4/2013 | Chang |
| 8,425,549 B2 | 4/2013 | Lenker et al. |
| 8,465,456 B2 | 6/2013 | Stivland |

(56) References Cited

U.S. PATENT DOCUMENTS

| | | |
|---|---|---|
| 8,523,801 B2 | 9/2013 | Nash et al. |
| 8,545,552 B2 | 10/2013 | Garrison et al. |
| 8,574,245 B2 | 11/2013 | Garrison et al. |
| 8,708,954 B2 | 4/2014 | Webler |
| 8,870,805 B2 | 10/2014 | Chang |
| RE45,380 E | 2/2015 | Root et al. |
| 8,961,549 B2 | 2/2015 | Conn |
| 8,996,095 B2 | 3/2015 | Anderson et al. |
| 9,034,007 B2 | 5/2015 | Janardhan |
| 9,126,018 B1 | 9/2015 | Garrison |
| 9,144,662 B2 | 9/2015 | Di Caprio et al. |
| RE45,760 E | 10/2015 | Root et al. |
| RE45,776 E | 10/2015 | Root et al. |
| 2001/0044598 A1 | 11/2001 | Parodi |
| 2001/0049486 A1 | 12/2001 | Evans et al. |
| 2001/0049517 A1 | 12/2001 | Zadno-Azizi et al. |
| 2002/0087119 A1 | 7/2002 | Parodi |
| 2002/0128679 A1 | 9/2002 | Turovskiy et al. |
| 2002/0133111 A1 | 9/2002 | Shadduck |
| 2002/0151922 A1 | 10/2002 | Hogendijk et al. |
| 2002/0156455 A1 | 10/2002 | Barbut |
| 2002/0156460 A1 | 10/2002 | Ye et al. |
| 2002/0165598 A1 | 11/2002 | Wahr et al. |
| 2002/0173815 A1 | 11/2002 | Hogendijk et al. |
| 2002/0183783 A1 | 12/2002 | Shadduck |
| 2003/0040762 A1 | 2/2003 | Dorros et al. |
| 2003/0065356 A1 | 4/2003 | Tsugita et al. |
| 2003/0069468 A1 | 4/2003 | Bolling et al. |
| 2003/0078562 A1 | 4/2003 | Makower et al. |
| 2003/0186203 A1 | 10/2003 | Aboud |
| 2003/0212304 A1 | 11/2003 | Lattouf |
| 2003/0212384 A1 | 11/2003 | Hayden |
| 2004/0059243 A1 | 3/2004 | Flores et al. |
| 2004/0116878 A1 | 6/2004 | Byrd et al. |
| 2004/0133232 A1 | 7/2004 | Rosenbluth et al. |
| 2004/0138608 A1 | 7/2004 | Barbut et al. |
| 2004/0210194 A1 | 10/2004 | Bonnette et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0209559 A1 | 9/2005 | Thornton et al. |
| 2005/0273051 A1 | 12/2005 | Coppi |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0089618 A1 | 4/2006 | McFerran et al. |
| 2006/0135961 A1 | 6/2006 | Rosenman et al. |
| 2006/0200191 A1 | 9/2006 | Zadno-Azizi |
| 2006/0271098 A1 | 11/2006 | Peacock |
| 2007/0021778 A1* | 1/2007 | Carly ............... A61B 17/083 606/213 |
| 2007/0173784 A1 | 7/2007 | Johansson et al. |
| 2007/0197956 A1 | 8/2007 | Le et al. |
| 2007/0198028 A1 | 8/2007 | Miloslavski et al. |
| 2007/0198049 A1 | 8/2007 | Barbut |
| 2008/0082107 A1 | 4/2008 | Miller et al. |
| 2008/0140010 A1 | 6/2008 | Kennedy et al. |
| 2008/0177245 A1 | 7/2008 | Mesallum |
| 2008/0200946 A1 | 8/2008 | Braun et al. |
| 2009/0018455 A1 | 1/2009 | Chang |
| 2009/0024072 A1 | 1/2009 | Criado et al. |
| 2009/0030400 A1 | 1/2009 | Bose et al. |
| 2009/0198172 A1 | 8/2009 | Garrison et al. |
| 2009/0254166 A1 | 10/2009 | Chou et al. |
| 2009/0264865 A1 | 10/2009 | Kawai |
| 2009/0299393 A1 | 12/2009 | Martin et al. |
| 2010/0004607 A1 | 1/2010 | Wilson et al. |
| 2010/0042118 A1 | 2/2010 | Garrison et al. |
| 2010/0063479 A1* | 3/2010 | Merdan ............... A61B 1/0011 604/528 |
| 2010/0063480 A1 | 3/2010 | Shireman |
| 2010/0094330 A1 | 4/2010 | Barbut |
| 2010/0114017 A1 | 5/2010 | Lenker et al. |
| 2010/0145308 A1 | 6/2010 | Layman et al. |
| 2010/0185216 A1 | 7/2010 | Garrison et al. |
| 2010/0204672 A1 | 8/2010 | Lockhart et al. |
| 2010/0204684 A1 | 8/2010 | Garrison et al. |
| 2010/0217276 A1 | 8/2010 | Garrison et al. |
| 2010/0228269 A1 | 9/2010 | Garrison et al. |
| 2010/0256600 A1 | 10/2010 | Ferrera |
| 2010/0318097 A1 | 12/2010 | Ferrera et al. |
| 2011/0009875 A1 | 1/2011 | Grandfield et al. |
| 2011/0034986 A1* | 2/2011 | Chou ............... A61B 17/0057 623/1.11 |
| 2011/0087147 A1 | 4/2011 | Garrison et al. |
| 2011/0112567 A1 | 5/2011 | Lenker et al. |
| 2011/0125181 A1 | 5/2011 | Brady et al. |
| 2011/0152760 A1 | 6/2011 | Parker |
| 2011/0238041 A1* | 9/2011 | Lim ............... A61M 25/0045 604/527 |
| 2012/0310212 A1 | 12/2012 | Fischell et al. |
| 2013/0035628 A1* | 2/2013 | Garrison ............... A61B 17/22 604/8 |
| 2013/0116701 A1 | 5/2013 | Wang et al. |
| 2013/0184735 A1 | 7/2013 | Fischell et al. |
| 2013/0281788 A1 | 10/2013 | Garrison |
| 2014/0025043 A1 | 1/2014 | Wang et al. |
| 2014/0155783 A1 | 6/2014 | Starksen et al. |
| 2014/0257186 A1 | 9/2014 | Kerr |
| 2014/0296769 A1 | 10/2014 | Hyde et al. |
| 2014/0296868 A1 | 10/2014 | Garrison et al. |
| 2015/0174368 A1 | 6/2015 | Garrison et al. |

FOREIGN PATENT DOCUMENTS

| | | |
|---|---|---|
| EP | 1440663 A1 | 7/2004 |
| JP | 2003-522560 A | 7/2003 |
| JP | 2005-500138 A | 1/2005 |
| WO | WO-95/05209 A1 | 2/1995 |
| WO | WO-98/38930 A1 | 9/1998 |
| WO | WO-99/45835 A2 | 9/1999 |
| WO | WO-00/32266 A1 | 6/2000 |
| WO | WO-00/76390 A2 | 12/2000 |
| WO | WO-01/15767 A1 | 3/2001 |
| WO | WO-01/58365 A1 | 8/2001 |
| WO | WO-02/32495 A1 | 4/2002 |
| WO | WO-03/018085 A2 | 3/2003 |
| WO | WO-03/090831 A2 | 11/2003 |
| WO | WO-2004/006803 A1 | 1/2004 |
| WO | WO-2005/051206 A1 | 6/2005 |
| WO | WO-2008/144587 A2 | 11/2008 |
| WO | WO-2009012473 A3 | 1/2009 |
| WO | WO-2009099764 A1 | 8/2009 |
| WO | WO-2009100210 A1 | 8/2009 |
| WO | WO-2010/075445 A1 | 7/2010 |
| WO | WO-2012/047803 A3 | 4/2012 |

OTHER PUBLICATIONS

Bergeron et al. (1999). "Percutaneous stenting of the internal carotid artery: the European Cast I Study" J. Endovasc. Surg. 6:155-159.

Bergeron et al. (2008) Meet Presentation, Cannes, French Riviera "Why I do not use routine femoral access for CAS".

Bergeron P. et al. (1996) "Recurrent Carotid Disease: Will Stents be an alternative to surgery?" J Endovasc Surg; 3: 76-79.

Bourekas, E. C., A. P. Slivka, et al. (2004). "Intraarterial thrombolytic therapy within 3 hours of the onset of stroke." Neurosurgery 54(1): 39-44; discussion 44-6.

Cohen et al., "A reappraisal of the common carotid artery as an access site in interventional procedures for acute stroke therapies", Case Reports, Journal of Clinical Neuroscience 19 (2012) pp. 323-326.

Criado et al. (1997) "Evolving indications for and early results of carotid artery stenting" Am. J. Surg.; 174:111-114.

Diederich et al. (2004) "First Clinical experiences with an endovascular clamping system for neuroprotection during carotid stenting" Eur. J. Vasc. Endovasc. Surg. 28:629-633.

Diethrich et al., (1996). "Percutaneous techniques for endoluminal carotid interventions" J. Endovasc. Surg. 3:182-202.

Diethrich, E. B. (2004). The Direct Cervical Carotid Artery Approach. Carotid Artery Stenting: Current Practice and Tech-

(56) References Cited

OTHER PUBLICATIONS niques. N. Al-Mubarak, G. S. Roubin, S. Iyer and J. Vitek. Philadephia, Lippincott Williams & Wilkins: Chapter 11. pp. 124-136.
Feldtman, R. W., C. J. Buckley, et al. (2006). "How I do it: cervical access for carotid artery stenting." Am J Surg 192(6): 779-81.
Fiorella, D., M. Kelly, et al. (2008). "Endovascular Treatment of Cerebral Aneurysms." Endovascular Today June.
Frazee, J. G. and X. Luo (1999). "Retrograde transvenous perfusion." Crit Care Clin 15(4): 777-88, vii.
Frazee, J. G., X. Luo, et al. (1998). "Retrograde transvenous neuroperfusion: a back door treatment for stroke." Stroke 29(9): 1912-6.
Goldstein "Acute Ischemic Stroke Treatment in 2007" *Circ* 116:1504-1514 (2007).
Gray et al. (2007) "The CAPTURE registry: Results of carotid stenting with embolic protection in the post approval setting" *Cath. Cardovasc. Interven.* 69:341-348.
Henry et al. (1999) "Carotid stenting with cerebral protection: First clinical experience using the PercuSurge GuardWire System" J. Endovasc. Surg. 6:321-331.
Hoffer et al. "Percutaneous Arterial Closure Devices" *J. Vasc. Interv. Radiol.* 14:865-885 (2003).
Howell, M., K. Doughtery, et al. (2002). "Percutaneous repair of abdominal aortic aneurysms using the AneuRx stent graft and the percutaneous vascular surgery device." Catheter Cardiovasc Interv 55(3): 281-7.
Koebbe, C. J., E. Veznedaroglu, et al. (2006). "Endovascular management of intracranial aneurysms: current experience and future advances." Neurosurgery 59(5 Suppl 3): S93-102; discussion S3-13.
Luebke, T et al. (2007) "Meta-analysis of randomized trials comparing carotid endarterectomy and endovascular treatment" *Eur. J. Vasc. Endovasc. Surg.* 34:470-479.
MacDonald, S. (2006) "Is there any evidence that cerebral protection is beneficial?" *J. Cardiovasc. Surg.* 47:127-36.
Mas et al. (2006) "Endarterectomy versus stenting in patients with symptomatic severe carotid stenosis" *NEJM* 355:1660-71.
MomaPresn (AET) 2002 Biamino, G; MO.MA as a distal protective device, University of Leipzig—Heart Center Department of Clinical and Interventional; Angiology Leipzig, Germany; 2002.
Nesbit, G. M., G. Luh, et al. (2004). "New and future endovascular treatment strategies for acute ischemic stroke." J Vasc Interv Radiol 15(1 Pt 2): S103-10.
Nii, K., K. Kazekawa, et al. (2006). "Direct carotid puncture for the endovascular treatment of anterior circulation aneurysms." AJNR Am J Neuroradiol 27(7): 1502-4.
Ouriel, K., R. K. Greenberg, et al. (2001). "Hemodynamic conditions at the carotid bifurcation during protective common carotid occlusion." J Vasc Surg 34(4): 577-80.
Parodi et al. (2000). "Initial evaluation of carotid angioplasty and stenting with three different cerebral protection devices" J. Vasc. Surg. 32:1127-1136.
Parodi, J. C., L. M. Ferreira, et al. (2005). "Cerebral protection during carotid stenting using flow reversal." J Vasc Surg 41(3): 416-22.
Perez-Arjona, E. A., Z. DelProsto, et al. (2004). "Direct percutaneous carotid artery stenting with distal protection: technical case report." Neurol Res 26(3): 338-41.
Reekers, J. A. (1998). "A balloon protection sheath to prevent peripheral embolization during aortoiliac endovascular procedures." Cardiovasc Intervent Radiol 21(5): 431-3.
Reimers et al. (2005). "Proximal endovascular flow blockage for cerebral protection during carotid artery stenting: Results froma prospective multicenter registry" J. Endovasc. Ther. 12:156-165.
Ribo, M., C. Molina, et al. (2008). "Buying Time for Recanalization in Acute Stroke: Arterial Blood Infusion Beyond the Occluding Clot as a Neuroprotective Strategy." J Neuroimaging.
Ross, I. B. and G. D. Luzardo (2006). "Direct access to the carotid circulation by cut down for endovascular neuro-interventions." Sur. Neurol 65(2): 207-11; discussion 211.
Stejskal, et al., "Experience of 500 Cases of Neurophysiological Monitoring in Carotid Endarterectomy", Acta Neurochir, 2007, 149:681-689.
Theron, et al. "New Triple Coaxial Catheter System for Carotid Angioplasty with Cerebral Protection.". AJNR 11:869-874, Sep./Oct. 1990. 0195-6108/90/1106-0869. American Society of Neurology.

\* cited by examiner

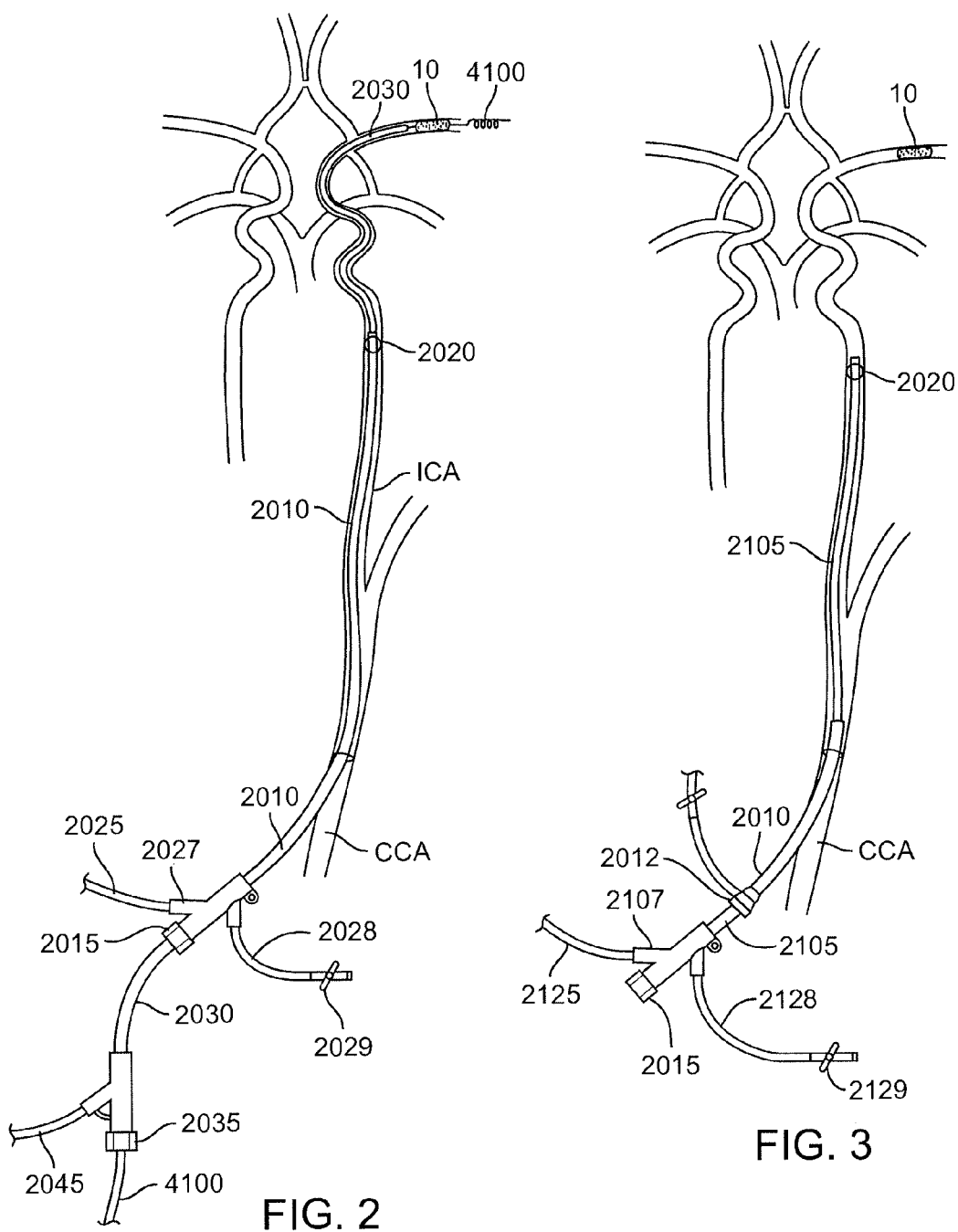

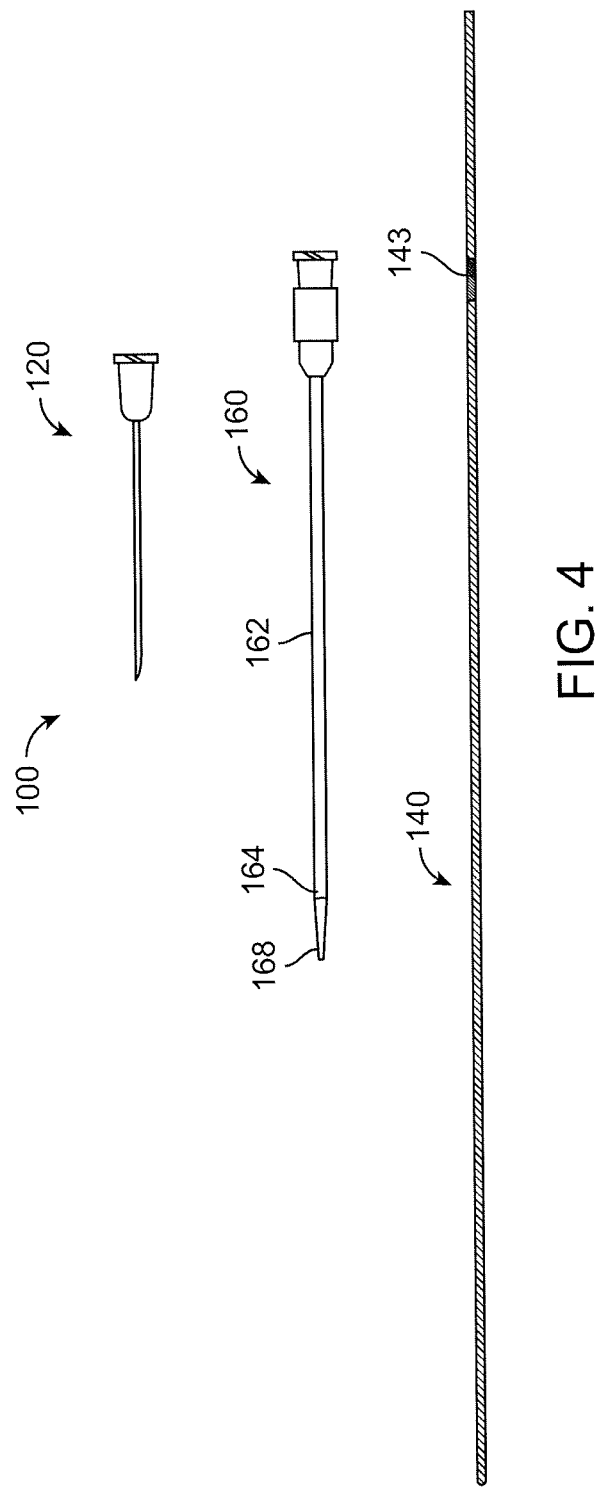

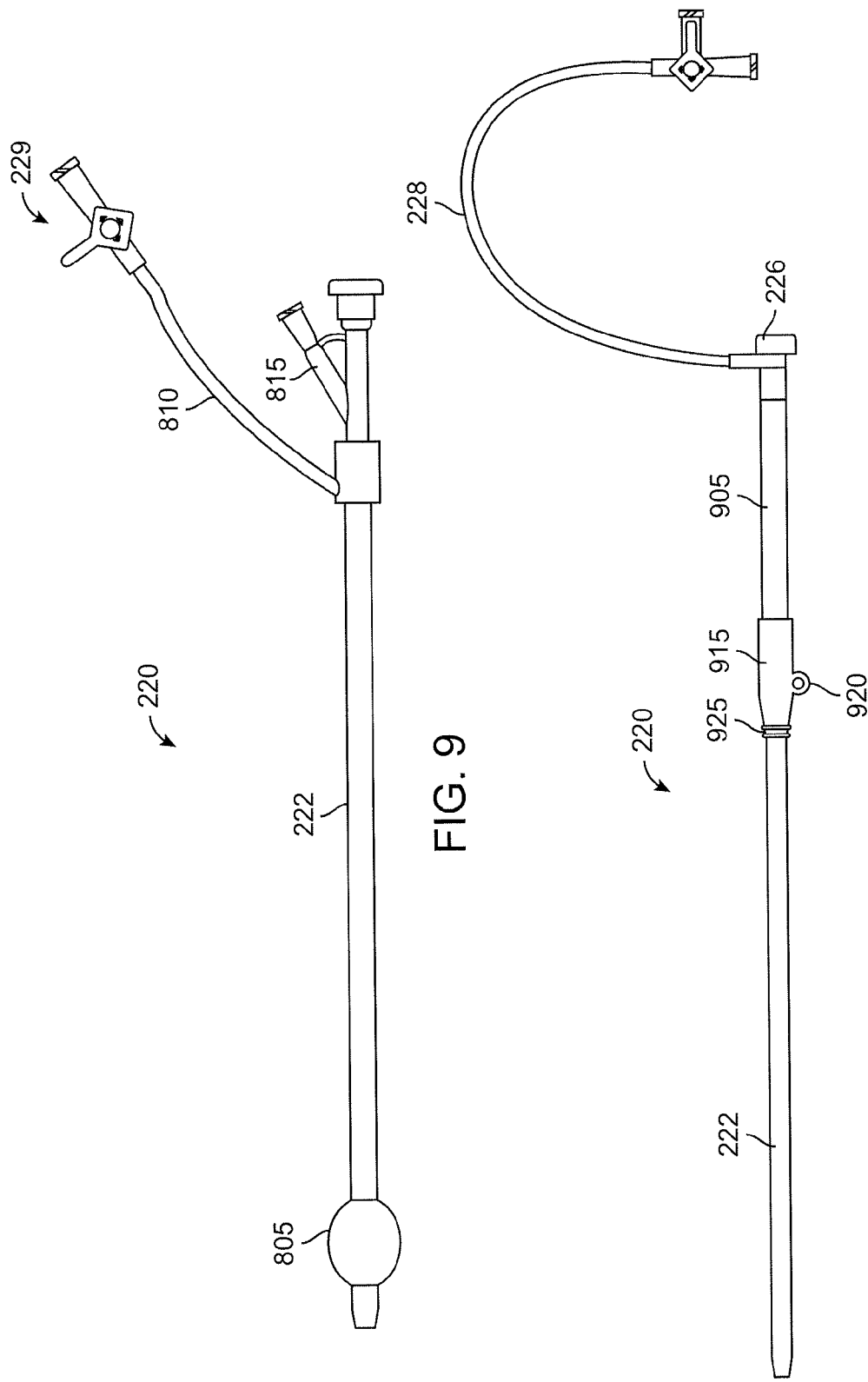

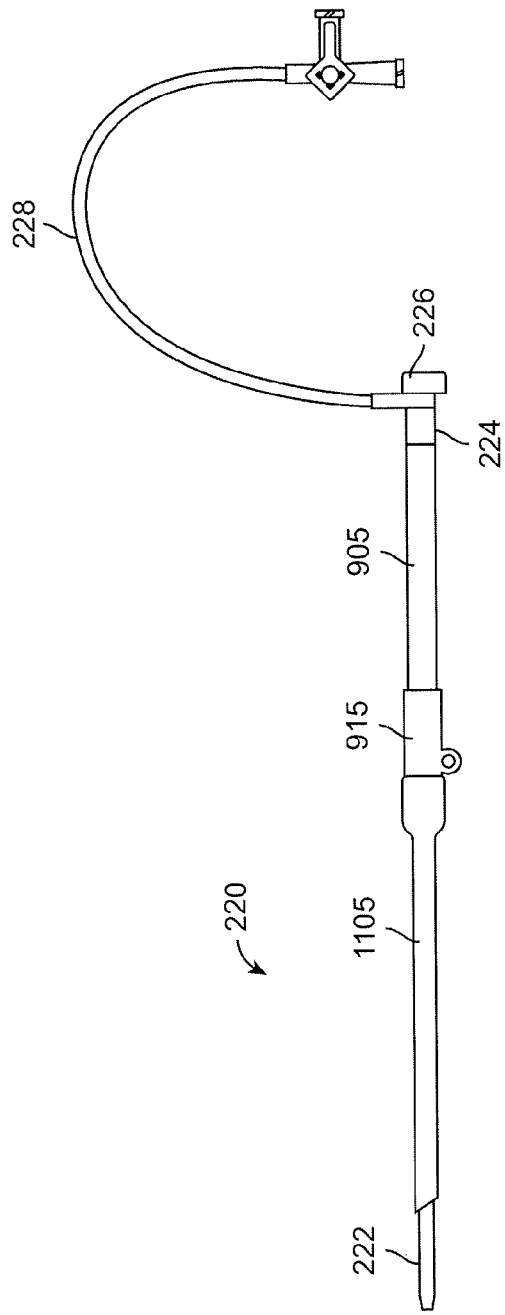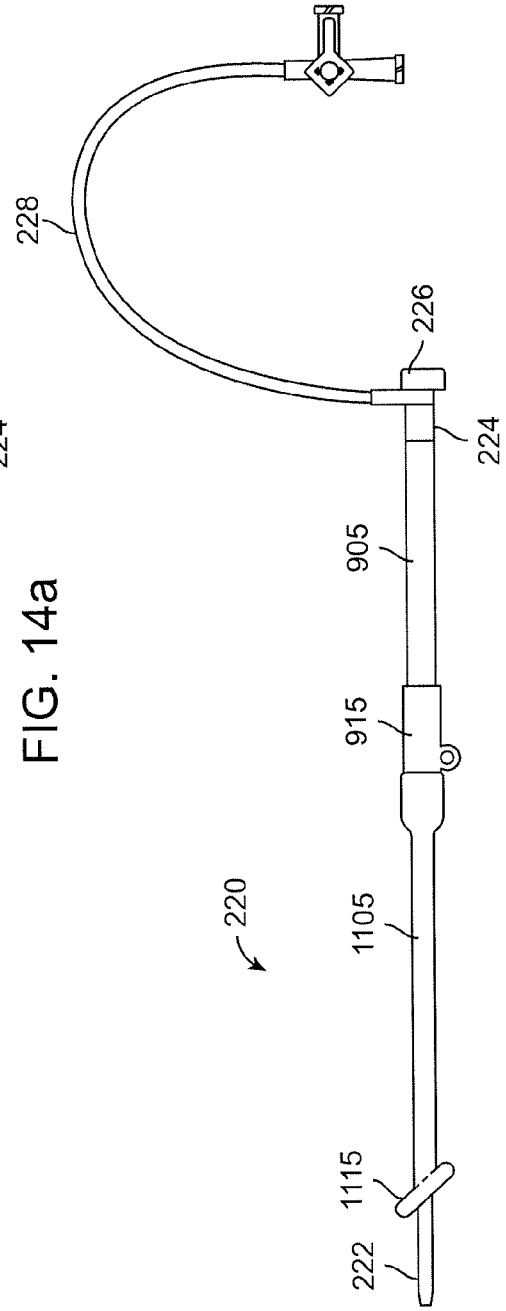
FIG. 14a
FIG. 14b

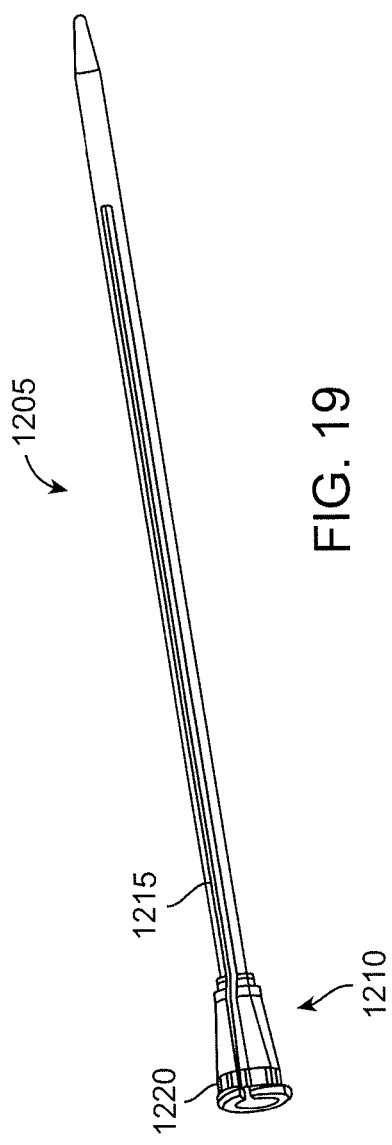
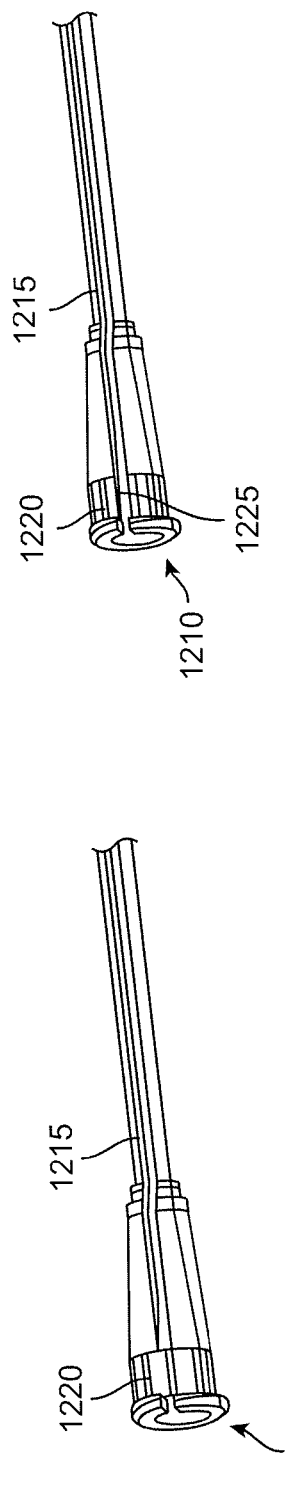

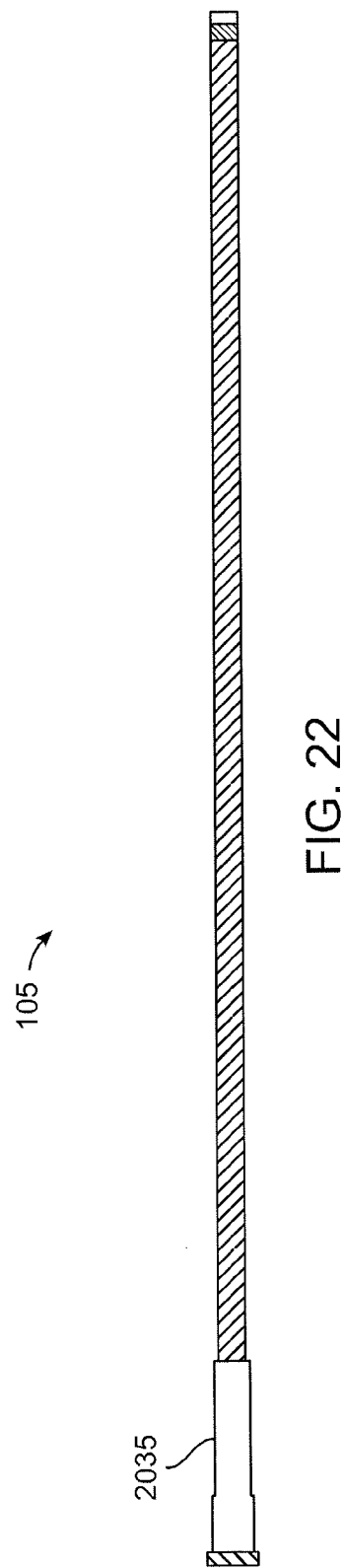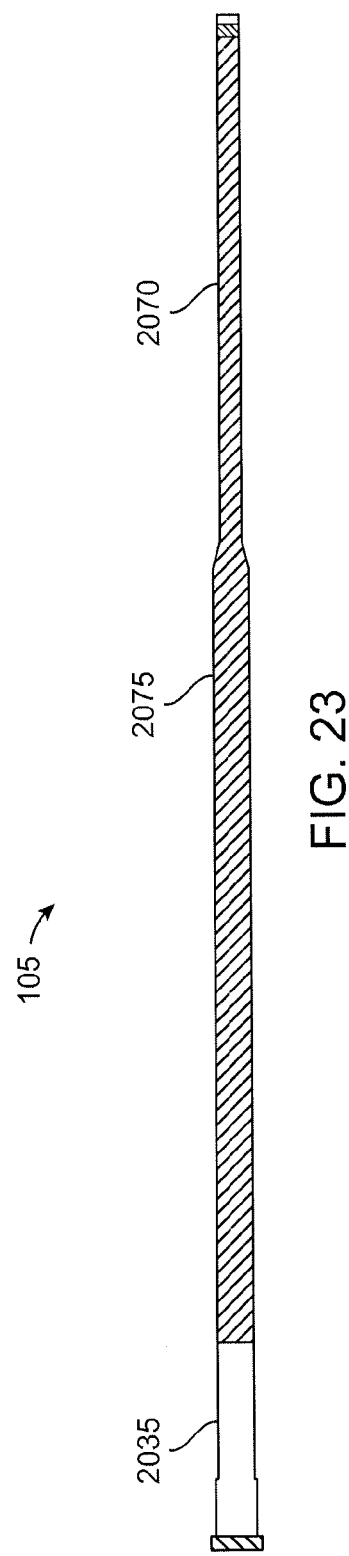

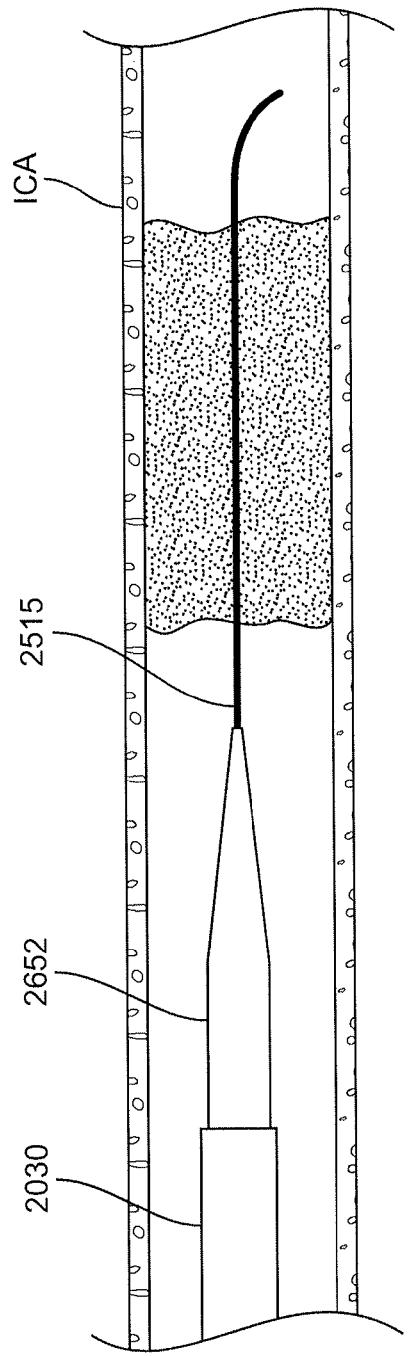
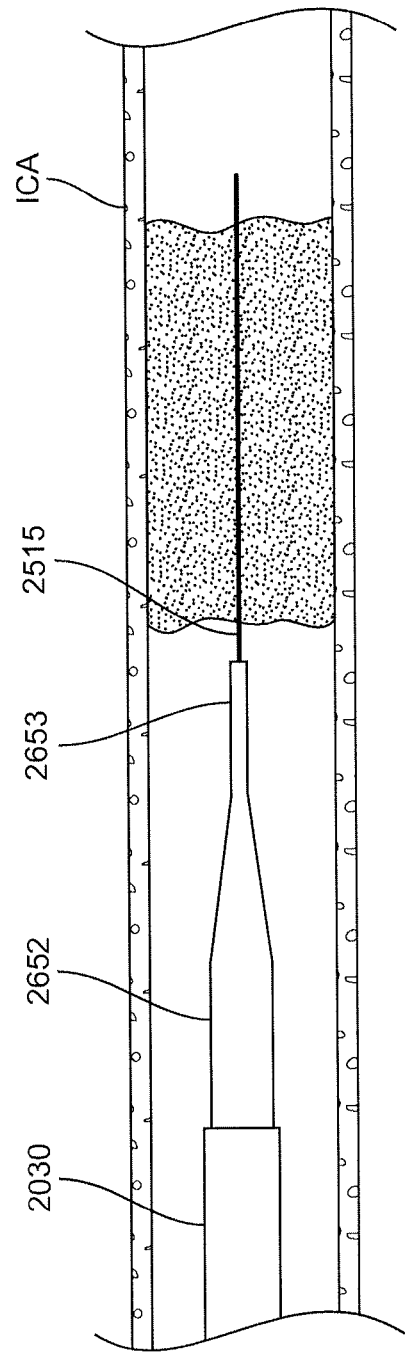
FIG. 25A
FIG. 25B

|  | Distal ID, Inches | Distal Length, cm | Proximal ID, inches | Proximal Length, cm | Theoretical Resistance (dynes*sec)/ cm^4) | % Improvement over Navien 058 |
|---|---|---|---|---|---|---|
| Navien 058 | 0.058 | 115 | n/a | n/a | 368055 | N/A |
| Penumbra 5 MAX | 0.054 | 20 | 0.064 | 112 | 326971 | 13% |
| Penumbra 5 Max ACE | 0.060 | 20 | 0.068 | 112 | 245611 | 50% |
| Transcarotid Distal Catheter .058" ID | 0.058 | 62 | n/a | n/a | 198430 | 85% |
| Stepped Transcarotid Distal Catheter, .058" ID | 0.058 | 20 | 0.068 | 40 | 131766 | 179% |
| Transfemoral Telescoping Catheter/Sheath System, .058" ID catheter and 5F Sheath | 0.058 | 20 | 0.074 | 90 | 172713 | 113% |
| Transcarotid Telescoping Catheter/Sheath System, .058" ID catheter and 5F Sheath | 0.058 | 15 | 0.074 | 30 | 84242 | 337% |

FIG. 54

|  | Distal ID, Inches | Distal Length, cm | Proximal ID, inches | Proximal Length, cm | Theoretical Resistance (dynes*sec)/ cm^4) | % Improvement over Navien 072 |
|---|---|---|---|---|---|---|
| Navien 072 | 0.072 | 105 | n/a | n/a | 141510 | N/A |
| Transcarotid Distal Catheter, .071" ID | 0.071 | 58 | n/a | n/a | 82665 | 71% |
| Stepped Transcarotid Distal Catheter, .071" ID | 0.071 | 20 | 0.081 | 40 | 62160 | 128% |
| Transfemoral Telescoping Catheter/Sheath System, .071" ID catheter and 6F Sheath | 0.071 | 20 | 0.087 | 90 | 85403 | 66% |
| Transcarotid Telescoping Catheter/Sheath System, .071" ID catheter and 6F Sheath | 0.071 | 15 | 0.087 | 30 | 40345 | 251% |

FIG. 55

|  | Flow Rate, mL/min | % Improvement over Navien 058 |
| --- | --- | --- |
| Navien 058 | 129 | n/a |
| Penumbra 5 Max ACE | 171 | 33% |
| Transcarotid Distal Catheter, .058" ID | 205 | 59% |

FIG. 56

|  | Flow Rate, mL/min | % Improvement over Navien 072 |
| --- | --- | --- |
| Navien 072 | 261 | n/a |
| Transcarotid Distal Catheter, .071" ID | 321 | 23% |

FIG. 57

METHODS AND SYSTEMS FOR TREATMENT OF ACUTE ISCHEMIC STROKE

REFERENCE TO PRIORITY DOCUMENTS

This application claims priority to (1) U.S. Provisional Patent Application Ser. No. 61/919,945, filed Dec. 23, 2013, entitled "Methods and Systems for Treatment of Acute Ischemic Stroke"; (2) U.S. Provisional Patent Application Ser. No. 62/083,128, filed Nov. 21, 2014, entitled "Methods and Systems for Treatment of Acute Ischemic Stroke"; (3) U.S. Provisional Patent Application Ser. No. 62/029,799, filed Jul. 28, 2014, entitled "Intravascular Catheter with Smooth Transitions of Flexibility"; (4) U.S. Provisional Patent Application Ser. No. 62/075,101, filed Nov. 4, 2014, entitled "Transcarotid Neurovascular Catheter"; (5) U.S. Provisional Patent Application Ser. No. 62/046,112, filed Sep. 4, 2014, entitled "Methods and Devices for Transcarotid Access"; and (6) U.S. Provisional Patent Application Ser. No. 62/075,169, filed Nov. 4, 2014, entitled "Methods and Devices for Transcarotid Access." The disclosures of the provisional patent applications are incorporated by reference in their entirety and priority to the filing dates is claimed.

BACKGROUND

The present disclosure relates generally to medical methods and devices for the treatment of acute ischemic stroke. More particularly, the present disclosure relates to methods and systems for transcarotid access of the cerebral arterial vasculature and treatment of cerebral occlusions.

Acute ischemic stroke is the sudden blockage of adequate blood flow to a section of the brain, usually caused by thrombus or other emboli lodging or forming in one of the blood vessels supplying the brain. If this blockage is not quickly resolved, the ischemia may lead to permanent neurologic deficit or death. The timeframe for effective treatment of stroke is within 3 hours for intravenous (IV) thrombolytic therapy and 6 hours for site-directed intra-arterial thrombolytic therapy or interventional recanalization of a blocked cerebral artery. Reperfusing the ischemic brain after this time period has no overall benefit to the patient, and may in fact cause harm due to the increased risk of intracranial hemorrhage from fibrinolytic use. Even within this time period, there is strong evidence that the shorter the time period between onset of symptoms and treatment, the better the results. Unfortunately, the ability to recognize symptoms, deliver patients to stroke treatment sites, and finally to treat these patients within this timeframe is rare. Despite treatment advances, stroke remains the third leading cause of death in the United States.

Endovascular treatment of acute stroke is comprised of either the intra-arterial administration of thrombolytic drugs such as recombinent tissue plasminogen activator (rtPA), mechanical removal of the blockage, or a combination of the two. As mentioned above, these interventional treatments must occur within hours of the onset of symptoms. Both intra-arterial (IA) thrombolytic therapy and interventional thrombectomy involve accessing the blocked cerebral artery via endovascular techniques and devices.

Like IV thrombolytic therapy, IA thrombolytic therapy alone has the limitation in that it may take several hours of infusion to effectively dissolve the clot. Mechanical therapies have involved capturing and removing the clot, dissolving the clot, disrupting and suctioning the clot, and/or creating a flow channel through the clot. One of the first mechanical devices developed for stroke treatment is the MERCI Retriever System (Concentric Medical, Redwood City, Calif.). A balloon-tipped guide catheter is used to access the internal carotid artery (ICA) from the femoral artery. A microcatheter is placed through the guide catheter and used to deliver the coil-tipped retriever across the clot and is then pulled back to deploy the retriever around the clot. The microcatheter and retriever are then pulled back, with the goal of pulling the clot, into the balloon guide catheter while the balloon is inflated and a syringe is connected to the balloon guide catheter to aspirate the guide catheter during clot retrieval. This device has had initially positive results as compared to thrombolytic therapy alone.

Other thrombectomy devices utilize expandable cages, baskets, or snares to capture and retrieve clot. Temporary stents, sometimes referred to as stentrievers or revascularization devices, are utilized to remove or retrieve clot as well as restore flow to the vessel. A series of devices using active laser or ultrasound energy to break up the clot have also been utilized. Other active energy devices have been used in conjunction with intra-arterial thrombolytic infusion to accelerate the dissolution of the thrombus. Many of these devices are used in conjunction with aspiration to aid in the removal of the clot and reduce the risk of emboli. Frank suctioning of the clot has also been used with single-lumen catheters and syringes or aspiration pumps, with or without adjunct disruption of the clot. Devices which apply powered fluid vortices in combination with suction have been utilized to improve the efficacy of this method of thrombectomy. Finally, balloons or stents have been used to create a patent lumen through the clot when clot removal or dissolution was not possible.

SUMMARY

Disclosed are methods and devices that enable safe, rapid and relatively short transcarotid access to the cerebral and intracranial arteries to treat acute ischemic stroke. The methods and devices include one or more transcarotid access devices, catheters, and thrombectomy devices to remove the occlusion. Methods and devices are also included to provide aspiration and passive flow reversal for the purpose of facilitating removal of the occlusion as well as minimizing distal emboli. The system offers the user a degree of flow control so as to address the specific hemodynamic requirements of the cerebral vasculature. The disclosed methods and devices also include methods and devices to protect the cerebral penumbra during the procedure to minimize injury to brain. In addition, the disclosed methods and devices provide a way to securely close the access site in the carotid artery to avoid the potentially devastating consequences of a transcarotid hematoma.

In one aspect, there is disclosed a system of devices for treating an artery, comprising: an arterial access sheath adapted to introduce an interventional catheter into an artery, the arterial access sheath including a sheath body sized and shaped to be introduced into a common carotid artery via a carotid artery access site, the sheath body defining an internal lumen that provides a passageway for introducing a catheter into the common carotid artery when the first elongated body is positioned in the common carotid artery, wherein the sheath body has a proximal section and a distalmost section that is more flexible than the proximal section, and wherein a ratio of an entire length of the distalmost section to an overall length of the sheath body is one tenth to one half the overall length of the sheath body; an elongated dilator positionable within the internal lumen of the sheath body, wherein the arterial access sheath and the dilator can be collectively introduced into the common carotid artery; and a catheter formed of an elongated catheter body sized and shaped to be introduced via a carotid artery access site into a common carotid artery through the internal lumen of the arterial access sheath, the catheter body sized and shaped to be navigated distally to a intracranial artery through the common carotid artery via the access location in the carotid artery, wherein the catheter body has a length of 40 cm to 70 cm, and wherein the catheter body has a proximal most section and a distal most section wherein the proximal most section is a stiffest portion of the catheter body, and wherein the catheter body has an overall length and a distal most section length such that the distal most section can be positioned in an intracranial artery and at least a portion of the proximal most section is positioned in the common carotid artery during use.

Other features and advantages should be apparent from the following description of various embodiments, which illustrate, by way of example, the principles of the invention.

BRIEF DESCRIPTION OF THE DRAWINGS

FIG. 2 illustrates another embodiment of a system of devices for transcarotid access and treatment of acute ischemic stroke with a balloon-tipped arterial access device and a thrombectomy device.

FIG. 3 illustrates another embodiment of a system of devices for transcarotid access and treatment of acute ischemic stroke with a balloon-tipped guide catheter.

FIG. 4 shows an embodiment of a transcarotid initial access system.

FIGS. 6-11 show embodiments of a transcarotid arterial access sheath.

FIGS. 14a and 14b show embodiments of an arterial access device with a sheath stopper.

FIGS. 19-21 show embodiments of dilators.

FIGS. 22-23 show embodiments of catheters.

FIGS. 25A and 25B show examples of catheters and tapered dilators in an artery.

FIGS. 54-57 show tables containing data related to the devices disclosed herein.

DETAILED DESCRIPTION

Figure 1:
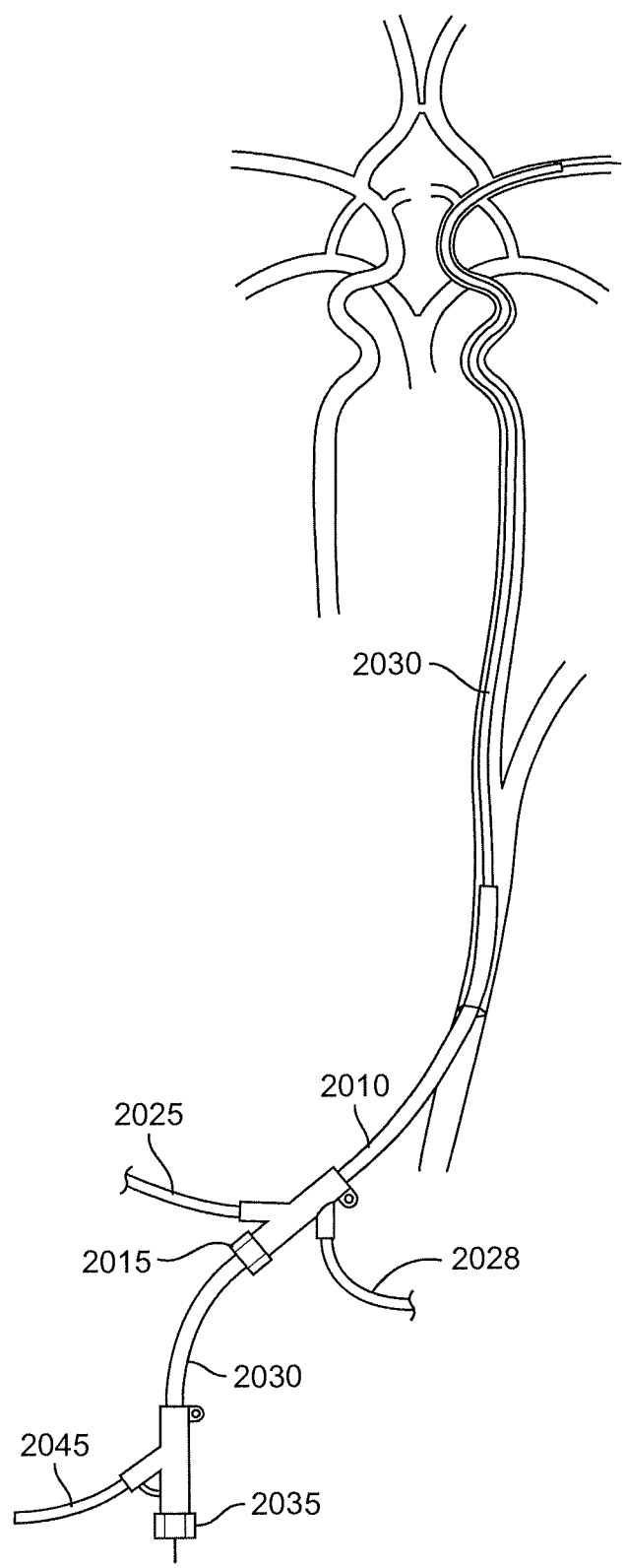
FIG. 1 illustrates an exemplary embodiment of a system of devices for transcarotid access and treatment of acute ischemic stroke showing an arterial access device inserted directly into the carotid artery and a catheter.

Interventions in the cerebral or intracranial vasculature often have special access challenges. Most neurovascular interventional procedures use a transfemoral access to the carotid or vertebral artery and thence to the target cerebral or intracranial artery. In recent years, interventional devices such as wires, guide catheters, stents and balloon catheters, have all been scaled down and been made more flexible to better perform in the neurovascular anatomy. Currently, access and treatment catheters to treat stroke range in length from 105 to 135 cm in length, with microcatheters up to 150 cm in length. These catheters access the arterial system from the femoral artery and must navigate the aortic arch and cervical and intracranial arteries to reach the occlusion in the cerebral artery. The access route is long, often tortuous and may contain stenosis plaque material in the aortic arch and carotid and brachiocephalic vessel origins, presenting a risk of embolic complications during the access portion of the procedure. In patients with tortuous anatomy, access to the occlusion may be difficult or impossible with existing catheters and devices. In addition, the cerebral vessels are usually more delicate and prone to perforation than coronary or other peripheral vasculature. Many neurovascular interventional procedures remain either more difficult or impossible because of device access challenges.

One severe drawback to current acute stroke interventions is the amount of time required to restore blood perfusion to the brain, which can be broken down to time required to access to the blocked cerebral artery, and time required to restore flow through the occlusion. Restoration of flow, either through thrombolytic therapy, mechanical thrombectomy, or other means, often takes hours during which time brain tissue is deprived of adequate oxygen. During this period, there is a risk of permanent injury to the brain tissue. In the setting of acute ischemic stroke where "time is brain," these extra difficulties have a significant clinical impact.

Another challenge of neurovascular interventions is the risk of cerebral emboli. In order to reach cerebral vessels from a transfemoral access site, catheters must traverse peripheral arteries, the aortic arch, and the carotid arteries. In many patients, there is disease in the form of atherosclerosis in these arteries. Navigating catheters across these arteries may cause fragments to break off and flow to the brain, causing cerebral emboli. Often these emboli lead to procedure-related strokes, but even sub-clinical embolic burdens to the brain have been known to lead to altered mental states.

Once a target site has been reached, there is still a risk of cerebral emboli. During the effort to remove or dissolve clot blockages in the cerebral artery, for example, there is a significant risk of thrombus fragmentation creating embolic particles which can migrate downstream and compromise cerebral perfusion, leading to neurologic events. In carotid artery stenting procedures CAS, embolic protection devices and systems are commonly used to reduce the risk of embolic material from entering the cerebral vasculature. The types of devices include intravascular filters, and reverse flow or static flow systems. Unfortunately, because of the delicate anatomy and access challenges as well as the need for rapid intervention, these embolic protection systems are not used in interventional treatment of acute ischemic stroke.

Some of the current mechanical clot retrieval procedures for stroke treatment use aspiration as a means to reduce the risk of emboli and facilitate the removal of the clot. For example, some clot retrieval procedures include attaching a large syringe to the guide catheter, and then blocking the proximal artery and aspirating the guide catheter during pull back of the clot into the guide. The guide catheter may or may not have an occlusion balloon. However, this step requires a second operator, may require an interruption of aspiration if the syringe needs to be emptied and reattached, and does not control the rate or timing of aspiration. This control may be important in cases where there is some question of patient tolerance to reverse flow. Furthermore, there is no protection against embolic debris during the initial crossing of the clot with the microcatheter and deployment of the retrieval device. Aspiration devices such as the Penumbra System utilize catheters which aspirate at the face of the clot while a separate component is sometimes additionally used to mechanically break up the clot. Aspiration methods and devices can have the potential to more rapidly restore flow and reduce the level of distal emboli, as there is no requirement to cross or disrupt the clot to remove it. However, the efficacy of aspiration with current catheter designs is limited and often requires multiple attempts and/or adjunct mechanical thrombectomy devices, thus diminishing the time and reduced distal emboli benefits.

Disclosed are methods and devices that enable safe, rapid and relatively short and straight transcarotid access to the carotid arteries and cerebral vasculature for the introduction of interventional devices for treating ischemic stroke. Transcarotid access provides a short length and non-tortuous pathway from the vascular access point to the target cerebral vascular treatment site, thereby easing the time and difficulty of the procedure, compared for example to a transfemoral approach. Additionally, this access route reduces the risk of emboli generation from navigation of diseased, angulated, or tortuous aortic arch or carotid artery anatomy. Further, this access route may make some or all aspects of the procedure faster, safer, and more accurate, as described in more detail below. The devices and associated methods include transcarotid access devices, guide catheters, catheters, and guide wires specifically to reach a cerebral target anatomy via a transcarotid access site, and associated stroke treatment devices which have been optimized for delivery through a transcarotid access site also known as a transcervical access site.

Disclosed also are methods and devices to provide aspiration and passive flow reversal either from the access sheath, a guide catheter, or a catheter for the purpose of minimizing distal emboli. Disclosed also are methods and devices that optimize clot aspiration through either transfemoral or transcarotid access approaches. Included in this disclosure are kits of various combinations of these devices to facilitate transcarotid neurovascular interventional procedures.

In another aspect, there is disclosed methods and devices for additionally providing active aspiration as well as passive retrograde flow during the procedure to minimize distal emboli. The system offers the user a degree of blood flow control so as to address the specific hemodynamic requirements of the cerebral vasculature. The system may include a flow controller, which allows the user to control the timing and mode of aspiration.

FIG. 1 shows a system of devices for accessing the common carotid artery (CCA) via a transcarotid approach and for delivering devices to the cerebral vasculature, for example an occlusion 10 in the cerebral artery. The system includes an arterial access device 2010 (sometimes referred to herein as an arterial access sheath) having an internal lumen and a port 2015. The arterial access device 2010 is sized and shaped to be inserted into the common carotid artery via a transcarotid incision or puncture and deployed into a position that provides access to the cerebral vasculature, for example the common or internal carotid artery. The port 2015 provides access to the arterial access device's internal lumen, which is configured for introducing additional devices into the cerebral vasculature via the arterial access device 2010.

FIG. 2 shows an alternate system embodiment, in which the arterial access device has an occlusion balloon 2020 that occludes the artery at the position of the sheath distal tip. As shown, the sheath is long enough to reach the distal cervical ICA from the transcarotid access site, but other embodiments may be shorter such that the occlusion balloon 2020 positioned in the CCA.

In an embodiment, transcarotid access to the common carotid artery directly with the arterial access device 2010 is achieved percutaneously via an incision or puncture in the skin. In an alternate embodiment, the arterial access device 2010 accesses the common carotid artery CCA via a direct surgical cut down to the carotid artery. In another embodiment, the arterial access device provides access to the basilar artery BA or posterior cerebral arteries PCA via a cut down incision in the vertebral artery or a percutaneous puncture of the vertebral artery for access to occlusions in the posterior cerebral vasculature such as the posterior cerebral artery or basilar artery. For entry into the common carotid artery, the arterial access device can be inserted into an opening directly in the common carotid artery, the opening being positioned above the patient's clavicle and below a bifurcation location where the patient's common carotid artery bifurcates into an internal carotid artery and external carotid artery. For example, the opening may be located at a distance of around 3 cm to 7 cm below a bifurcation location where the patient's common carotid artery bifurcates into an internal carotid artery and external carotid artery.

The system may also include an intermediate guide catheter. FIG. 3 shows a guide catheter 2105 that is inserted through an arterial access sheath 2010 via the access device proximal hemostasis valve 2012. The guide catheter 2105 includes a proximal adaptor having a proximal port 2015 with a hemostasis valve to allow introduction of devices while preventing or minimizing blood loss during the procedure. The guide catheter 2105 may also include an occlusion balloon 2020 at the distal region.

The systems shown in FIGS. 1, 2 and 3 may also include one or more catheters 2030 to provide distal access for additional devices, localized fluid or contrast delivery, or localized aspiration at a location distal of the distal-most end of the arterial access device 2010. A single catheter may be adequate for accessing and treating the occlusion or occlusions. A second, smaller diameter catheter may be inserted through the first catheter or exchanged for the first catheter if more distal access is desired and not possible with the initial catheter. In an embodiment, the catheter 2030 is sized and shaped or otherwise configured to be inserted into the internal lumen of the arterial access device 2010 via the port 2015. The catheter 2030 may use a previously placed guide wire, microcatheter, or other device acting as a guide rail and support mechanism to facilitate placement near the site of the occlusion. The catheter may also utilize a dilator element to facilitate placement through the vasculature over a guidewire. Once the catheter is positioned at or near the target site, the dilator may be removed. The catheter 2030 may then be used to apply aspiration to the occlusion. The catheter 2030 or dilator may also be used to deliver additional catheters and/or interventional devices to the site of the occlusion.

The disclosed methods and devices also include devices to protect the cerebral penumbra during the procedure to minimize injury to the brain. A distal perfusion device may be used during the procedure to provide perfusion to the brain beyond the site of the occlusion, thereby reducing the injury to the brain from lack of blood. These perfusion devices may also provide a way to reduce the forward blood pressure on the occlusion in the vessel and thus assist in removing the occlusion, for example using either aspiration, a mechanical element, or both.

The system may also include accessory devices such as guidewires and microcatheters, and stroke treatment devices such as stent retrievers, snares, or other thrombectomy devices, which have been optimally configured for reaching a target cerebral or intracranial treatment site via a transcarotid access site. For example, the system may include a thrombectomy device 4100. In addition, the disclosed methods and devices provide for securely closing the access site to the cerebral arteries to avoid the potentially devastating consequences of a transcarotid hematoma. The present disclosure provides additional methods and devices.

Exemplary Embodiments of Arterial Access Devices

Described herein are arterial access devices, also referred to herein as arterial access sheaths or sheath systems. U.S. Patent Publication No. 2014/02196769; and U.S. Provisional Application Ser. No. 62/075,169 entitled "METHODS AND DEVICES FOR TRANSCAROTID ACCESS" and filed Nov. 4, 2014; and U.S. patent application Ser. No. 14/537,316 entitled "METHODS AND DEVICES FOR TRANSCAROTID ACCESS" and filed Nov. 10, 2014 which are each incorporated by reference herein, also describe arterial access devices of consideration herein.

As described above, FIGS. 1, 2 and 3 illustrates embodiments of an arterial access sheath 2010 that is configured to be directly inserted into the common carotid artery (CCA) without use of a separate introducer sheath. The sheath 2010 can be inserted over a guidewire of an initial access system. FIG. 4 shows an embodiment of a transcarotid initial access system 100 or a micro access kit for establishing initial access to a carotid artery for the purpose of enabling introduction of a guide wire into the carotid artery. The access to the carotid artery can occur at an access site located in the neck of a patient such as in the region of the patient's carotid artery. The devices of the transcarotid initial access system 100 are particularly suited for directly accessing the carotid artery through the wall of the common carotid artery. The transcarotid initial access system 100 can include an access needle 120, access guidewire 140, and micropuncture cannula 160. The micropuncture cannula 160 can include a cannula body 162 and an inner dilator 168 slidably positioned within a lumen of the body 162. The inner dilator 168 can have a tapered tip and provide a smooth transition between the cannula and the access guidewire 140. The micropuncture cannula 160 can also include a radiopaque marker 164 near a distal tip of the cannula 160 to help the user visualize the tip location under fluoroscopy. The access guidewire 140 can include guide wire markings 143 to help the user determine where the tip of the guide wire 140 is with respect to the cannula 160. The access needle 120, access guidewire 140, and micropuncture cannula 160 are all adapted to be introduced via a carotid puncture into the carotid artery. The carotid puncture may be accomplished, for example, percutaneously or via a surgical cut down. Embodiments of the initial access system 100 may be adapted towards one or the other method of puncture.

In an alternate embodiment, the arterial access device 2010 may be configured for access to the common carotid artery CCA from a femoral artery access site, also without the use of a separate introducer sheath. As above, the access device includes a proximal adaptor with a proximal port 2015 with a hemostasis valve and a connection to a flow line 2025 (or shunt) which may be connected to means for passive or active reverse flow. The flow line 2025 has an internal lumen that communicates with an internal lumen of the arterial access device 2010 for shunting blood from the arterial access device. In both transfemoral and transcarotid embodiments, the connection to the flow line is optimized for aspiration of thrombus with flow lumens at least as large as the ID of the arterial access device 2010.

Figure 5:
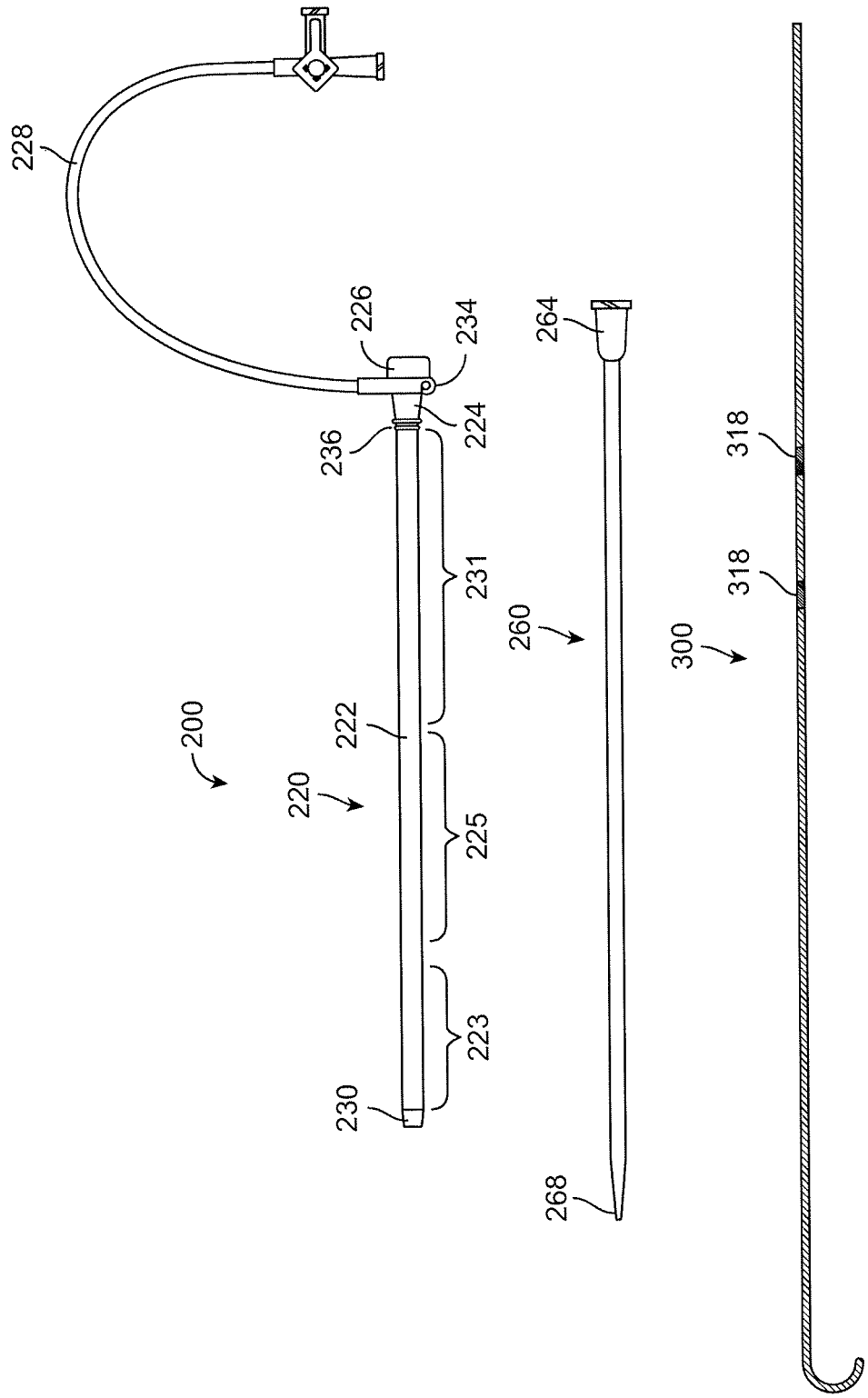
FIG. 5 shows an embodiment of a transcarotid access sheath system.

Upon establishment of access to the carotid artery using the initial access system 100, an arterial access sheath of a sheath system such as those described herein may be inserted into the carotid artery at the access site. FIG. 5 shows an embodiment of a transcarotid access sheath system 200 of devices for inserting an access sheath into the carotid artery, for example, over a sheath guidewire of an initial access system. When inserted into the carotid artery, the access sheath system 200 allows for the introduction of at least one interventional device into the carotid artery via a lumen of the access sheath for the purpose of performing an interventional procedure on a region of the vasculature. The transcarotid access sheath system 200 can include an access sheath 220, a sheath dilator 260, and a sheath guidewire 300. The access sheath 220, sheath dilator 260 and sheath guidewire 300 are all adapted to be introduced via a carotid puncture into the carotid artery. The carotid puncture may be accomplished percutaneously or via a surgical cut down. Embodiments of the access sheath system 200 may be adapted towards one or the other method of puncture.

In an embodiment, some or all of the components of transcarotid initial access system 100 and the transcarotid access sheath system 200 may be combined into one transcarotid access system kit such as by combining the components into a single, package, container or a collection of containers that are bundled together.

Figure 6:
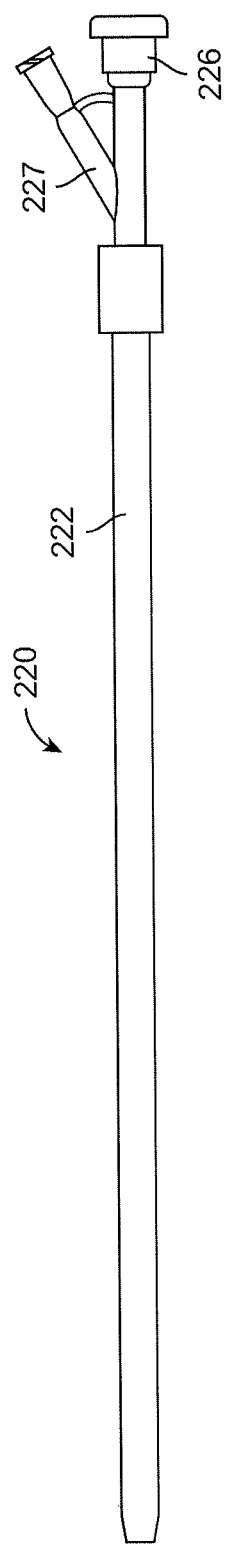

The arterial access sheath systems described herein can include a distal portion configured to be inserted in the vessel and a proximal portion configured to extend outward from the access site when the distal portion of the arterial access sheath is positioned in the arterial pathway. For example with reference to FIG. 5, the arterial access sheath 220 has an elongated sheath body 222 sized and shaped such that at least a portion of the sheath body 222 is insertable into the artery during a procedure while the proximal portion remains outside the body. The elongated sheath body 222 is the portion of the arterial access sheath 220 that is sized and shaped to be inserted into the artery and wherein at least a portion of the elongated sheath body is actually inserted into the artery during a procedure. A proximal adaptor 224 can be positioned near a proximal end of an elongated sheath body 222 (see also, e.g. port 2015 of FIG. 1). The proximal adaptor 224 is configured to remain outside the body when at least a portion of the sheath body 222 is inserted into the artery. The proximal adaptor 224 can have a hemostasis valve 226 that communicates with the internal lumen of the sheath body 222. The hemostasis valve 226 that communicates with the internal lumen of the sheath body 222 allow for the introduction of devices therein while preventing or minimizing blood loss via the internal lumen during the procedure. The hemostasis valve 226 can be a static seal-type passive valve, or an adjustable-opening valve such as a Tuohy-Borst valve 227 or rotating hemostasis valve (RHV) (see FIG. 6). The hemostasis valve may be integral to the proximal adaptor 224, or the access sheath 220 may terminate on the proximal end in a female Luer adaptor to which a separate hemostasis valve component, such as a passive seal valve, a Tuohy-Borst valve or rotating hemostasis valve, may be attached. Further, one or more features can be positioned near the proximal end of the access sheath 220 to aid in securement of the sheath during the procedure. For example, the access sheath 220 may have a suture eyelet 234 or one or more ribs 236 molded into or otherwise attached to the adaptor 224, which would allow the operator to suture tie the sheath hub to the patient.

In an embodiment, the sheath body 222 can have an inner diameter of about 0.087" and an outer diameter of about 0.104", corresponding to a 6 French sheath size. In another embodiment, the sheath body 222 has an inner diameter of about 0.113" and an outer diameter of about 0.136", corresponding to an 8 French sheath size. In an embodiment, the sheath length is between 10 and 12 cm. In another embodiment, the sheath length is between 15 and 30 cm. The diameter and length most suitable to a particular embodiment is dependent on the location of the target site and nature of the devices and flow requirements through the lumen of the access device 200.

In some instances it is desirable to move the proximal port and/or the hemostasis valve away from the distal tip of the arterial access sheath effectively elongating or lengthening the proximal portion (also called a proximal extension herein) that is outside the body while maintaining the length of the insertable distal portion. This allows the user to insert devices into the proximal port of the proximal extension and from there into the lumen of the arterial access device from a point further away from the target site and from the image intensifier used to image the target site fluoroscopically thereby minimizing radiation exposure of the user's hands and also his or her entire body. The proximal extension can be configured such that the length between the proximal port and the arterial access site is between about 30 cm and about 50 cm. The proximal extension can be removable from the arterial access device. An example of a proximal extension design is described in co-pending U.S. Application Publication No. 2010/0042118, filed Aug. 12, 2009, which is incorporated herein by reference. U.S. Pat. No. 8,574,245, U.S. Application Publication No. 2010/0217276, and U.S. Application Publication No. 2011/0087147, which each are also incorporated by reference herein.

FIG. 10 also illustrates an embodiment of an arterial access sheath 220 having a proximal extension portion 805. The proximal extension 805 can have a length suitable to meaningfully reduce the radiation exposure to the user during a transcarotid access procedure. For example, the proximal extension 805 is between about 10 cm and about 25 cm, or between about 15 cm and about 20 cm. Alternately, the proximal extension 805 has a length configured to provide a distance of between about 30 cm and about 60 cm between the hemostasis valve 226 and the distal tip of the sheath body, depending on the insertable length of the access sheath. A connector structure 815 can connect the elongated sheath body 222 to the proximal extension 805. In this embodiment, the connector structure 815 may include a suture eyelet 820 and/or ribs 825 to assist in securing the access sheath 220 to the patient. In an embodiment, the hemostasis valve 226 is a static seal-type passive valve. In an alternate embodiment the hemostasis valve 226 is an adjustable-opening valve such as a Tuohy-Borst valve 227 or rotating hemostasis valve (RHV). Alternately, the proximal extension 805 may terminate on the proximal end in a female Luer adaptor to which a separate hemostasis valve component may be attached, either a passive seal valve, a Tuohy-Borst valve or rotating hemostasis valve (RHV).

The proximal extension and/or proximal adaptor 224 can have a larger inner and outer diameter than the sheath body 222 or the portion of the access sheath configured to be inserted arterially. In instances where the outer diameter of the catheter being inserted into the sheath is close to the inner diameter of the sheath body, the annular space of the lumen that is available for flow is restrictive. Minimizing the sheath body length is thus advantageous to minimize this resistance to flow, such as during flushing of the sheath with saline or contrast solution, or during aspiration or reverse flow out of the sheath. Again with respect to FIG. 10, the sheath body 222 can have an inner diameter of about 0.087" and an outer diameter of about 0.104", corresponding to a 6 French sheath size, and the proximal extension has an inner diameter of about 0.100" to about 0.125" and an outer diameter of about 0.150" to about 0.175". In another embodiment, the sheath body 222 has an inner diameter of about 0.113" and an outer diameter of about 0.136", corresponding to an 8 French sheath size, and the proximal extension has an inner diameter of about 0.125" and an outer diameter of about 0.175". In yet another embodiment, the sheath body 222 is stepped with a smaller diameter distal section 605 to further reduce flow restriction, as in FIG. 8.

The proximal extension 905 on the arterial access sheath 220 may be removable. Typically, vessel closure devices requires an arterial access sheath with a maximum distance of about 15 cm between distal tip of the sheath body to the proximal aspect of the hemostasis valve, with sheath body of about 11 cm and the remaining 4 cm comprising the length of the proximal hemostasis valve; thus if the access sheath has a distance of greater than 15 cm it is desirable to remove the proximal extension at the end of the procedure. Again with respect to FIG. 10, the proximal extension 805 can be removable in such a way that after removal, hemostasis is maintained. For example, a hemostasis valve is built into the connector 815 between the sheath body 222 and the proximal extension 805. The hemostasis valve can be opened when the proximal extension 805 is attached to allow fluid communication and insertion of devices, but prevents blood flowing out of the sheath 220 when the proximal extension 805 is removed. After the procedure is completed, the proximal extension 805 can be removed, reducing the distance between the proximal aspect of the hemostasis valve and sheath tip from greater than 15 cm to equal or less than 15 cm and thus allowing a vessel closure device to be used with the access sheath 220 to close the access site.

The arterial access sheath systems described herein are suitable or particularly optimized to provide transcarotid arterial access for reaching various treatment sites from that access site. The working length of the arterial access sheath or sheath/guide catheter system described herein can be considerably shorter than that of long sheaths or sheath guide systems placed, for example, from an access location in the femoral artery. The distance from the femoral artery to the common carotid artery (CCA) is about 60-80 cm moving through the artery. Thus, arterial access devices using a CCA access site may be shorter by at least this amount. Femoral arterial access used to access or deploy a device in the cervical ICA (e.g. the Balloon Guide, Concentric, Inc.) are typically 80-95 cm in length. Femoral arterial access used to access or deploy a device in the petrous ICA (e.g. the Neuron 6F Guide, Penumbra, Inc.) are typically 95-105 cm in length. The shorter lengths of access devices disclosed herein reduces the resistance to flow through the lumen of these devices and increases the rate at which aspiration and/or reverse flow may occur. For example, in an embodiment, the elongated sheath body 222 has a length in the range of about 10 cm to about 12 cm. For access to a same target site from a femoral access site, the access sheaths are typically between 80 cm and 110 cm, or a guide catheter is inserted through an arterial access sheath and advanced to the target site. However, a guide catheter through an access sheath takes up luminal area and thus restricts the size of devices that may be introduced to the target site. Thus, an access sheath that allows interventional devices to reach a target site without a guide catheter has advantages over an access sheath that requires use of a guide catheter to allow interventional devices to the target site.

It should be appreciated that the length and inner diameter of the arterial access sheaths described herein can vary depending on the desired target position of the sheath distal tip. In one embodiment, an access sheath is adapted to be inserted into the common carotid artery (CCA) with the distal tip positioned in the CCA or proximal ICA. In this embodiment, the sheath can have an elongated sheath body 222 having a length in the range of from about 7 cm to about 15 cm, usually being from about 10 cm to about 12 cm. The length considered herein can be the length extending from the proximal adapter 224 to a distal tip of the elongated sheath body 222. For a sheath adapted to be inserted via the common carotid artery (CCA) to a more distal site in the mid or distal internal carotid artery the length of the elongated sheath body 222 can be in the range from about 10 cm to about 30 cm, usually being from about 15 cm to about 25 cm. In another example embodiment, the arterial access device has a length of about 10 cm to about 40 cm. In another embodiment, the length of the arterial access device is about 10.5 cm and a separate guide catheter inserted through the access device has a length of about 32 cm.

Figure 8:
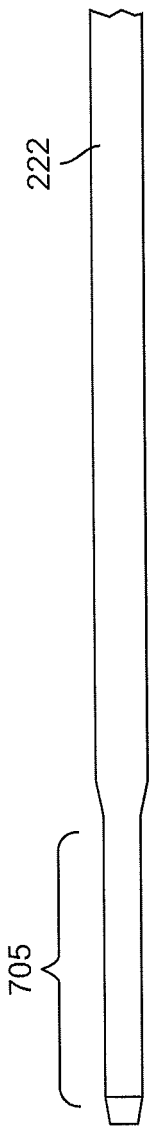

In some procedures it may be desirable to incorporate features on the arterial access sheath in order to minimize flow resistance through the insertable portion of the access sheath, for example, as described in U.S. Pat. No. 7,998,104 to Chang and U.S. Pat. No. 8,157,760 to Criado, which are both incorporated by reference herein. For example, FIG. 8 shows such an embodiment of the sheath body 222 having a stepped or tapered configuration such that the sheath body 222 has a reduced diameter distal region 705 (with the reduced diameter being relative to the remainder of the sheath). The distal region 705 of the stepped sheath can be sized for insertion into the carotid artery. The inner diameter of the distal region 705 can be in the range from 0.065 inch to 0.115 inch with the remaining proximal region of the sheath having larger outside and luminal diameters. The inner diameter of the remaining proximal region can typically be in the range from 0.110 inch to 0.135 inch. The larger luminal diameter of the remainder of the sheath body 222 minimizes the overall flow resistance through the sheath 220. In an embodiment, the reduced-diameter distal region 705 has a length of approximately 2 cm to 4 cm. The relatively short length of the reduced-diameter distal region 705 permits this section to be positioned in the common carotid artery CCA via a transcarotid approach with reduced risk that the distal end of the sheath body 222 will contact the bifurcation. In an alternate embodiment, the sheath body is configured to have an insertable portion that is designed to reach as far as the distal ICA. In this embodiment, the reduced-diameter distal section 605 has a length of approximately 10 cm to 15 cm, with a total sheath body length of 15-25 cm. The reduced diameter section permits a reduction in size of the arteriotomy for introducing the sheath into the artery while having a minimal impact in the level of flow resistance. Further, the reduced distal diameter region 705 may be more flexible and thus more conformal to the lumen of the vessel.

Figure 11:
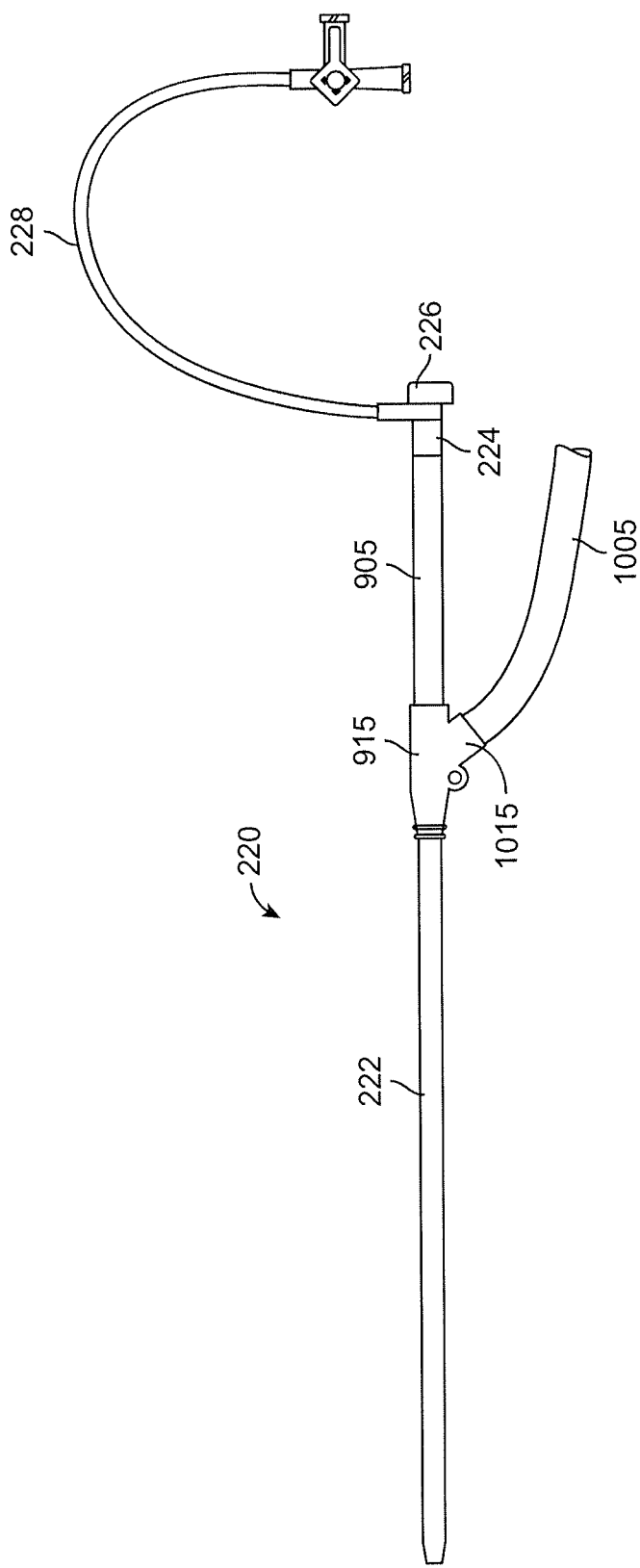

In some instances it may be desirable to connect the access sheath to a flow line, for example for the purposes of passive or active aspiration to reduce the risk of distal emboli during the procedure. In an embodiment shown in FIG. 11, the arterial access sheath 220 has a low resistance (large bore) flow line or shunt connected to the access sheath. The low resistance flow line 905 can be connected to an internal lumen of the sheath body 222 via a Y-arm 915 of the connector 815. The flow line 905 may be connected to a lower pressure return site such as a venous return site or a reservoir. The flow line 905 may also be connected to an aspiration source such as a pump or a syringe. As shown in FIG. 11, the flow line 905 can be located distal of the location where devices enter the proximal port 226 of the arterial access sheath 220. In an alternate embodiment, the flow line 905 is attached to the Y-arm of a separately attached Tuohy Borst valve.

The flow line can be connected to an element configured for passive and/or active reverse flow such that blood from the arterial access sheath can be shunted. Connecting the flow line to a lower pressure system, such as a central vein or a reservoir, is an example of passive reverse flow. The reservoir may be positioned on a table near the patient, for a pressure of approximately zero, or positioned below the table to create negative pressure. Examples of devices for active reverse flow are a syringe or other manual aspiration device, or an aspiration pump. The passive or active reverse flow device may be actuated via a stopcock or other flow control switch during critical periods of the procedure, for example when thrombus is being pulled out of the occluded area, into the sheath, and out of the patient. In an embodiment, the flow control switch is integral to the arterial access device. In an alternate embodiment, the flow control switch is a separate component. Because it may be desirable to remove all thrombus from the device with minimal to no chance of material being caught in irregular surfaces or connection surfaces, an embodiment of the access device is constructed such that there is a continuous inner surface with no ledges or crevices at the junction(s) between the lumen of the sheath body, the Y-arm, the flow control switch, the flow line, and the aspiration source.

In some instances it is desirable for the sheath body to also be able to occlude the artery in which it is positioned, for examples in procedures that may create distal emboli. In these cases, occluding the artery stops antegrade blood flow in the artery and thereby reduces the risk of distal emboli that may lead to neurologic symptoms such as TIA or stroke. The arterial access device 2010 of FIG. 1 or FIG. 2 may have an occlusion balloon 2020 configured to occlude the artery when inflated. In turn, the arterial access device 2010 may also include a lumen for balloon inflation. This lumen fluidly connects the balloon, for example, to a second Y-arm on the proximal adaptor. This Y-arm is attached to a tubing 2028 which terminates in a one-way stopcock 2029. An inflation device such as a syringe may be attached to the stopcock 2029 to inflate the balloon when vascular occlusion is desired. FIG. 9 shows an embodiment of an arterial access sheath 220 with an inflatable balloon 705 on a distal region that is inflated via an inflation line 710 that connects an internal inflation lumen in the sheath body 222 to a stopcock 229, which in turn may be connected to an inflation device. In this embodiment, there is also a Y-arm 715 that may be connected to a passive or active aspiration source to further reduce the risk of distal emboli.

In some configurations, an intermediate guide catheter may be inserted through the arterial access device to provide additional catheter support and potentially distal occlusion. FIG. 3 shows a system with a guide catheter 2105 inserted into the CCA through the proximal hemostasis valve 2012 of the arterial access device 2010. The guide catheter 2105 includes a proximal adaptor having a proximal port 2015 with a hemostasis valve to allow introduction of devices while preventing or minimizing blood loss during the procedure. The guide catheter 2105 may also include an occlusion balloon 2020 and a lumen for balloon inflation that is attached to a Y-arm in the proximal adaptor, which in turn is connected to a tubing 2128. The tubing 2128 terminates in a one-way stopcock 2129 for connection to a balloon inflation device. The guide catheter 2105 may include a second Y-arm 2107 that communicates with a flow line 2125. Introduction through the separate sheath 2110 allows removal of the guide catheter 2105 for flushing outside the patient and reinserting, or for exchanging the guide catheter 2105 with another guide catheter without removing the introducer sheath 2110, thus maintaining access to the artery via the transcarotid incision. This configuration also allows repositioning of the occlusion balloon 2020 during the procedure without disturbing the arterial insertion site. The embodiment of FIG. 11 also allows removal of the arterial access device 2105 and then insertion of a vessel closure device through the introducer sheath 2110 at the conclusion of the procedure.

Figure 12:
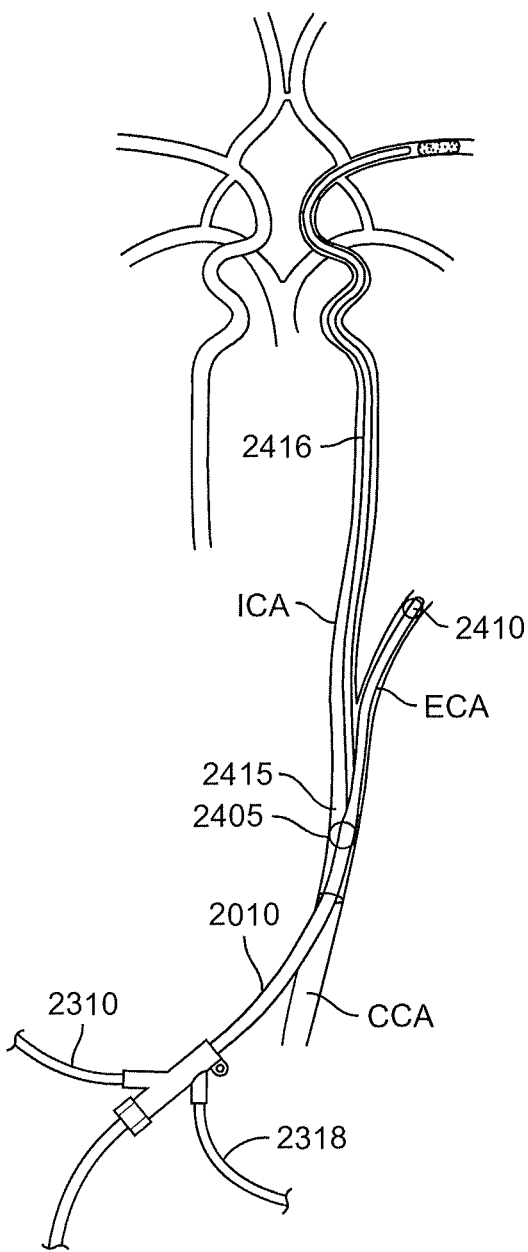
FIG. 12 shows an embodiment of an arterial access device which has two occlusion balloons and an opening between the two balloons

In yet another embodiment, as shown in FIG. 12, the arterial access device is a device 2010 with two occlusion balloons 2405 and 2410 and a side opening 2415 positioned between the two balloons. The distal occlusion balloon 2410 is located at or near the distal end of the arterial access device 2010, and the proximal occlusion balloon 2405 is located between the distal end and the proximal end of the working portion of the arterial access device. The distal occlusion balloon 2410 is sized and shaped to be placed in the external carotid artery ECA and the proximal occlusion balloon 2405 is sized and shaped to be placed in the common carotid artery CCA. Such a dual balloon configuration stops flow into the internal carotid artery ICA from both the CCA and the ECA, which has an effect functionally the same as an occlusion balloon positioned in the ICA without inserting a device into the ICA. This may be advantageous if the ICA were diseased, whereby access may cause emboli to dislodge and create embolic complications, or the access to the ICA were severely tortuous and difficult to achieve, or both. The side opening 2415 in the working section of the arterial access device 2105 permits a device 2416 to be introduced via the arterial access device 2010 and inserted into the ICA via the side opening 2415 while flow is stopped or reversed, to reduce or eliminate the risk of distal emboli. This device 2416 may then be advanced to the location of the cerebral artery occlusion to treat the occlusion.

Figure 13:
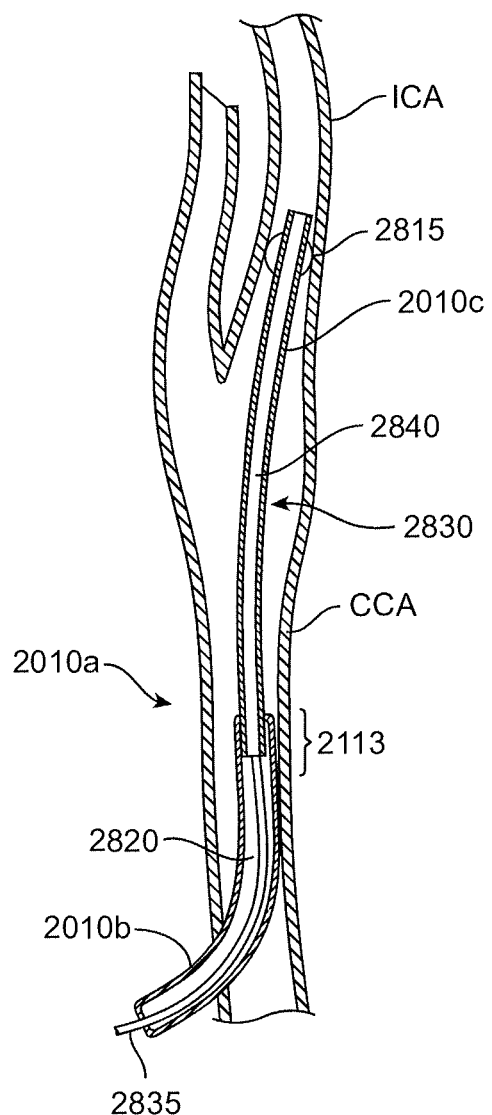
FIG. 13 shows an embodiment of a telescoping arterial access device.

In yet another embodiment, as shown in FIG. 13 the arterial access device is a multi-part (such as two-part) telescoping system. The access sheath 2010b and/or the distal extension 2010c can be formed of two or more concentric, tubular sections that telescopically slide relative to one another to increase and/or decrease the entire collective length of the movably attached tubular sections. The first part is an access sheath 2010b that is configured to be inserted directly into the CCA. The second part is a distal extension 2010c which is inserted through the proximal end of the introducer sheath 2010b and which extends the reach of the sheath into the ICA. The distal end of the sheath 2010b and the proximal end of the extension 2010c form a lap junction 2113 when the extension is fully inserted, such that there is a continuous lumen through the two devices. The lap junction may be variable length, such that there is some variability in the length of the combined telescoping system 2105b. The distal extension 2010c can include a tether which allows placement and retrieval of the distal extension 2010c through the sheath 2010b. In an embodiment, the distal extension 2010c includes an occlusion balloon 2815. In this embodiment the tether 2835 include a lumen for inflation of the balloon. This tether can be connected on the proximal end to a balloon inflation device. This configuration provides the advantages of sheath plus guide catheter system shown in FIG. 3, without compromising the luminal area.

The arterial access devices described herein may be configured so that it can be passed through or navigate bends in the artery without kinking. For example, when the access sheath is being introduced through the transcarotid approach, above the clavicle but below the carotid bifurcation, it is desirable that the elongated sheath body 222 be flexible while retaining hoop strength to resist kinking or buckling. This can be especially important in procedures that have limited amount of sheath insertion into the artery and/or where there is a steep angle of insertion as with a transcarotid access in a patient with a deep carotid artery and/or with a short neck. In these instances, there is a tendency for the sheath body tip to be directed towards the back wall of the artery due to the stiffness of the sheath. This causes a risk of injury from insertion of the sheath body itself, or from devices being inserted through the sheath into the arteries, such as guide wires. Alternately, the distal region of the sheath body may be placed in a distal carotid artery which includes one or more bends, such as the petrous ICA. Thus, it is desirable to construct the sheath body 222 such that it can be flexed when inserted in the artery, while not kinking. In an embodiment, the arterial access device can be and is passed through bends of less than or equal to 45 degrees wherein the bends are located within 5 cm, 10 cm, or 15 cm of the arteriotomy measured through the artery.

The working portion of the arterial access sheath, such as the sheath body which enters the artery, can be constructed in two or more layers. An inner liner can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liner and may be constructed from materials such as Pebax, thermoplastic polyurethane, polyethylene, nylon, or the like. A third layer can be incorporated that can provide reinforcement between the inner liner and the outer jacket. The reinforcement layer can prevent flattening or kinking of the inner lumen of the sheath body as the device navigates through bends in the vasculature. The reinforcement layer can also provide for unimpeded lumens for device access as well as aspiration or reverse flow. In an embodiment, the sheath body 222 is circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut so as to be flexible. In another embodiment, the reinforcement layer can be a cut hypotube such as a Nitinol hypotube or cut rigid polymer, or the like.

The arterial access sheaths described herein can have a sheath body that varies in flexibility over its length. As described above, a distal-most portion of the arterial access device may be configured to be more flexible than a proximal section of the device. In one embodiment, there is a distal-most section of sheath body 222 that is more flexible than the remainder of the sheath body. The distal section may be at least 10% of the length of the working portion of the catheter wherein the working portion is the portion that is configured to be inserted into an artery. In other embodiments, the distal section is at least 20% or at least 30% of the length of the working portion of the catheter. The variability in flexibility may be achieved in various ways. For example, the outer jacket may change in durometer and/or material at various sections. A lower durometer outer jacket material can be used in a distal section of the sheath compared to other sections of the sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the sheath body. For example, the flexural stiffness of the distal-most section can be one third to one tenth the flexural stiffness of the remainder of the sheath body 222. In an embodiment, the distal-most section has a flexural stiffness (E*I) in the range 50 to 300 N-mm$^2$ and the remaining portion of the sheath body 222 has a flexural stiffness in the range 500 to 1500 N-mm$^2$, where E is the elastic modulus and I is the area moment of inertia of the device. For a sheath configured for a CCA access site, the flexible, distal most section comprises a significant portion of the sheath body 222 which may be expressed as a ratio. In an embodiment, the ratio of length of the flexible, distal-most section to the overall length of the sheath body 222 is at least one tenth and at most one half the length of the entire sheath body 222.

In some instances, the arterial access sheath is configured to access a carotid artery bifurcation or proximal internal carotid artery ICA from a CCA access site. As best shown in FIG. 5, the sheath body 222 can have a distal-most section 223 which is about 3 cm to about 4 cm and the overall sheath body 222 is about 10 cm to about 12 cm. In this embodiment, the ratio of length of the flexible, distal-most section to the overall length of the sheath body 222 is about one forth to one half the overall length of the sheath body 222. In another embodiment, there is a transition section 225 between the distal-most flexible section and the proximal section 231, with one or more sections of varying flexibilities between the distal-most section and the remainder of the sheath body. In this embodiment, the distal-most section is about 2 cm to about 4 cm, the transition section is about 1 cm to about 2 cm and the overall sheath body 222 is about 10 cm to about 12 cm, or expressed as a ratio, the distal-most flexible section and the transition section collectively form at least one fourth and at most one half the entire length of the sheath body.

In some instances, the sheath body 222 of the arterial access sheath is configured to be inserted more distally into the internal carotid artery relative to the arterial access location, and possibly into the intracranial section of the internal carotid artery. For example, a distal-most section 223 of the elongated sheath body 222 is about 2.5 cm to about 5 cm and the overall sheath body 222 is about 15 cm to about 30 cm in length. In this embodiment, the ratio of length of the flexible, distal-most section to the overall length of the sheath body is one tenth to one quarter of the entire sheath body 222. In another embodiment, there is a transition section 225 between the distal-most flexible section and the proximal section 231, in which the distal-most section is about 2.5 cm to about 5 cm, the transition section is about 2 cm to about 10 cm and the overall sheath body 222 is about 15 cm to about 30 cm. In this embodiment, the distal-most flexible section and the transition section collectively form at least one sixth and at most one half the entire length of the sheath body.

In some instances it is desirable to keep the sheath tip as small as possible during sheath insertion to minimize the diameter of the arterial puncture, but to expand the opening of the sheath after it has been inserted into the vessel. At least one purpose of this feature is to minimize the effect or creation of distal emboli during pull back of an aspiration catheter or other thrombectomy device into the sheath. During a thrombectomy procedure, the thrombus may be "pulled back" into a distal opening of the sheath on a device that has captured the thrombus. If the distal tip of the sheath is enlarged relative to its initial size, the chance of pieces of the thrombus breaking off and causing emboli is minimized because the larger size of the sheath tip is more likely to accommodate the emboli being drawn into it without being split into multiple pieces. This creates a better clinical outcome for the patient. In an embodiment of the arterial access device, the arterial access device is made of a material and/or constructed such that a tip of the sheath body of the access device can be expanded to a larger diameter once inserted into the artery and positioned in its desired location. In an embodiment, the distal region of the sheath has an ID of about 0.087" can be enlarged to a diameter of about 0.100" to 0.120" although the size may vary.

Examples of expanding distal tip constructions include covered braided tips that can be shortened to expand. Another example of an expanding distal tip construction is an umbrella or similar construction that can open up with mechanical actuation or elastic spring force when unconstrained. Other mechanisms of expandable diameter tubes are well known in the art. One particular embodiment is a sheath made of material that is deformable when expanded using a high pressure balloon.

Figure 15:
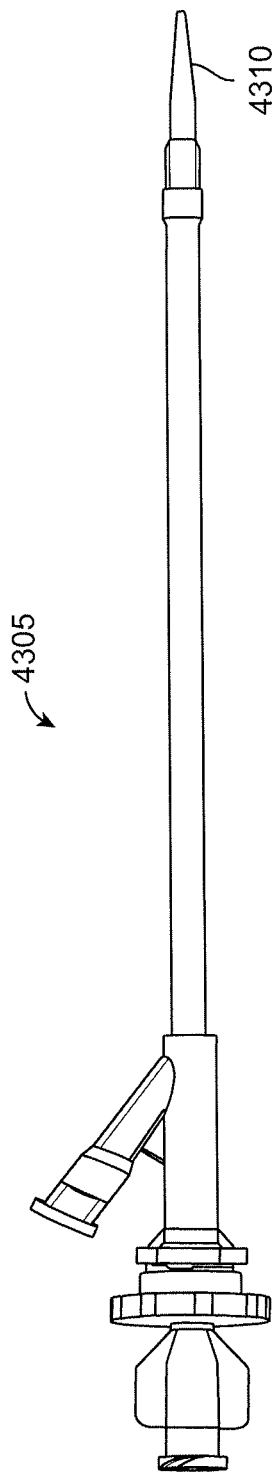
FIG. 15-18 shows an example of an arterial access device comprised of a sheath that has an expandable distal tip.
Figure 16:
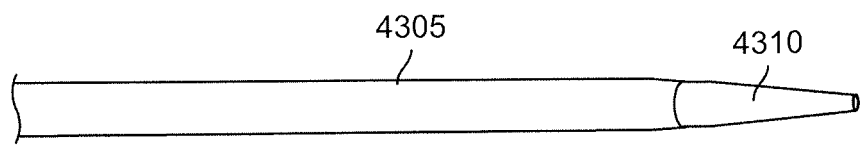
Figure 17:
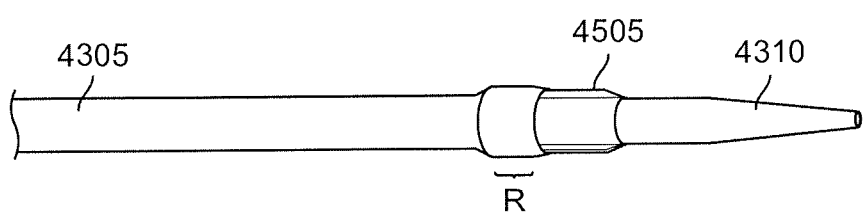
Figure 18:
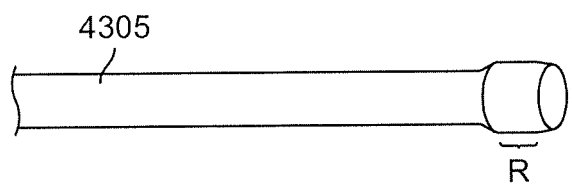

FIG. 15 shows an example of an arterial access device comprised of a sheath 4305 that has an expandable distal tip. As in other embodiments, the sheath 4305 has an internal lumen sized and shaped to receive a dilator 4310, which is shown protruding out of the distal end of the sheath 4305. The proximal region of the sheath 4305 may be equipped with any of a variety of Y-arms, valves, actuators, etc. FIG. 16 shows an enlarged view of the distal region of the sheath 4305 with the dilator 4310 protruding outward. In the view of FIG. 16, the distal region of the sheath is unexpanded. The dilator 4310 is equipped with an expandable balloon 4505 that may be aligned at a desired location along the sheath 4305 by sliding the dilator 4310 forward or backward relative to the sheath 4305. The dilator may have an inflation lumen and inflation device for inflating the balloon 4505. When the dilator 4310 is inserted into the arterial access device sheath 4305, the balloon 4405 can be aligned at a desired location of the sheath 4305. When the balloon 4505 is inflated, a precise length or region of the sheath 4305 is expanded to a precise diameter as a result of the balloon 4505 expanding inside the sheath. Once the sheath tip is in its desired location, the balloon is inflated to a pressure that would expand the sheath, as shown in FIG. 17 where a distal region R of the sheath body has been expanded. FIG. 18 shows the sheath 4305 with the region R expanded as a result of the balloon 4505 being expanded while inside the sheath 4305. In an embodiment, the distal region R is plastically expanded. The sheath body is constructed such that it could stretch to this larger diameter without tearing or breaking. The balloon material may be a non-compliant or semi-compliant material similar or identical to those used in angioplasty balloons, such as nylon. These materials may be inflated to a very high pressure without expanding past the engineered diameter. In a variation, the balloon inflation member is separate from the dilator or on a second dilator, and exchanged for the initial dilator used for sheath insertion, once the sheath is in its desired location. The expanding tip design may be used in place of or in conjunction with an occluding balloon on the sheath to minimize the risk of distal emboli.

Figure 7:
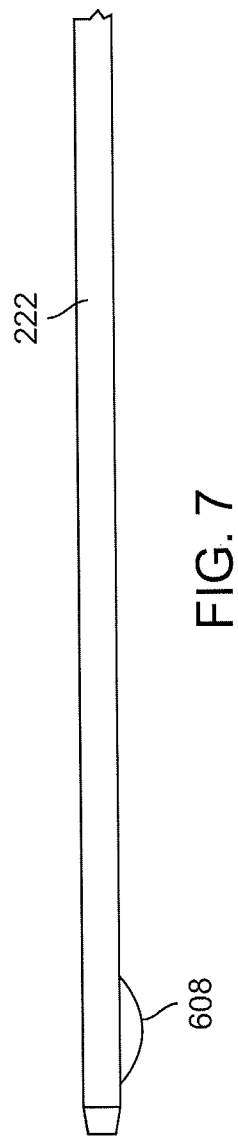

The arterial access devices described herein can also be adapted to reduce, minimize or eliminate a risk of injury to the artery caused by the distal-most sheath tip facing and contacting the posterior arterial wall. In some embodiments, the sheath has a structure configured to center the sheath body tip in the lumen of the artery such that the longitudinal axis of the distal region of the sheath body is generally parallel with the longitudinal or center axis of the lumen of the vessel. The sheath alignment feature 508 can be one or more mechanical structures on the sheath body 222 that can be actuated to extend outward from the sheath tip (see FIG. 7). The sheath alignment feature 508 can be an inflatable, enlargeable, extendible bumper, blister, or balloon, located on an outer wall of the arterial access sheath 220. The sheath alignment feature 508 may be increased in size to exert a force on the inner arterial wall to contact and push the elongated body 222 of the arterial access sheath away from the arterial wall. In an embodiment, the sheath body 222 is configured to be inserted into the artery such that a particular edge of the arterial access is against the posterior wall of the artery. In this embodiment, the sheath alignment feature 508 can extend outward from one direction relative to the longitudinal axis of the sheath body 222 to lift or push the sheath tip away from the posterior arterial wall. The alignment feature 508 can be positioned on one side of the sheath body 222 as shown in FIG. 7 or on more than one side of the sheath body 222.

In another embodiment, at least a portion of the sheath body 222 is pre-shaped so that after sheath insertion the tip is more aligned with a long axis of the vessel within which it is inserted, even at a steep sheath insertion angle. In this embodiment, the sheath body 222 is generally straight when the dilator 260 is assembled with the sheath 220 during sheath insertion over the sheath guide wire 300, but once the dilator 260 and guidewire 300 are removed, the distal-most section of the sheath body 222 can assume a curved or angled shape. In an embodiment, the sheath body 222 is shaped such that the distal-most 0.5 cm to 1 cm section is angled from 10 to 30 degrees, as measured from the main axis of the sheath body 220, with a radius of curvature about 0.5". To retain the curved or angled shape of the sheath body 220 after having been straightened during insertion, the sheath 220 may be heat set in the angled or curved shape during manufacture. Alternately, a reinforcement structure may be constructed out of nitinol and heat-shaped into the curved or angled shape during manufacture. Alternately, an additional spring element may be added to the sheath body 220, for example a strip of spring steel or nitinol, with the correct shape, added to the reinforcement layer of the sheath 220.

In some procedures, it may be desirable to limit the amount of sheath body 222 insertion into the artery, for example in procedures where the target area is very close to the arterial access site. In a stent procedure of the carotid artery bifurcation, for example, the sheath tip should be positioned proximal of the treatment site (relative to the access location) so that it does not interfere with stent deployment or enter the diseased area and possibly cause emboli to get knocked loose. In an embodiment of arterial sheath 220 shown in FIGS. 14A and 14B, a sheath stopper 1005 is slideably connected or mounted over the outside of the distal portion of the sheath body. The sheath stopper 1005 is shorter than the distal portion of the sheath, effectively shortening the insertable portion of the sheath body 222 by creating a positive stop at a certain length along the sheath body 222. The sheath stopper 1005 may be a tube that slidably fits over the sheath body 222 with a length that, when positioned on the sheath body 222, leaves a distal portion of the sheath body exposed. This length can be in the range about 2 cm to about 4 cm. More particularly, the length is about 2.5 cm. The distal end of the sheath stopper 1005 may be angled and oriented such that the angle sits flush with the vessel and serves as a stop against the arterial wall when the sheath is inserted into the artery when the vessel is inserted into the artery, as shown in FIG. 14A. Alternately, the distal end of the sheath stopper may be formed into an angled flange 1015 that contacts the arterial wall, as shown in FIG. 14B. The flange 1015 is rounded or has an atraumatic shape to create a more positive and atraumatic stop against the arterial wall. The sheath stopper 1005 may be permanently secured to the arterial sheath, for example the proximal end of the sheath stopper may be adhered to connector 815 of the arterial access sheath. Alternatively, the sheath stopper 1005 may be removable from the arterial access sheath 220 by the user so it can be optionally utilized in a procedure. In this instance, the sheath stopper 1005 may have a locking feature on the proximal portion that engages with a corresponding locking features on the connector 815, for example slots or recesses on the proximal sheath stopper engaging protrusions on the connector. Other locking features may also be utilized.

In situations where the insertion of the sheath body is limited to between about 2 cm and about 3 cm, and particularly when the sheath body 222 is inserted at a steep angle, the sheath 220 may conform to a bayonet shape when secured to the patient. For example, the bayonet shape may comprise a first portion that extends along a first axis and a second portion that extends along a second axis that is axially offset from the first axis and/or non-parallel to the first axis. The springiness of the sheath body 222 causes this shape to exert a force on the vessel at the site of insertion and increase the tendency of the sheath 220 to come out of the vessel if not properly secured. To reduce the stress on the vessel, the sheath stopper may be pre-shaped into a curved or bayonet shape so that the stress of the sheath body when curved is imparted onto the sheath stopper rather than on the vessel. The sheath stopper 1005 may be made from springy but bendable material or include a spring element such as a stainless steel or nitinol wire or strip, so that when the dilator 260 is inserted into the sheath 220 and sheath stopper 1005, the sheath 220 is relatively straight, but when the dilator 260 is removed the sheath stopper 1005 assumes the pre-curved shape to reduce the force the sheath 220 imparts on the vessel wall. Alternately, the sheath stopper 1005 may be made of malleable material or include a malleable element such as a bendable metal wire or strip, so that it can be shaped after the sheath 220 is inserted into a desired curvature, again to reduce the stress the sheath 220 imparts on the vessel wall.

The access sheaths described herein can have a lubricious or hydrophilic coating to reduce friction during insertion into the artery and improve the ease of advancement of the device through the vasculature. The hydrophilic coating can be limited to the working portion of the device. In an embodiment, the distal portion of the shaft is dip-coated with a polymer material such as polyurethane. The dip coating may have gradual transitions between sections of varying thickness moving along the length of the device. In an embodiment, the distal coating is limited to the distal-most 0.5 cm to 3 cm of the elongated sheath body 222, so that it facilitates insertion without compromising security of the sheath in the puncture site or the ability of the operator to firmly grasp the sheath during insertion. In an alternate embodiment, the sheath has no coating. The access sheaths described herein may also include a radiopaque tip marker to facilitate placement of the device using fluoroscopy. For example, FIG. 3 shows the access sheath 220 having a radiopaque tip marker 230. In an example the radiopaque tip marker is a metal band, for example platinum iridium alloy, embedded near the distal end of the sheath body 222 of the access sheath 220. Alternately, the access sheath tip material may be a separate radiopaque material, for example a barium polymer or tungsten polymer blend.

As mentioned above, the arterial access device systems described herein can include one or more tapered dilators to improve entry into the artery. The entry or distal tip of the arterial access sheaths described herein can be tapered so as to allow smooth introduction of the sheath over a guide wire into the artery. The distal tip of the arterial access sheath itself can be configured such that when the access sheath is assembled with the sheath dilator to form a sheath assembly, the sheath assembly can be inserted smoothly over the sheath guide wire through the arterial puncture with minimal resistance. FIG. 5 shows a sheath dilator 260 that can be an elongated body inserted into the artery and enables smooth insertion of the access sheath 220 over the sheath guidewire 300 through a puncture site in the arterial wall. Thus, the distal end of the dilator 260 can be generally tapered to allow the dilator to be inserted over the sheath guidewire 300 into the artery, and to dilate the needle puncture site to a larger diameter for insertion of the access sheath 220 itself. To accommodate these functions, the dilator 260 can have a tapered end 268 with a taper that is generally between 6 and 12 degrees total included angle (relative to a longitudinal axis of the dilator), with a radiused leading edge. Sheath dilators can be locked to the access sheath when assembled for insertion into the artery. For example, a proximal hub 264 of the sheath dilator 260 can be structured to snap into or over a corresponding structure on the arterial access sheath 220, such as the proximal hub 224 having the hemostasis valve 226. An inner lumen of the dilator 260 can accommodate a sheath guidewire 300, with an inner diameter of between 0.037" to 0.041", depending on the sheath guide wire size for example.

In an embodiment, the arterial access device may be supplied in a kit that includes two or more tapered dilators. The first tapered dilator is used with the arterial access device to gain entry into the artery, for example the tapered dilator 260 of FIG. 5, and is thus sized and constructed in a manner similar to standard introducer sheath dilators. Example materials that may be used for the tapered dilator include, for example, high-density polyethylene, 72D Pebax, 90D Pebax, or equivalent stiffness and lubricity material. A second tapered dilator may be supplied with the arterial access device, with a softer distal section or a distal section that has a lower bending stiffness relative to the distal section of the first tapered dilator. That is, the second dilator has a distal region that is softer, more flexible, or articulates or bends more easily than a corresponding distal region of the first dilator. The distal region of the second dilator thus bends more easily than the corresponding distal region of the first dilator. In an embodiment, the distal section of the first dilator has a bending stiffness in the range of 50 to 100 N-mm$^2$ and the distal section of the second dilator has a bending stiffness in the range of 5 to 15 N-mm$^2$.

The second dilator (which has a distal section with a lower bending stiffness) may be exchanged with the initial, first dilator such that the arterial access device may be inserted into the internal carotid artery and around curvature in the artery without undue force or trauma on the vessel due to the softer distal section of the second dilator. The distal section of the soft, second dilator may be, for example, 35 or 40D Pebax, with a proximal portion made of, for example 72D Pebax. An intermediate mid portion or portions may be included on the second dilator to provide a smooth transition between the soft distal section and the stiffer proximal section. In an embodiment, both dilators may have radiopaque tip markers so that the dilator tip position is visible on fluoroscopy. In an embodiment, the distal most edge of one or both catheters is atraumatic and configured to reduce the likelihood of the distal most edge damaging or cutting tissue while being moved through the artery. The distal most edge may be rounded or may have any shape that reduces the likelihood of the distal most edge damaging tissue.

To facilitate exchange of the first dilator for the second dilator, one or both dilators may be constructed such that the distal section of the dilator is constructed from a tapered single-lumen tube, but the proximal portion of the dilator and any adaptor on the proximal end has a side opening. FIG. 19 shows an example of a dilator 4005 which is formed of an elongated member sized and shaped to be inserted into an artery, and a proximal hub 4020. The dilator has a side opening 4010, such as a slot, that extends along at least a portion of the length of the dilator 4005 such as along the elongated body and the proximal hub 4020. In an embodiment, the side opening 4010 is located only on a proximal region of the dilator 4005 and through the proximal hub 4020 although this may vary. The side opening 4010 provides access to an internal lumen of the dilator 4005, such as to insert and/or remove a guidewire into or from the lumen. An annular, movable sleeve 4015 with a slot on one side is located at or near the proximal hub 4020 of the dilator 4005. The sleeve 4015 may be moved, such as via rotation, about a longitudinal axis of the hub 4020, as described below. Note that the distal end of the dilator 4005 has a tapered configuration for dilating tissue.

FIG. 20 shows an enlarged view of the proximal region of the dilator 4005. As mentioned, the dilator 4005 has a side opening 4010 in the form of a slot that extends along the length of the dilator 4005 and the proximal hub 4020. The sleeve 4015 is positioned around the outer periphery of the dilator and is shaped such that it covers at least a portion of the side opening 4010. Thus, the sleeve 4015 can prevent a guidewire positioned inside the dilator 4005 from exiting the dilator via the side opening 4010. As mentioned, the sleeve 4015 is movable relative to the dilator 4005 and proximal hub 4020. In the illustrated embodiment, the sleeve 4015 is rotatable about a longitudinal axis of the dilator 4005 although other types of relative movement are within the scope of this disclosure. As shown in FIG. 21, the sleeve 4015 has a slot 4210 that can be aligned with the side opening 4010. When aligned as such, the slot 4210 and side opening 4010 collectively provide an opening for a guidewire to be inserted or removed from the internal lumen of the dilator 4005. The sleeve 4015 can be rotated between the position shown in FIG. 20 (where it covers the side opening 4010) and the position shown in FIG. 21 (where the side opening is uncovered due to the slit 4210 being aligned with the side opening 4010.)

A method of use of this embodiment of an arterial access device kit is now described. A guide wire, such as an 0.035" guidewire, is inserted into the common carotid artery, either using a Modified Seldinger technique or a micropuncture technique. The distal end of the guidewire can be positioned into the internal or external carotid artery, or stop in the common carotid artery short of the bifurcation. The arterial access device with the first, stiffer dilator, is inserted over the 0.035" wire into the artery. The arterial access device is inserted such that at least 2.5 cm of sheath is in the artery. If additional purchase is desired, the arterial access device may be directed further, and in to the internal carotid artery. The first dilator is removed while keeping both the arterial access device and the 0.035" wire in place. The side opening 4010 in the proximal portion of the dilator allows the dilator to be removed in a "rapid exchange" fashion such that most of the guidewire outside the access device may be grasped directly during dilator removal. The second dilator is then loaded on to the 0.035" wire and inserted into the sheath. Again, a dilator with a side opening 4010 in the proximal portion of the dilator may be used to allow the 0.035" wire to be grasped directly during guide wire insertion in a "rapid exchange" technique. Once the second dilator is fully inserted into the arterial access device, the arterial access device with the softer tipped, second dilator is advanced up the internal carotid artery and around bends in the artery without undue force or concern for vessel trauma. This configuration allows a more distal placement of the arterial access device without compromising the ability of the device to be inserted into the artery.

Alternately, one or more standard dilators may be used without side openings. If a standard dilator without a side opening is used, after the access device is inserted into the artery over a guide wire with the first dilator, the first dilator may be removed together with the guidewire, leaving only the access device in place. The second dilator with a guide wire preloaded into the central lumen may be inserted together into the arterial access device. Once fully inserted, the access device and second dilator with softer tip may be advanced distally up the internal carotid artery as above. In this alternate method, the initial guide wire may be used with both dilators, or may be exchanged for a softer tipped guide wire when inserted with the second softer tipped dilator.

Catheter Exemplary Embodiments

Described herein are catheters configured to be inserted through an arterial access device. Examples of catheters are described in U.S. Provisional Application Ser. No. 62/029,799, filed Jul. 28, 2014 and U.S. Provisional Application Ser. No. 62/075,101 entitled "Transcarotid Neurovascular Catheter" and filed Nov. 4, 2014, which are both incorporated by reference herein in their entirety.

As described above, FIGS. 1, 2 and 3 illustrates embodiments of a catheter 2030 that is configured to be inserted through an arterial access device 2010 into the common carotid artery (CCA), and from there advanced to a target treatment area in the internal carotid artery or cerebral artery. 22 shows a schematic view of an exemplary catheter 105. The catheter 105 has an external dimension that is sized and shaped for insertion into a blood vessel. A proximal hub 2065 has a female Luer configuration for attachment of a syringe during prep and attachment of other components. For example a separate hemostasis valve may be attached to proximal hub 2065, to allow introduction of devices such as a microcatheter, guide wire, or thrombectomy device while preventing or minimizing blood loss during the procedure. Alternately, the hemostasis valve may be integral to the catheter proximal adaptor. In an embodiment, this valve is an adjustable-opening valve such as a Tuohy-Borst or rotating hemostasis valve (RHV). In another embodiment, the valve is a passive seal hemostasis valve.

The catheter 105 may be made with a two or more layer construction. In an embodiment, the catheter has a PTFE inner liner, an outer jacket layer, and at least a portion of the catheter has a reinforcement structure, such as a tubular structure formed of, for example, a wound coil, braid or cut hyptotube. In addition, the catheter may have a radiopaque marker at the distal tip to facilitate placement of the device using fluoroscopy.

The catheter 105 has an insertable portion (i.e. working length) that is sized to be inserted through an access sheath in the carotid artery and passed through an arterial pathway (through the artery) to the distal ICA or cerebral vessels. In an embodiment the catheter 105 has a working length ranging from 40 to 70 cm. In an embodiment, the catheter has a working length of less than 70 cm, less than 60 cm, or less than 50 cm. Alternately, the length of catheter can be defined relative to the location of the access site and the target cerebral artery site. In an embodiment, the catheter is configured to be introduced into the artery at a location in the artery that is less than 40 cm, less than 30 cm, or less than 20 cm from the location of the target site as measured through the arterial pathway. The distance may further be defined by a ratio of working length to the distance between the location where the catheter enters the arteriotomy and the target site. In an embodiment, this ratio is less than 2×. In an embodiment, the working portion of the device may have a hydrophilic coating to improve the ease of advancement of the device through the vasculature. In an embodiment, at least 40% of the working length of the catheter is coated with a hydrophilic material. In other embodiments, at least 50% or at least 60% of the working length of the catheter is coated with a hydrophilic material.

In an embodiment, the distal-most portion is constructed to be more flexible than the proximal portion, with one or more flexible sections, to successfully navigate the internal carotid artery curvature to reach target sites in the distal ICA or cerebral arteries. The shaft may have a transition section of one or more increasingly stiff sections towards the more proximal section of the shaft, with the proximal most portion having the stiffest shaft section. Alternately, the transition section is a section of continuously variable stiffness from the distal section stiffness to the proximal section stiffness. In an embodiment, the distal most flexible section is 5 to 15 cm, a transition section is 5 to 15 cm, and a proximal stiff section takes up the remainder of the working length. In an embodiment where the catheter has a working length of 40 cm, the proximal stiff section is in a range 10 to 30 cm. In an embodiment where the catheter has a working length of 70 cm, the proximal stiff section is in a range from 40 to 60 cm.

Alternately, the flexible distal section and transition section may be described as a portion of the overall catheter working portion wherein the working portion is the portion that is configured to be inserted into an artery. In an embodiment, the flexible distal section may be between 3 to 10% of the length of the working portion of the catheter and the transition section may be between 15-35% of the length of the working portion of the catheter. In other embodiments, the distal section is at least 20% or at least 25% of the length of the working portion of the catheter.

In an embodiment, the flexibility of the distal most section is in the range 3 to 10 N-mm$^2$ and the flexibility of the proximal post section is in the range 100 to 500 N-mm$^2$, with the flexibility/flexibilities of the transition section falling between these two values.

As noted above, the catheter may have sections with discreet and/or continuously variable stiffness shaft. The sections of varying flexibility may be achieved by multiple methods. For example, the outer jacket layer may be composed of discreet sections of polymer with different durometers, composition, and/or thickness. In another embodiment, the outer layer has one or more sections of continuously variable outer layer material that varies in flexibility. The catheter may be equipped with the continuously variable outer layer material by dip coating the outer layer rather than laminating a jacket extrusion onto a PTFE-liner and reinforcement assembly of the catheter. The dip coating may be, for example, a polymer solution that polymerizes to create the outer jacket layer of the catheter. The smooth transition from one flexibility (e.g., durometer) to another flexibility along the length of the catheter can be accomplished via dipping the catheter assembly in multiple varying durometer materials whereby the transition from one durometer to another can be accomplished in a graded pattern, for example by dipping from one side of the catheter in one durometer with a tapering off in a transition zone, and dipping from the other side in another durometer with a tapering off in the same transition zone, so there is a gradual transition from one durometer to the other. In this embodiment, the dip coating can create a thinner walled outer jacket than a lamination assembly. In another embodiment, the catheter has an outer jacket layer that is extruded with variable durometer along the length, to provide variable flexibility along the length of the catheter.

In an embodiment, at least a portion of the catheter has a reinforcement structure, such as a tubular structure formed of for example, a wound coil, braid that is composed of discreet or continuously varying structure to vary the stiffness, for example a variable coil or braid pitch. In an embodiment, the reinforcement structure is a cut hyptotube, with a cut pattern that is graded along the length, for example cut in a spiral pattern with continuously variable pitch or continually variable cut gap, or a repeating cut pattern that allows the tube to flex whereby the repeating pattern has a continuously variable repeat distance or repeat size or both. A cut hypotube-reinforced catheter may also have superior pushability than a coil-reinforced catheter, as it is a structure with potentially greater stability in the axial direction than a wound coil. The material for the reinforcement structure may be stainless steel, for example 304 stainless steel, nitinol, cobalt chromium alloy, or other metal alloy that provides the desired combination of strengths, flexibility, and resistance to crush. In an embodiment, the reinforcement structure comprises multiple materials along the different sections of flexibility In another embodiment the catheter has a PTFE inner liner with one or more thicknesses along variable sections of flexibility. In an embodiment, the PTFE inner liner is constructed to be extremely thin, for example between 0.0005" and 0.0010". This embodiment provides the catheter with a high level of flexibility as well as the ability to construct a thinner-walled catheter. For example, the PTFE liner is constructed by drawing a mandrel through a liquid PTFE liquid solution rather than the conventional method of thin-walled PTFE tubing manufacture, namely extrusion of a PTFE paste which is then dried and sintered to create a PTFE tube. The draw method allows a very thin and controlled wall thickness, such as in the range of 0.0005"-0.0010".

Any one of the aforementioned manufacturing methods may be used in combination to construct the desired flexibility and kink resistance requirement. Current tri-layer catheters have wall thicknesses ranging from 0.005" to 0.008". These manufacturing techniques may results in a catheter with better catheter performance at the same wall thickness, or with equal or better catheter performance at lower wall thicknesses for example between 0.003" to 0.005".

In an embodiment, the distal flexible section of the catheter may be constructed using one or more of: a dip coated outer layer, an extremely thin drawn PTFE layer, and a cut hypotube reinforcement layer, with a gradual transition from the flexible section to a stiffer proximal section. In an embodiment, the entire catheter is constructed with one or more of these elements In some instances, there is a need to reach anatomic targets with the largest possible internal lumen size for the catheter. For example the catheter may be used to aspirate an occlusion in the blood vessel. Thus there is a desire to have a very flexible, kink resistant and collapse resistant catheter with a thin wall and large inner diameter. A catheter using the construction techniques disclosed herein meets these requirements. For example, the catheter may have an inner diameter of 0.070" to 0.095" and a working length of 25-50 cm. In another embodiment, the catheter may be sized to reach the more distal cerebral arteries, with an inner diameter of 0.035" to 0.060" and a working length of 40-80 cm. In an embodiment, the catheter is configured to navigate around a 180° bend around a radius as small as 0.050" or 0.100" without kinking, wherein the bends are located within 5 cm, 10 cm, or 15 cm of the arteriotomy measured through the artery. In an embodiment, the catheter can resist collapsing whilst in a tortuous anatomy up to 180°×0.050" radius bend without collapsing when connected to a vacuum up to 20 inHg. In an embodiment, the catheter can resist collapse in the same conditions when connected to a vacuum up to 25 inHg.

In another embodiment, the inner and/or outer diameter of the catheter is stepped up at a proximal region of the catheter such that the proximal region of the catheter has a larger inner and/or outer diameter than a remaining distal region of the catheter. FIG. 23 shows an embodiment with a distal portion 2070 with one inner and outer diameter, and a proximal portion 2075 with a larger inner and outer diameter relative to the distal portion. In one embodiment, the length of the distal portion of the catheter is configured to be placed in smaller distal vessels, whereas the larger proximal portion will reside in more proximal, larger vessels. In this embodiment, the catheter may have one diameter for the distal 10-25 cm, then have a step up in diameter of between 10-25% for the remainder of the working length. The step up would occur over a tapered transition section between 3 and 10 mm in length, depending on the size of the step up and the need to make a smooth transition. Alternately, the catheter is used with a stepped sheath with a larger diameter proximal region such as the embodiment of FIG. 8 or a sheath with a larger diameter proximal extension as in FIG. 10. In this case, the catheter may be stepped up a length and diameter to match the stepped sheath. For example, if the sheath has a portion with larger diameter for the proximal 20 cm of the sheath, the catheter would have a larger diameter for a longer length such as the proximal 25 cm to allow for additional length through proximal adaptors and valves such as an RHV. The remaining distal region would have a smaller diameter, with a step up over a tapered transition section between 3 and 10 mm in length, depending on the size of the step up and the need to make a smooth transition.

Figure 24A:
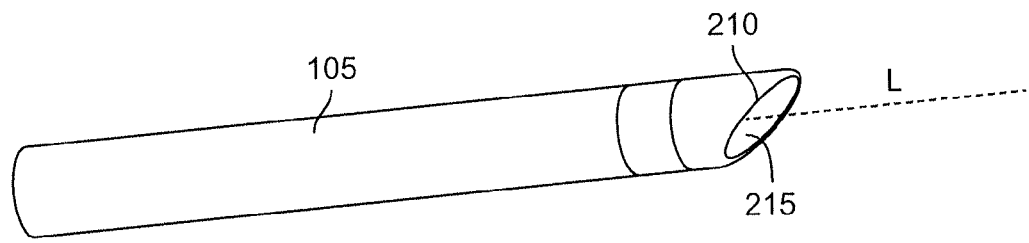
FIGS. 24A-D show examples of catheters having non-square distal tips or distal edges.
Figure 24B:
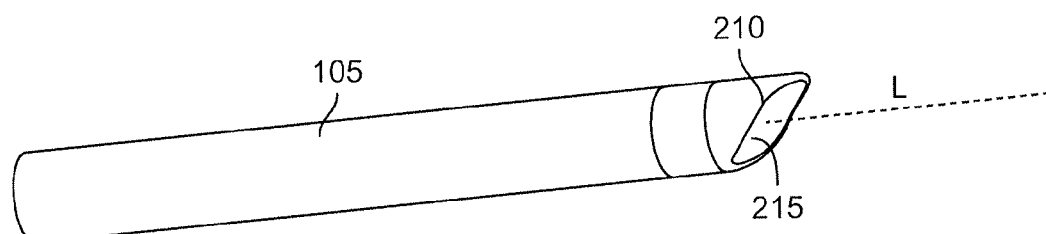
Figure 24C:
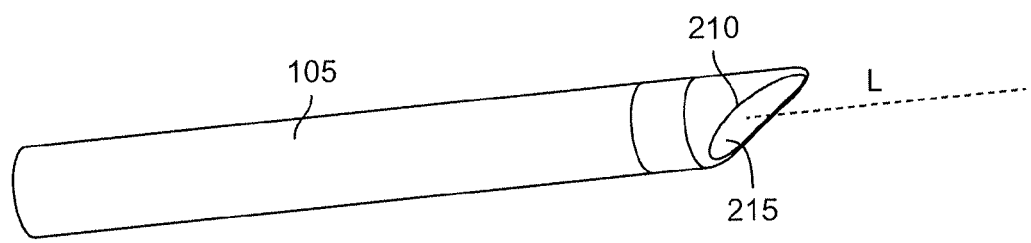
Figure 24D:
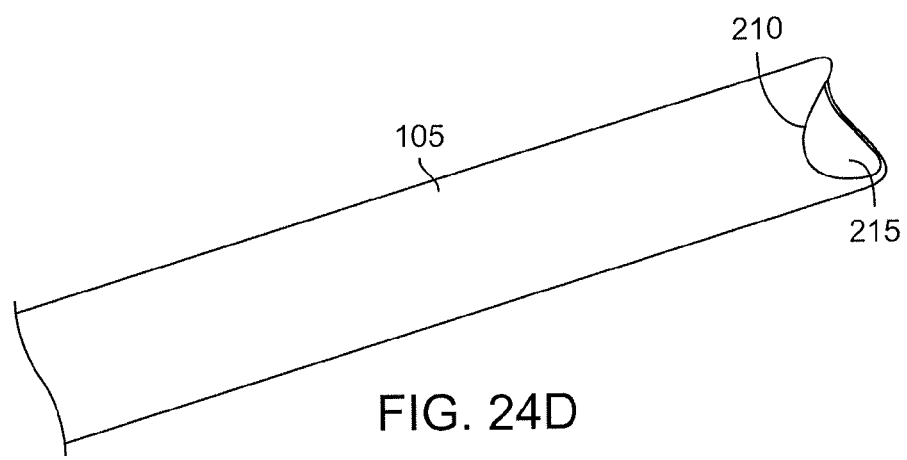

In some instances, the catheter is used to aspirate a clot in an artery. FIGS. 24A-D show examples of catheters having non-square distal tips or distal edges. With reference to FIG. 24A, the distal region of a catheter 105 is shown. The catheter 105 has a distal-most tip or edge 210 that forms an opening 215 at the distal end of the catheter 105. The distal edge 210 forms an angle that is non-perpendicular relative to the longitudinal axis L. Such a tip defines a different sized opening 215 than if the tip were perpendicular to the axis L. That is, the opening 215 is larger and presents a larger suction area relative to a distal tip that is cut normal to the longitudinal axis. The catheter therefore may provide a larger suction force on the occlusion located near the tip. The larger area opening 215 also facilitates suctioning the clot into the lumen of the catheter, rather than just capturing the clot at the tip with suction force and pulling back the captured clot with the catheter. In FIG. 24A, the catheter 105 has an angled, straight edge 210 creating an elliptical opening 215. In FIGS. 24B, 24C, and 24D, the distal edge 210 is curved or non-straight such that the distal opening 215 is non-planar and may offer greater opening without extending the tip length out as much, which may optimize the contact area with the occlusion further. The distal edge 210 may be straight, curved, undulating, or irregular. In an embodiment with a cut hypotube-reinforced catheter, the distal tip of the hypotube can be formed with the non-square shape. In an embodiment with a radiopaque marker band, the radiopaque marker band may have a non-square edge which can then be used to create the non-square catheter tip shape.

A cause of difficulty in advancing catheters through severe bends and across side branches is the mismatch between the catheter and the inner guiding components such as smaller catheters, microcatheters, or guidewires. One technique for advancing a catheter is called a tri-axial technique in which a smaller catheter or microcatheter is placed between the catheter and the guide wire. However, with current systems the smaller catheter has a diameter mismatch between either the larger catheter, the guide wire, or both, which creates a step in the system's leading edge as the system is advanced in the vasculature. This step may cause difficulty when navigating very curved vessels, especially at a location where there is a side-branch, for example the ophthalmic artery. In an embodiment, as shown in Figure A, the catheter 105 is supplied with a tapered co-axial inner member 2652 that replaces the smaller catheter generally used. The inner member 2652 is sized and shaped to be inserted through the internal lumen of the catheter. The inner member 2652 has a tapered region with an outer diameter that forms a smooth transition between the inner diameter of the catheter 203 and the outer diameter of a guidewire 2515 or microcatheter that extends through an internal lumen of the inner member 2652. In an embodiment, the tapered dilator or inner member 2652, when positioned within the catheter, creates a smooth transition between the distal-most tip of the larger catheter 105 and the outer diameter of a guide wire 2515 which may be in the range of 0.014" and 0.018" diameter for example. For example, the inner luminal diameter may be between 0.020" and 0.024". In another embodiment, the inner diameter is configured to accept a microcatheter with an outer diameter in the range of 0.030" to 0.040" or an 0.035" guide wire in the inner lumen, for example the inner luminal diameter may be 0.042" to 0.044".

In a variation of this embodiment, shown in FIG. 25B, in addition to the tapered region, the inner member 2652 includes an extension formed of a uniform diameter or a single diameter, distal-most region 2653 that extends distally past the tapered portion of the inner member 2652. In this embodiment the distal region 2653 of the inner member 2652 may perform some or all of the functions that a microcatheter would do during an interventional procedure, for example cross an occlusion to perform distal angiograms, inject intraarterial agents, or deliver devices such as aneurysm coils or stent retrievers. In this manner, a microcatheter would not need to be exchanged for the dilator for these steps to occur.

The material of the dilator (inner member 2652) is flexible enough and the taper is long enough to create a smooth transition between the flexibility of the guide wire and the catheter. This configuration will facilitate advancement of the catheter through the curved anatomy and into the target cerebral vasculature. In an embodiment, the dilator is constructed to have variable stiffness, for example the distal most section is made from softer material, with increasingly harder materials towards the more proximal sections. In an embodiment, distal end of the tapered dilator has a radiopaque marker such as a platinum/iridium band, a tungsten, platinum, or tantalum-impregnated polymer, or other radiopaque marker.

In another embodiment, a catheter system includes an anchor device which is configured to be easily navigable through the vasculature to a location distal to the cerebral occlusion. When the anchor is deployed, it may be used as a rail and counter force to facilitate advancement of the catheter to the proximal face of the occlusion. In an example shown in FIG. 26, the anchor is a microcatheter 2505 with a distal balloon 2510. The microcatheter 2505 is placed over a guidewire 2515 to a site distal of the target treatment area, for example a thrombus 10, and then the distal balloon 2510 is inflated. Alternately, the microcatheter has an atraumatic guidewire tip built in and is advanced as a stand-alone device. The catheter 2030 can then use the shaft of the microcatheter 2505 as a rail to be advanced towards the treatment site, as is done in conventional techniques. However, because the balloon 2510 is inflated, the distal end of the microcatheter 2505 is anchored against the vessel wall and provides counter force to the advancing catheter 2030. The guidewire 2515 remains in place during this maneuver, such that if the anchor (i.e., the balloon 2510) and catheter 2030 need to be re-advanced, access is maintained across the treatment site with the guide wire 2515.

The atraumatic distal anchor can be a device other than a balloon. For example, other atraumatic distal anchors may include microcatheters with mechanically expandable-tips such as a braid, coil, or molly-bolt construction. The expandable tip can be configured to be sufficiently soft and to provide sufficient force along a length of the microcatheter so as to reduce focal pressure against the vessel wall and minimize vessel wall injury.

Figure 27:
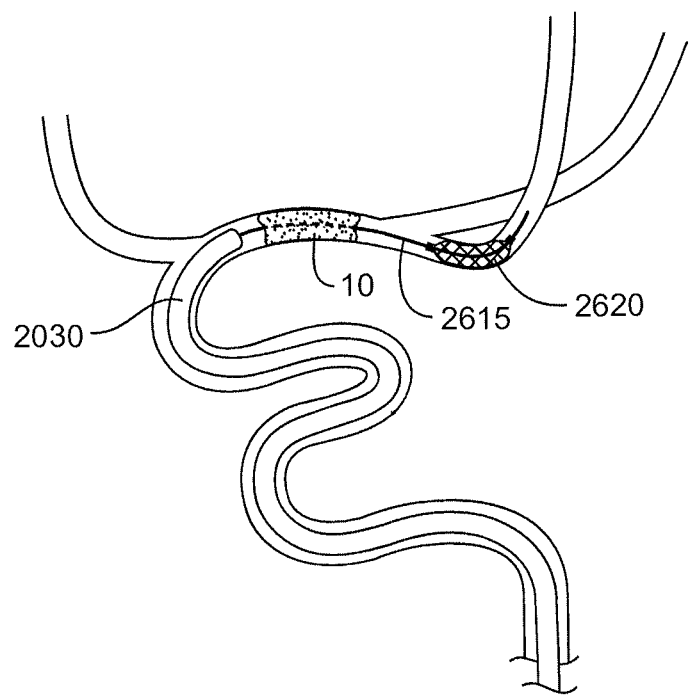
FIG. 27 shows a guidewire with an anchor device.

Another variation of this embodiment as shown in FIG. 27 is a guidewire 2615 with an expandable tip 2620 such as a balloon or expandable cage or stent. The guidewire 2615 may be placed in the vasculature using a microcatheter and then deployed when the microcatheter is retracted. The expandable portion of the guidewire 2615 device may be formed from separate braided filaments or cut from a single hypotube and expand with a counterforce actuating member. For example the proximal end of the expandable tip may be attached to the distal end of a hollow hypotube, and the distal end attached to a wire which runs the length of the hypotype. When the wire is pulled back, the expandable tip is shortened in length and expanded in diameter. Pushing the wire forward would collapse the expandable tip.

Figure 28:
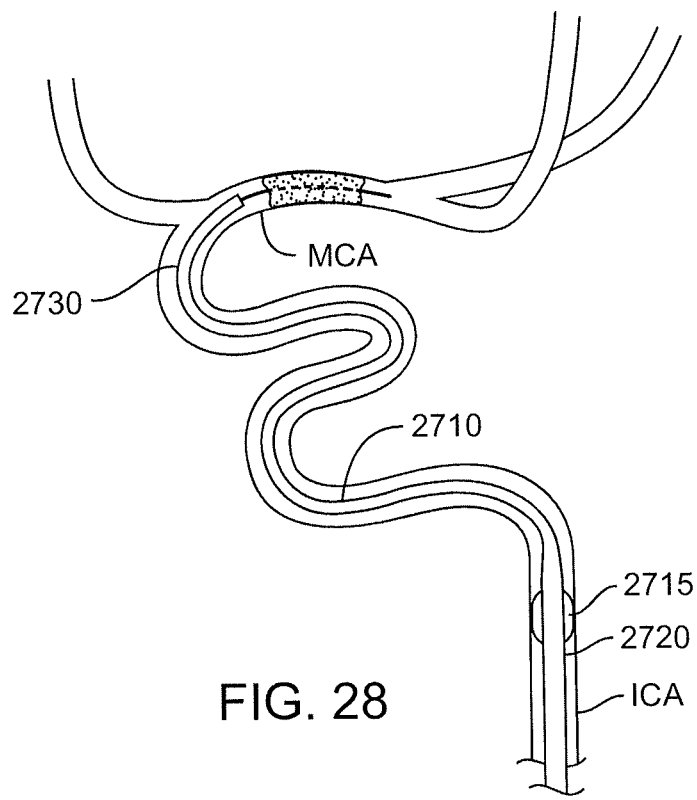
FIG. 28 shows a catheter and an arterial access device combined in a single device.

In another embodiment, shown in FIG. 28, the catheter and the arterial access device are combined to be a single device 2710 with a continuous lumen extending through the length of the device. A proximal portion 2720 comprises the arterial access sheath and a distal portion 2730 functions as the catheter. The embodiment may include an occlusion balloon 2715 located between the distal and proximal portion. The distal portion 2730 is constructed to be more suited for navigating the cerebral vasculature. In particular, the distal portion 2730 is more flexible and tapered to a smaller diameter than the proximal portion 2720.

Figure 29:
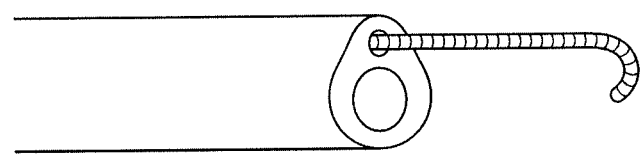
FIGS. 29 and 30 show a catheter having a pair of lumens.
Figure 30:
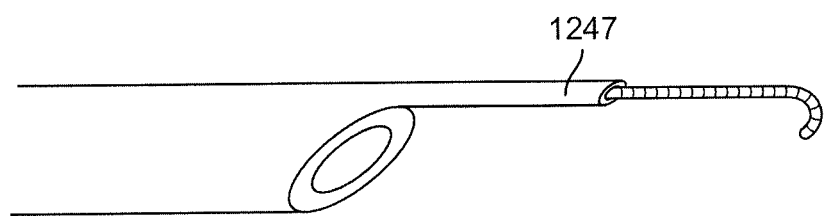

In another embodiment, as shown in FIGS. 29 and 30, the catheter has a second lumen to maintain guide wire access to facilitate re-advancement or exchange of the catheter without recrossing the target anatomy. In an embodiment, shown in FIG. 29, the catheter has two lumens which terminate together at the distal tip: a main lumen and a second guidewire lumen. The termination may be such that a distal-facing surface is arranged at an angle (relative to the longitudinal axis of the catheter), to facilitate tracking of the catheter through the vasculature. In another embodiment, shown in FIG. 30, the second guidewire lumen is inside an extension 1247 that extends out past the termination of the main lumen. The extension 1247 is a distal-most region of the catheter that protrudes distally past an opening formed by the main lumen. The extension 1247 forms a shaft having a reduced outer diameter relative to the outer diameter of the catheter around the main lumen. The second lumen is smaller than the shaft of the main catheter, and may be positioned in or across an occlusion while the distal end of the main lumen is positioned on the proximal face of an occlusion. The distal end of the main lumen may be terminated at an angle as well, to facilitate tracking of the device.

In some instances, it may be desirable for the catheter to have an distal tip which can increase in diameter after being positioned at a target treatment site, for example to facilitate removal of an occlusion when an aspiration device is connected to the proximal portion of the catheter. In an embodiment, the catheter has an expandable tip portion. The expandable tip portion may be constructed with a mechanical structure such as a braid or stent structure, which can open or close in a repeatable manner. The mechanism for opening the tip may be a pull-wire which shortens the expandable portion, or an outer retention sleeve which maintains the distal section in a small diameter but when retracted allows the distal tip to expand. The distal section may be covered with a membrane such that when aspiration is applied, either with the tip expanded or not, a vacuum may be applied at the very tip of the catheter. The expandable tip allows the catheter to maintain a small profile during tracking of the catheter to the target anatomy, but then expands the distal luminal area for facilitated capture of occlusive material such as thrombus. The thrombus, once captured into the catheter, may be sucked all the way into the aspiration device, or alternately will be lodged in the lumen of the catheter where the catheter is no longer expanded, and at that point can be removed by retraction of the entire catheter.

Figure 31A:
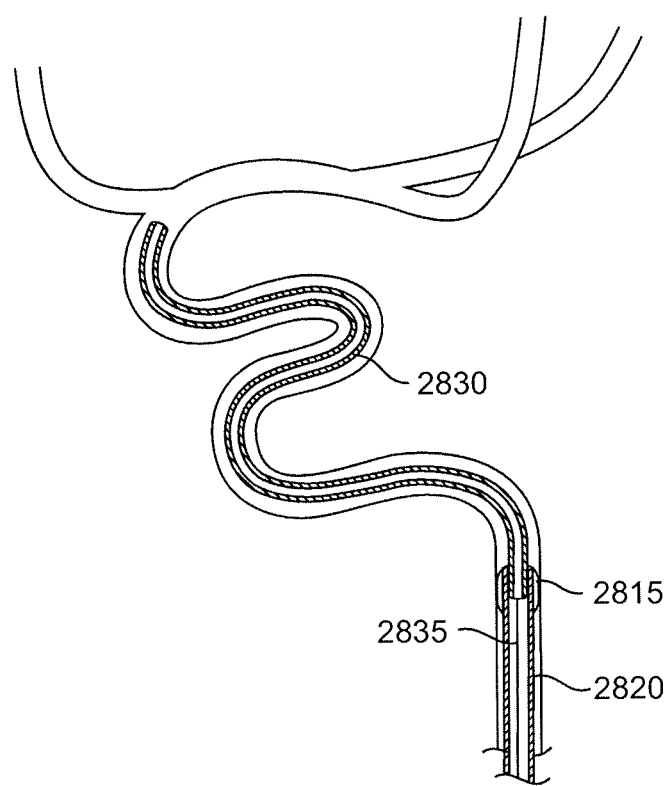
FIGS. 31A-31C show a telescopic catheter and arterial sheath system.

In another embodiment, shown in FIG. 31A, the catheter 2830 is a telescopic attachment to the distal portion of the arterial access device 2820. In this regard, the catheter can be formed of two or more concentric, tubular sections that telescopically slide relative to one another to increase and/or decrease the entire collective length of the movably attached tubular sections. The distal region of the arterial access device 2820 has one or more structures that telescopically extend in the distal direction along the longitudinal axis of the arterial access device. The structures may also be telescopically collapsed such that they do not extend past the distal end of the arterial access device. When the structures are telescopically expanded past the distal end of the arterial access device, the structures collectively form a continuous inner lumen. A tether element such as a wire 2835 may be connected to the proximal end of the catheter 2830 and extends out the proximal end of arterial access device such that the telescoping actuation may be accomplished by pushing or pulling the tether element from the proximal end of the arterial access device. Thus the tether element must be of sufficient rigidity to push the catheter without buckling. The junction between the tether element 2835 and the catheter 2830 includes a transition zone that bridges the flexibility of the catheter and the rigid tether element, so as to avoid kinking during actuation of the telescoping catheter. For example the tether element may be flattened, ground down, or further down-sized to be more flexible at the transition zone, and/or the catheter may be made more rigid via reinforcement construction or material selection. An occlusion member, such as balloon 2815, may be positioned on the arterial access device 2820 or catheter 2830. Both the access device 2820 and catheter 2830 has a distal radiopaque marker. Additionally, the catheter has a radiopaque marker at the proximal end where the tether 2835 joins the catheter, so that the user may visualize the distance between the distal end of the access device and the proximal end of the catheter, and therefore visualize the overlap region between the two.

Figure 31B:
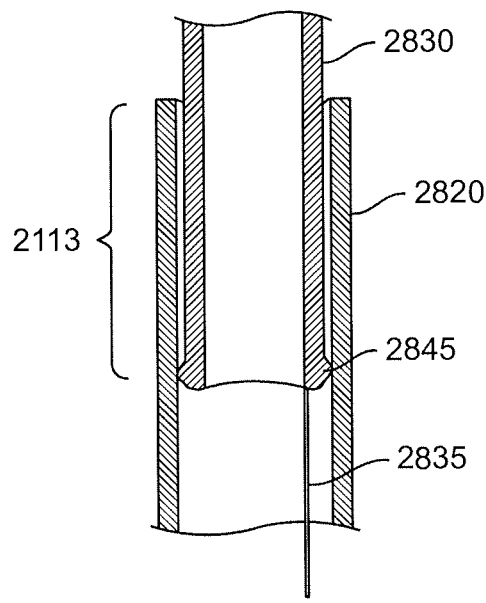
Figure 31C:
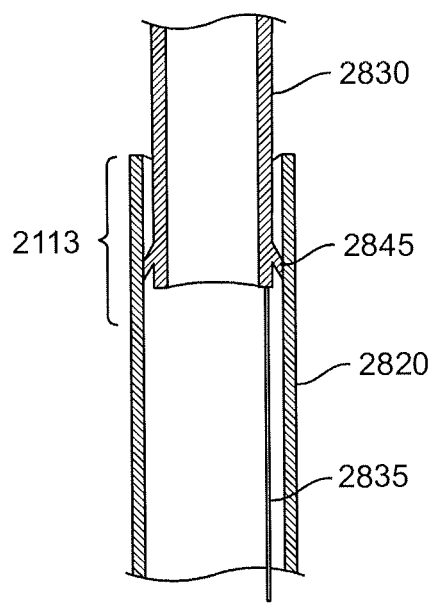

It may be sufficient for the contact area between the overlapping portion of the arterial access device 2820 and the catheter 2830 to provide sufficient seal such that the aspiration or pressure force is transmitted to the distal end of the catheter 2830 with no leakage at the junction between the two devices. However, if additional sealing is needed, the system may include a sealing element at the juncture between the arterial access device 2820 and the catheter 2830. This embodiment is also useful if multiple size catheters are required during a procedure to reach different target sites, without the necessity of replacing the arterial access device. The sealing element of a smaller catheter 2830 can be designed to seal the larger gap between the catheter and the access device. One embodiment of a seal element is shown in FIG. 31B. A sealing element 2845 may be positioned on the external surface of the proximal end of the catheter 2830. In an embodiment, the sealing element 2845 is one or more external ridge features manufactured from an elastomeric material, and which is compressed when the catheter 2830 is inserted into the lumen of the arterial access device 2820. The ridge geometry is such that it behaves as an O-ring, quad ring, or other piston seal design. FIG. 31C shows a similar configuration, with the sealing element 2845 having a wiper seal configuration such as an inclined surface that is biased against an inner surface of the arterial access device 2820. Alternately, the seal 2845 may be an inflatable or expandable member such as a balloon or covered braid structure that can be inflated or expanded and provide sealing between the two devices at any time, including after the catheter 2830 is positioned at the desired site. An advantage to this embodiment is that there is no sealing force being exerted on the catheter during catheter positioning, but rather is applied after the catheter is positioned. Alternately, the sealing element is on the inner of the distal end of the arterial access device 2820, with structures similar to those described above.

In an embodiment, the arterial access device 2820 and catheter 2830 with features to allow the two to be telescopically coupled as in FIG. 31A are supplied together in a kit. In an embodiment, the kit also includes a sheath dilator and sheath guidewire to aid in insertion of the arterial access device through a puncture into the artery. In an exemplary embodiment configured for transcarotid access into the carotid, the arterial access device has insertable portion between 15-30 cm in length, and the telescoping catheter is 10 to 15 cm in length. In an alternate exemplary embodiment, the arterial access device is a long sheath configured to be positioned into the carotid artery from a transfemoral access site. In this embodiment, the arterial access device is between 90 and 120 cm in working length, and the telescoping catheter is 10 to 25 cm in length. In either case, the tether is of a length that allows manipulation of the catheter 2830 when positioned to its full length extending from the arterial access device 2820. In an embodiment, the kit also includes a sheath dilator and a sheath guide wire to position the arterial access device in the carotid artery. In an embodiment the kit also includes an inner tapered sheath such as that shown in FIG. 25A or FIG. 25B to aid in telescopingly positioning the catheter 2830.

In an embodiment, the arterial access device 2820 is a 6F sheath size with ID about 0.086" to 0.088", and the catheter 2830 has an outer diameter of between 0.083" and 0.086" and an inner diameter of between 0.068" and 0.072". In an alternate embodiment, the arterial access device 2820 is a 5F sheath size with ID about 0.074" to 0.076", and the catheter 2830 has an outer diameter of between 0.071" and 0.073" and an inner diameter of between 0.058" and 0.062". Other diameter combinations are possible as warranted by the procedure.

In another embodiment, the catheter 2830 includes a structure for morcelating the thrombotic occlusion as it is being aspirated into the catheter. In an embodiment, a separate thrombus disruption device with an expandable distal segment is inserted into the catheter and positioned inside the lumen near the distal tip, once the catheter is positioned at the target site and the inner guide wire and/or inner catheter or dilator are removed. The device is inserted with the expandable segment in the collapsed state and the expanded proximal to the distal tip of the catheter. The device is configured to be small enough in this state that it should have minimal interference with thrombus aspiration. In an exemplary method, the thrombus disruption device is connected to a rotary motor at the proximal end such that the expandable portion is rotating at the distal segment of the catheter. Aspiration is then initiated at the proximal end of the catheter. As thrombus is aspirated into the catheter, the rotating expandable section breaks up the clot which is then easily aspirated through the length of the catheter. Alternately, the thrombus disruption device is expanded but remains still and is only rotated or translated back and forth after aspiration has started and if and when the clot becomes stuck in the lumen of the catheter. In an embodiment, the device also includes a short atraumatic distal tip, such as a floppy tip on a neurovascular guide wire. This feature minimized the chance of this device causing vascular injury should it protrude from the distal end of the catheter at any time during its use.

Figure 51:
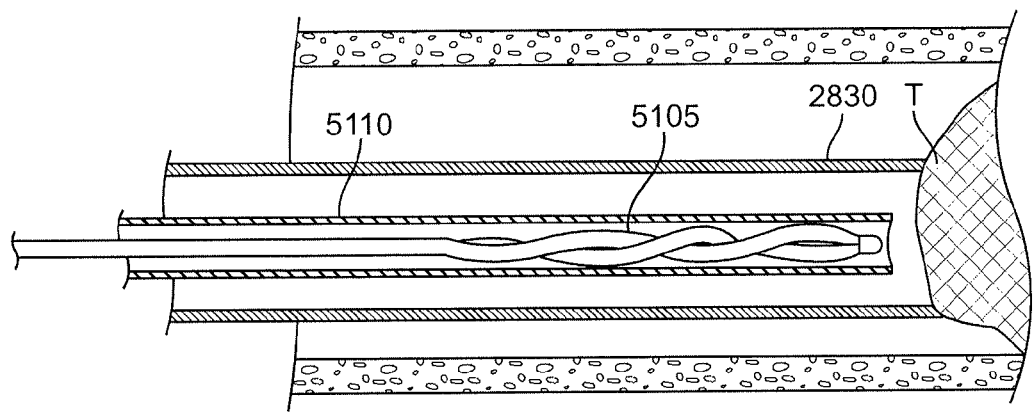
FIGS. 51-53 show thrombus disruption devices.
Figure 52:
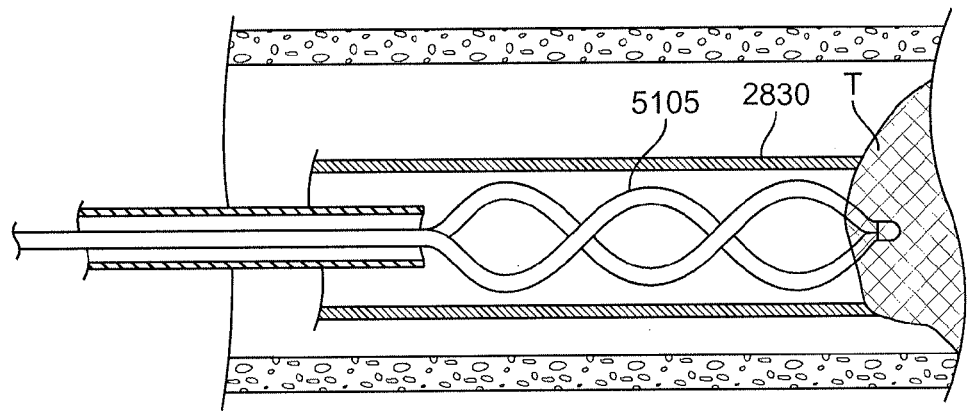
Figure 53:
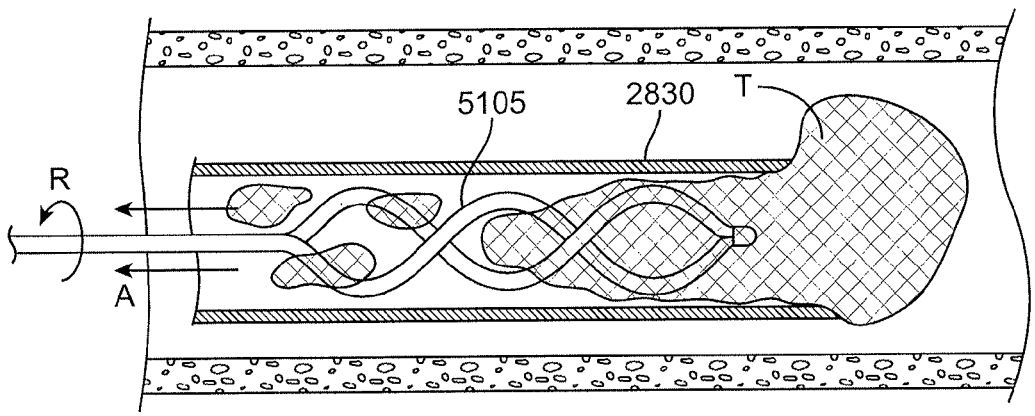

In an embodiment, the thrombus disruption device is manufactured from a generally elongate structure, coupled with an inner member attached at the distal end to actuate the expandable segment. The construction of the expandable segment may be a braid, one or more helical wires, or a tube with a cut pattern, any of which are designed to expand when shortened by pulling the inner member. Alternately, as shown in FIG. 51, the thrombus disruption device 5105 is formed of a generally elongate structure, coupled with a retractable sleeve 5110 that constrains the expandable segment during delivery. The construction of the expandable segment may be a braid, one or more helical wires, or a tube with a cut pattern, or a brush-type structure that is designed to expand when the constraining retractable sleeve is retracted, as seen in FIG. 52. The retractable sleeve 5110 may be a microcatheter. If the device is to be rotatable, the shaft of the device can transmit torque, such as a braid-reinforced construction, a counter-wound coil construction, or the like. As with the catheter, the device is very flexible at the distal end for navigation into the intracranial and cerebral anatomy, with increasingly stiff properties as one moves towards the proximal end, so that the device can be easily delivered, the expandable section quickly actuated. If a thrombotic piece T is caught in the tip of the catheter 2830, as seen in FIG. 53, the device 5105 is rotated as indicated by the arrow R, or moved back and forth as required to break up the thrombus, or alternately the device 5105 is rotated throughout the aspiration step to ensure that the clot is never clogging the distal tip of the catheter but is immediately broken up once aspirated into the distal tip. Aspiration as indicated by the arrows A is maintained throughout this maneuver to ensure that the morecelated thrombus is removed via the catheter 2830 and not re-inserted into the blood stream.

Many of the catheter configurations described herein provide a benefit in aspiration ability over existing methods and devices particularly when the cathereter is combined with one of the disclosed arterial access devices. This benefit translates to more rapid and more effective removal of thrombotic occlusion and reduced distal emboli in the treatment of strokes. This benefit is derived at least from from shorter and in some cases larger inner lumen diameter aspiration catheter designs. According to Poiseuille's law for laminar flow in a tube, the flow rate can be expressed as the equation $Q = \pi \times r4 \times (\Delta P)/8 \times n \times L$, where Q=flow rate, r=radius of the tube, P=pressure, n=viscosity, and L=length. As shown by this equation, flow rate drops by increases in length and drops proportionally by decreases in radius to the fourth power. The transcarotid embodiments described herein allow aspiration rates through catheters about half the length, and therefore potentially twice the flow with respect to prior devices. In addition, the embodiments disclosed herein allow larger diameter catheters the ability to reach the same target sites more easily and more often, due to the greater proximal support from the transcarotid access site, the greater catheter pushability due to the more distal transition from flexible to stiff segments, and the tapered inner members as in FIGS. 25A and 25B, among other features.

For example, one catheter currently used for clot aspiration is the Navien 058 or the Navien 072 catheters (sold by Covidien). These catheters have inner diameters of 0.058" and 0.072" respectively and lengths of 115 and 105 cm respectively. Although the Navien 072 catheter has been demonstrated to be a more effective catheter for removal of cerebral thrombus, it is less often able to reach the target site. In contrast, the Penumbra 5Max and 5Max ACE are frequently able to reach the face of the clot, and additionally has a stepped configuration that offers some diameter benefit. However, these catheter configurations still do not perform as well as the catheters disclosed herein. Catheters configured for transcarotid delivery, as in FIG. 22, provide aspiration benefit. Catheters that are both stepped and configured for transcarotid delivery, as in FIG. 23, provide even more benefit. Finally, a telescoping configuration as in FIG. 31A offers benefit in a transfemoral configuration and even more benefit in a transcarotid configuration. These benefits are calculated according to Poiseuille's law assuming a fluid viscosity n of 3.7 centipoise (the equivalent of typical human blood viscosity at body temperature), as shown in the tables in FIG. 54 for the smaller catheter sizes, and FIG. 55 for the larger catheter sizes.

When different catheter systems are tested for actual aspiration rates this benefit is diminished somewhat as compared to the theoretical aspiration rates, especially at higher flow rates. This is reflective of the fact that at the higher flow rates, the flow is less and less laminar, and thus lower than the theoretical flow as predicted by Poiseuille's law. However, the shorter and larger ID catheters do show a relative benefit. In an exemplary test method, the catheters are tested for aspiration rates with a 40% glycerin mixture to simulate the viscosity of blood using the following method: each catheter was connected to a stopcock and thence to a 30 cc locking syringe. The tip of the catheter was positioned in a container of the glycerin mixture. The catheter and syringe were purged of air, the syringe was emptied, and then the stopcock was closed. The locking syringe was then pulled back the full 30 cc volume and locked in place. A timer was started when the stopcock was opened, and the time was noted at 5 cc, 10 cc, 15 cc and 20 cc of extracted solution in the syringe. The overall average extraction rate was calculated based on the slope of the data points and was roughly linear over the 20 cc volume, indicating a constant vacuum level using this method. Results and their relative improvements over the baseline Navien Catheters are provided in the tables in FIGS. 56 and 57.

Exemplary Embodiments of Aspiration and Flow Control

As described above, it is sometime desirable to include aspiration or flow reversal devices or structures to the system. Described herein are aspiration and flow control elements configured to be used with an arterial access device, a guide catheter, and/or a catheter of the disclosed system. Examples of aspiration and flow control elements are described in U.S. Patent Publication No. 2014/0296868, filed Mar. 21, 2014, which is incorporated by reference herein in its entirety. Any or all of the arterial access device 2010 and the catheter 2030 may be connected to sources of passive or active aspiration via flow lines 2025 or 2045 (FIG. 1) on the devices. Additionally, the guide catheter 2105 may be connected to sources of passive or active aspiration via flow line 2125 (FIG. 3) on the device. The mode of aspiration may be different for each device.

Figure 32:
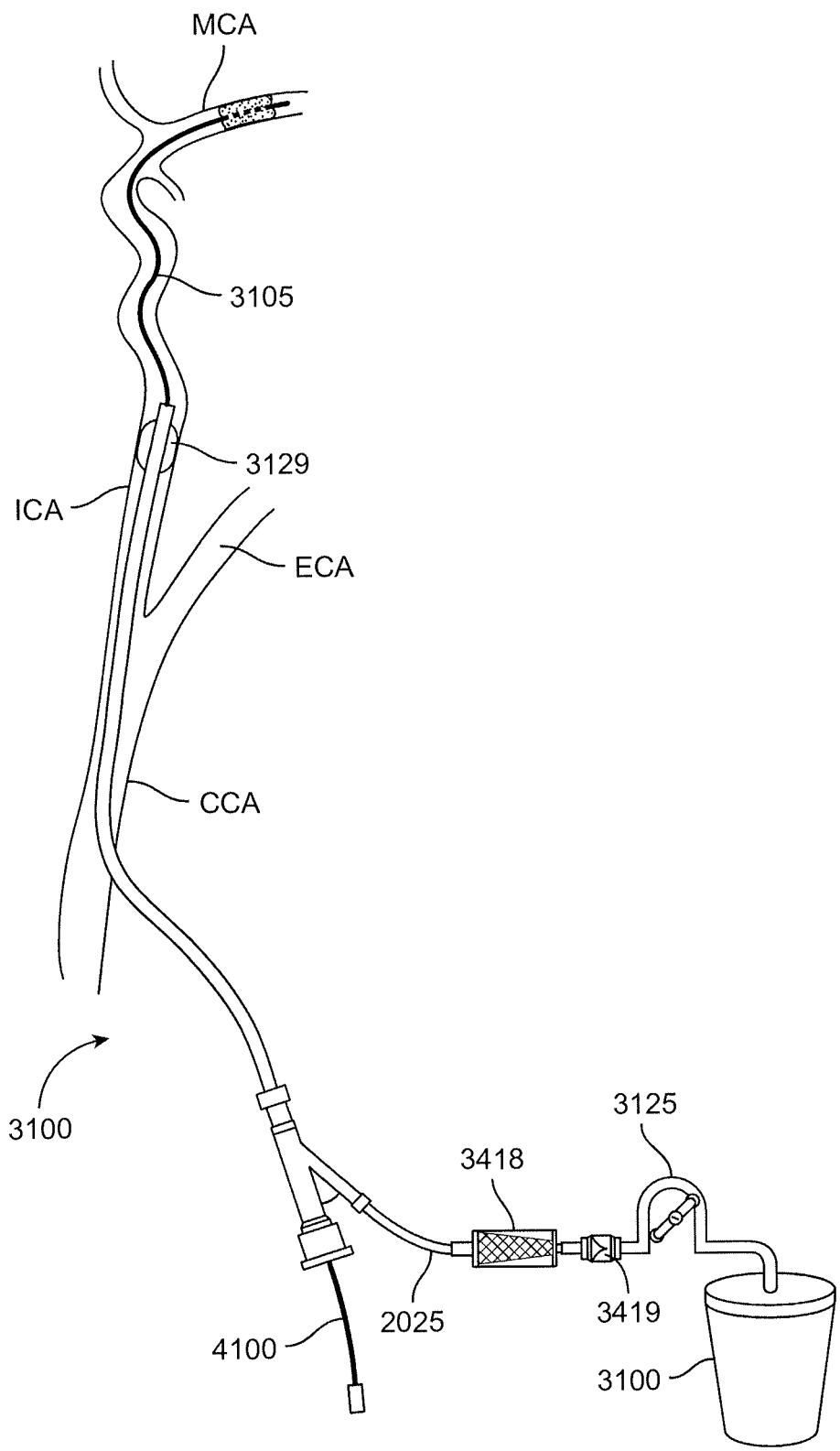
FIGS. 32-35 show examples of systems for treating an artery with active aspiration.
Figure 33:
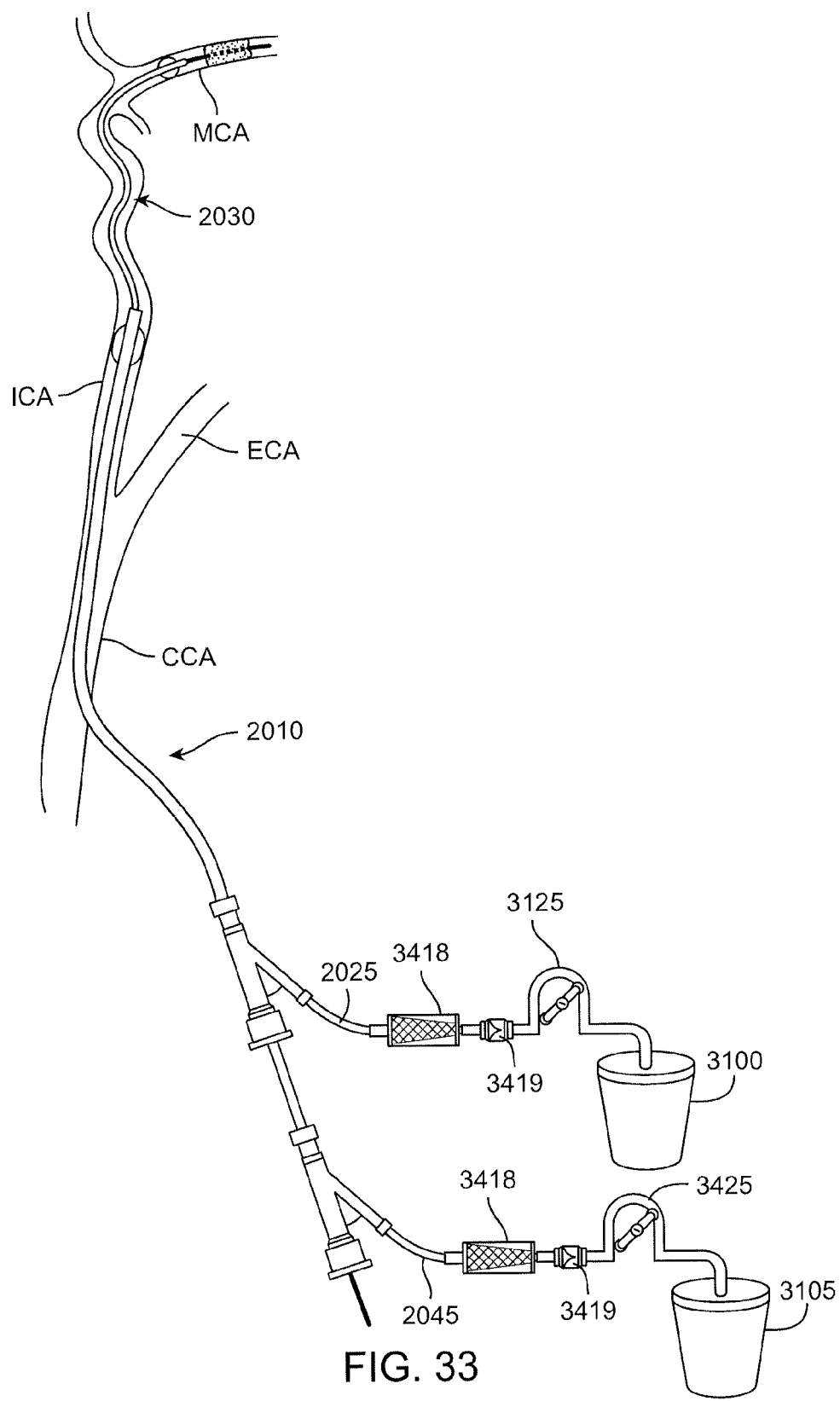

In FIG. 32, the flow line 2025 of the arterial access device 2010 is connected to a delivery location, such as a receptacle 3100. A source of aspiration 3125 may be coupled to the flow line 2025. The receptacle 3100 and source of aspiration 3125 may be separate or may be combined into a single device such as a syringe. A filter 3418 and/or a check valve 3419 may be coupled with flow line 2025. In FIG. 33, the flow line 2045 of the catheter 2030 is additionally or alternately connected to a separate aspiration source 3425 and delivery location, such as receptacle 3105. The aspiration source 3425 and delivery location may be combined into a single device such as a syringe. A filter 3418 and/or a check valve 3419 may also be coupled with the flow line 2045.

Figure 34:
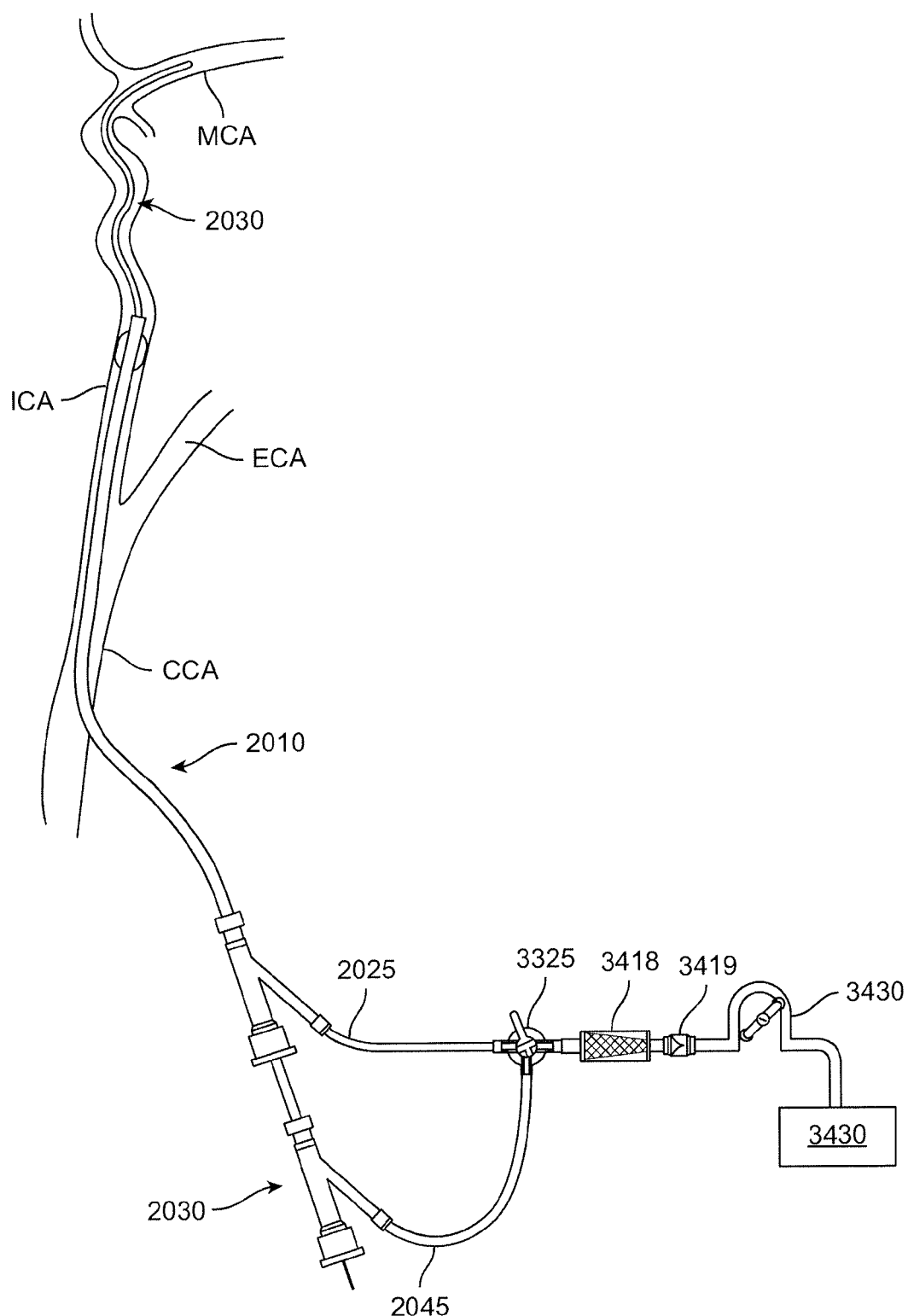

FIG. 34 shows a system whereby both the arterial access device 2010 and catheter 2030 are connected to the same aspiration source 3430 via flow lines 2025 and 2045, respectively. A valve 3325 controls which device is connected to the aspiration source 3430. The valve may enable one device, the other device, both devices, or neither device to be connected to the aspiration source at any given time. The valve may be a 3-way or 4-way stopcock. Alternately, the valve may be a flow controller with a simple actuation which selects the configuration as described above.

Figure 35:
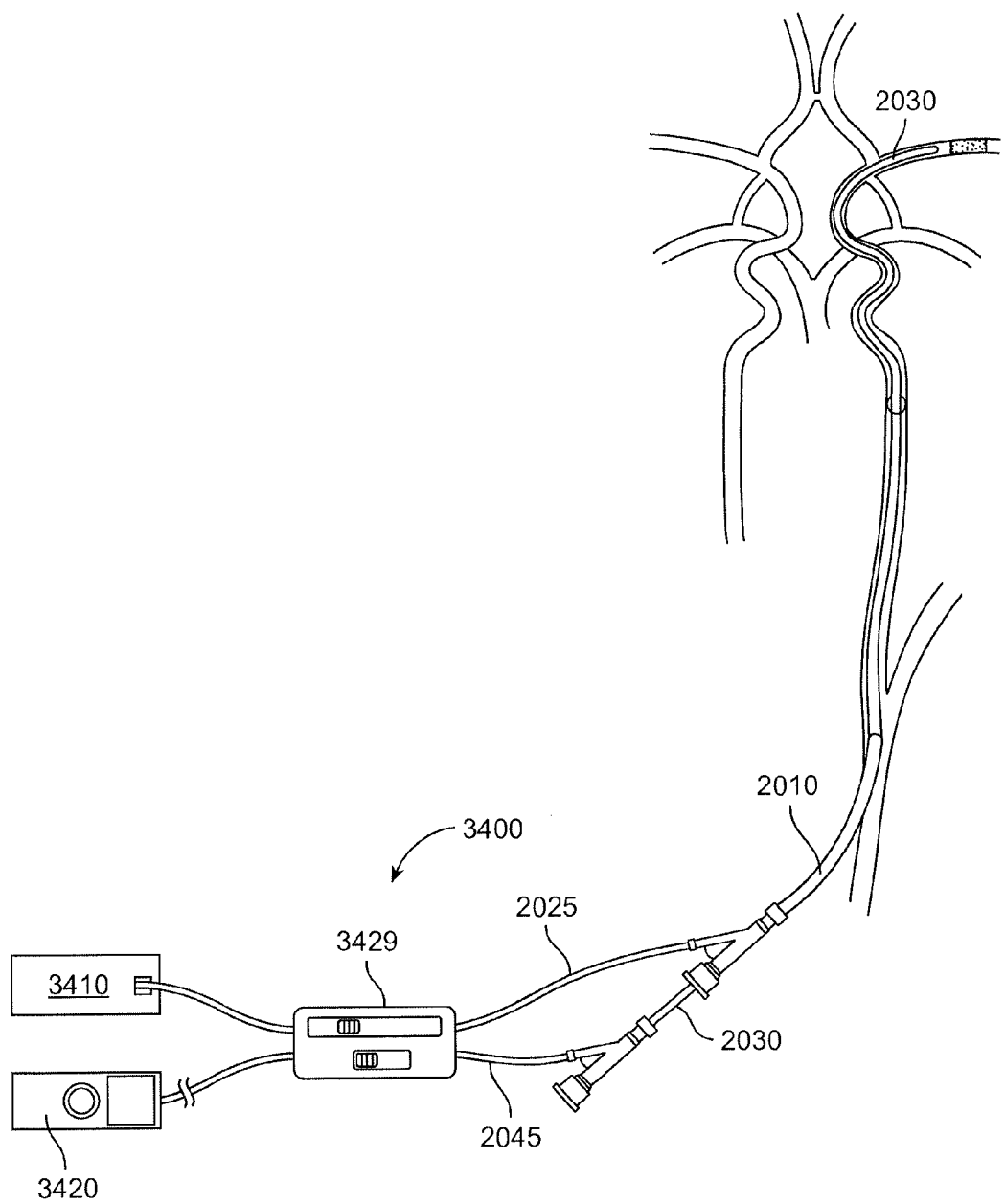

In an embodiment, a flow controller may facilitate control of multiple mechanisms of aspiration through multiple devices in a single unit. This configuration may facilitate use of the system by a single operator. The flow controller may include one or more control interfaces that a user may actuate to regulate which device is being aspirated, for example the arterial access device, the catheter, both, or neither. FIG. 35 shows an embodiment of a system that utilizes such a flow controller 3400. The flow controller 3400 is connected to the flow line 2025 of the arterial access device 2010 as well as to the flow line 2045 of the catheter 2030. In this manner, the flow lines 2025 and 2045 permit fluid to flow from the arterial access device 2010 and the catheter 2030, respectively, to the flow controller 3400. The controller 3400 may be connected to either or both a passive source of aspiration 3410 and an active source of aspiration 3420. The flow controller housing 3429 contains control mechanisms to determine how and when each device is connected to each source of aspiration. The control mechanisms may also control the level of aspiration from each source. In addition, the controller may include a control that permits a pulsatile aspiration mode which may facilitate the breaking up and aspiration of the cerebral occlusion. The flow controller may have an interface for switching between continuous and pulsatile aspiration modes. The control mechanisms may be designed to be operable using one hand. For example, the control mechanisms may be toggle switches, push button switches, slider buttons, or the like. In an embodiment, the flow controller 3400 has an interface that can enable the user to restore immediate antegrade flow to the cerebral circulation, for example with a single button or switch that simultaneously deflates the occlusion balloon on the arterial access device and stops aspiration.

The active source of aspiration may be an aspiration pump, a regular or locking syringe, a hand-held aspirator, hospital suction, or the like. In one embodiment, a locking syringe (for example a VacLok Syringe) is attached to the flow controller and the plunger is pulled back into a locked position by the user while the connection to the flow line is closed prior to the thrombectomy step of the procedure. During the procedure when the tip of the aspiration device (either the arterial access device or the catheter) is near or at the face of the occlusion, the user may open the connection to the aspiration syringe. This would enable the maximum level of aspiration in a rapid fashion with one user, something that is currently not possible with existing technologies. In another embodiment, the aspiration source is a hand-held aspirator which is configured to be able to aspirate and refill without disconnecting the aspiration device. In an example of this embodiment, the hand-held aspirator contains a chamber with a plunger that is moved up and down with a single-handed actuator. The chamber includes input and output valves, such that when the plunger is moved up and down there is a continuous source of aspiration into and out of the chamber without the need to remove and empty the chamber as would be needed with a syringe. The chamber input is connected to the catheter, and the chamber output is connected to a collection receptacle such as blood-collection bag. In an embodiment, this aspiration source is configured to be used with one hand only.

One disadvantage of current sources of aspiration is that the aspirated blood is received into an external reservoir or syringe. This blood is generally discarded at the end of the procedure, and as such represents blood loss from the patient. In addition, pumps such as centrifugal or peristaltic pumps are known to cause damage to blood cells. Although it is possible to return blood from the external reservoir to the patient, the blood has been exposed to air or has been static for a period of time, and there is risk of thrombus formation or damage to the blood cells. Usually, aspirated blood is not returned to the patient to avoid risk of thromboembolism.

Figure 36:
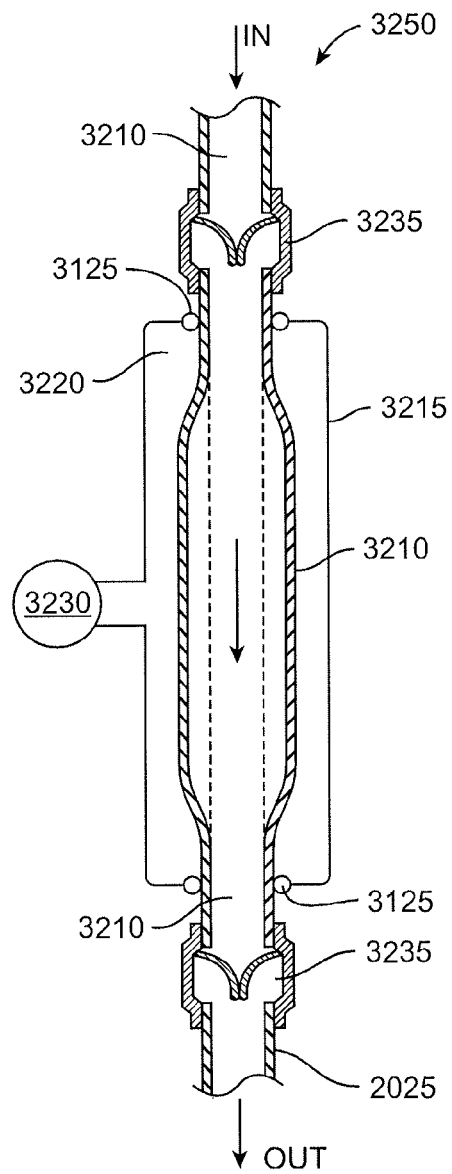
FIGS. 36 and 37 shows cross-sectional views of aspiration pump devices.

FIG. 36 shows a cross-sectional view of an exemplary aspiration pump device 3250 which is configured not to harm blood cells and which may be configured to return blood to the central venous system in real time during the procedure, so there is no reservoir in which the blood remains static. The pump 3250 may be connected to either or both the arterial access device 2010 and catheter 2030. The pump device 3250 includes a housing 3215 that encloses a chamber 3220 in which is contained a portion of the flow line 2025. An expandable portion 3210 of the flow line 2025 contained within the chamber 3220 is formed of an elastic material that is at a reduced diameter in its natural state (shown in phantom lines in FIG. 36) but may be configured to change to an expanded diameter (shown in solid lines in FIG. 36). One or more seals 3125, such as O-rings, seal the interface between the chamber 3220 and the flow line 2025. A vacuum source 3230 is coupled to the chamber 3220 and is configured to be operated to vary the pressure within the chamber 3220. Two one-way check valves 3235 are located in the flow line 2025 on either side of the expandable portion 3210.

In operation of the pump device 3250, the vacuum source 3230 is operated to create a reduced pressure within the chamber 3220 relative to the pressure within the flow line lumen 3210. The pressure differential between the chamber 3220 and the flow line lumen 3210 causes the expandable portion 3210 of the flow line 2025 to expand to an increased volume within the chamber 3220, as shown in solid lines in FIG. 41. This expansion causes blood to be pulled into the expandable portion 3210 from the sheath side of the flow line, shown by the "in" arrow, as controlled by the check valves 3235. The vacuum source 3230 may then be turned off so as to normalize the pressure within the chamber 3220. This causes the expandable portion 3210 to revert to its smaller, natural diameter, as shown in phantom lines in FIG. 36. The check valves 3235 causes the blood within the previously-expanded region of the flow line 2025 to be expelled towards location 3120, as shown by the "out" arrow in FIG. 36. The vacuum source 3230 may be operated so as to oscillate the expandable portion 3210 between the expanded and retracted state and together with the one-way check valves 3235 thereby drive fluid through the flow line lumen 3210.

Figure 37:
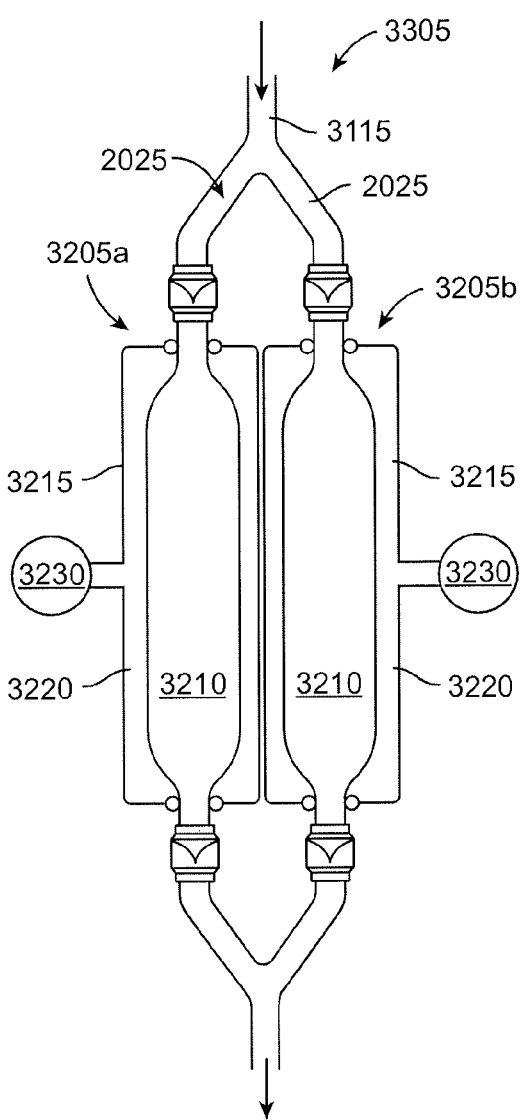

FIG. 37 shows a pump system 3305 that includes a pair of pump device 3205a and 3205b, each of which is of the type shown in FIG. 36. That is, each device 3205 includes a housing 3215 that contains a chamber in which a portion of the flow line 2025 is contained. The pump devices 3205a and 3205b are connected in parallel to the flow line 2025 such that each pump device 3205 has a flow line 2025 with an expandable portion 3210. The pair of pump devices 3205a and 3205b may be alternated between expanded and retracted states to create a relatively continuous flow state through the pump system 3305. For example, the pump device 3205a may be in the expanded state while the pump 3205b may be in the retracted state such that the pumps 3205a and 3205b are collectively driving fluid through the pump system 3305 without interruption.

A further advantage pump system 3250 or 3305 is that it may be used in conjunction with a passive reverse flow system which is configured to return blood to the central venous system, as is disclosed elsewhere in this document. These two systems may share a venous return line, and are connected by a valve or other flow control device.

Figure 38:
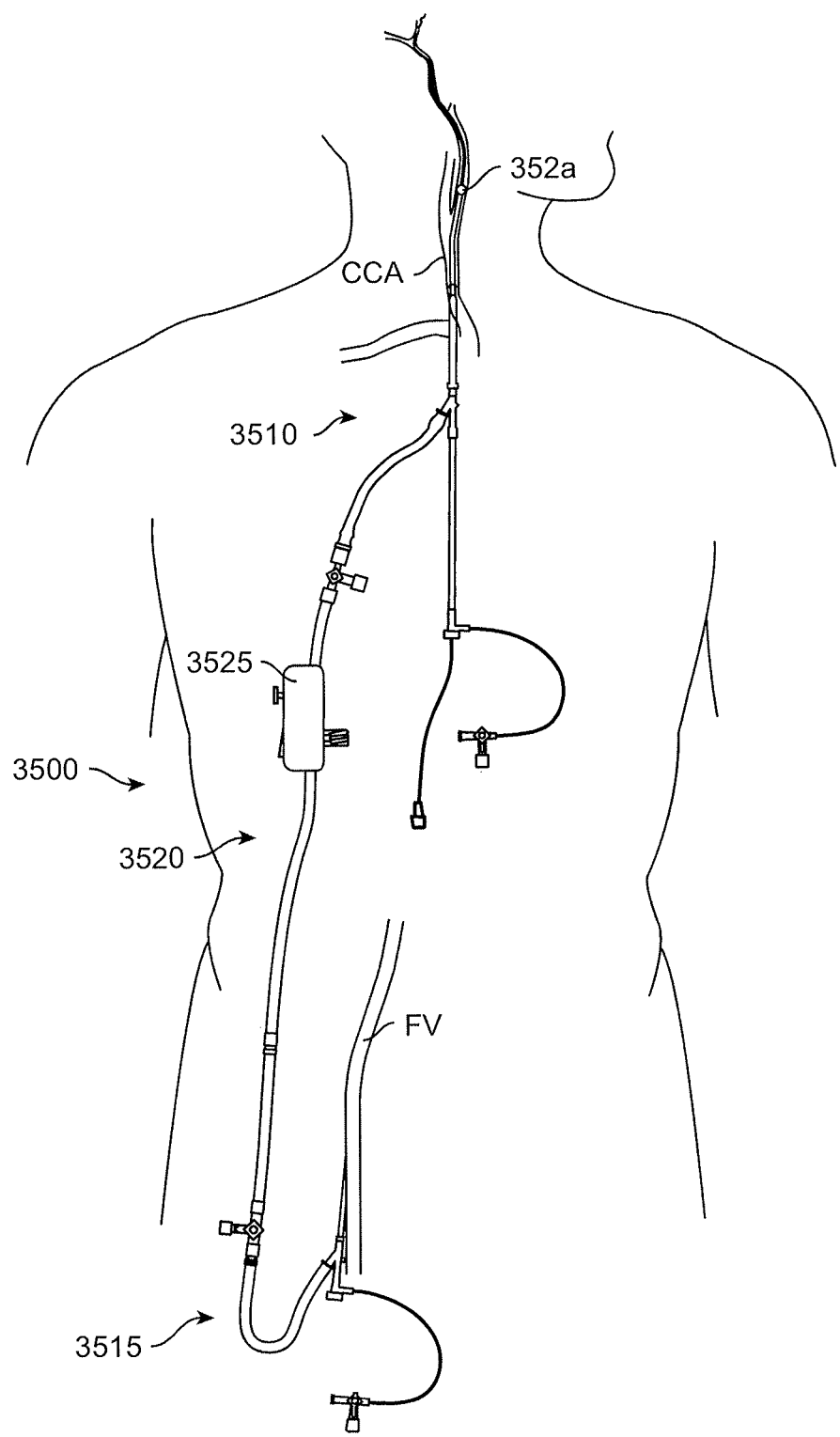
FIG. 38 shows an exemplary embodiment of a system that uses venous return to establish passive retrograde flow into the arterial access device.

The passive source of aspiration may be a site with lower pressure, for example a sheath inserted into a central vein (for venous return) or an IV bag placed at a vertical level that would vary depending on what amount of negative pressure is desired. FIG. 38 shows an exemplary embodiment of a system 3500 that uses venous return to establish passive retrograde flow into the arterial access device. The system 3500 includes the arterial access device 3510, a venous return device 3515, and a flow line 3520 that provides a passageway for retrograde flow from the arterial access device 3510 to the venous return device 3515. A flow control assembly 3525 interacts with the flow line 3520. The flow control assembly 3525 is adapted to regulate and/or monitor the retrograde flow through the flow line 3520. The flow control assembly 3525 interacts with the flow pathway through the flow line 3520 to determine the state and level of flow through the flow line.

In an embodiment, the arterial access device 3510 at least partially inserts into the common carotid artery CCA and the venous return device 3515 at least partially inserts into a venous return site, such as the femoral vein or internal jugular vein, as described in more detail below. The venous return device 3515 can be inserted into the femoral vein FV via a percutaneous puncture in the groin. The arterial access device 3510 and the venous return device 3515 couple to opposite ends of the flow line 3520 at connectors. The distal end of the arterial access device 3510 with the occlusion element 3529 may be positioned in the ICA. Alternately, in some circumstances where the ICA access is extremely tortuous, it may be preferable to position the occlusion element more proximally in the common carotid artery. When flow through the internal carotid artery is blocked (using the occlusion element 3529), the natural pressure gradient between the internal carotid artery and the venous system causes blood to flow in a retrograde or reverse direction from the cerebral vasculature through the internal carotid artery and through the flow line 3520 into the venous system.

In another embodiment, the arterial access device 3510 accesses the common carotid artery CCA via a transcarotid approach while the venous return device 3515 access a venous return site other than the femoral vein, such as the internal jugular vein. In another embodiment, the system provides retrograde flow from the carotid artery to an external receptacle, for example an IV bag, rather than to a venous return site. The arterial access device 3510 connects to the receptacle via the flow line 3520, which communicates with the flow control assembly 3525. The retrograde flow of blood is collected in the receptacle. If desired, the blood could be filtered and subsequently returned to the patient. The pressure of the receptacle could be set at zero pressure (atmospheric pressure) or even lower, causing the blood to flow in a reverse direction from the cerebral vasculature to the receptacle.

Exemplary Embodiments of Thrombectomy Devices

Figure 39:
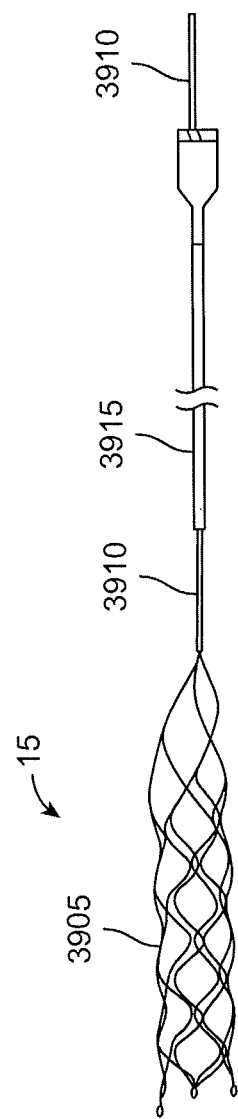
FIG. 39 shows an exemplary thrombectomy device.

FIG. 39 shows an exemplary embodiment of a thrombectomy device 15. In an embodiment, the device has been adapted for transcarotid access to the cerebral circulation. The device 15 includes an expandable member 3905 on a pusher wire 3910. The expandable member can be loaded in an unexpanded state into a delivery microcatheter 3915 which has already been positioned at or across the occlusion. The expandable member 3905 is advanced via pushing the pusher wire 3910 through the microcatheter 3915 and across the occlusion. Once positioned, the microcatheter 3915 is pulled back so that the expandable member 3905 can expand and engage the occlusion. The adaption of this device for transcarotid access method comprises shortening the working length of both the pusher wire 3910 and microcatheter 3915 by between 60 and 90 cm from the working lengths of devices adapted for transfemoral delivery. The thrombectomy device 15 has a working length that allows it to extend out of the arterial access device 2010 or catheter 2030 with enough length to access and cross the cerebral occlusion. More specifically, the thrombectomy device 15 has a working length of between 80 and 120 cm. Additionally, this adaption may comprise reducing the lengths of the distal flexible sections of the microcatheter 3915 to improve the deliverability of the device to the target site. The thrombectomy device 15 may be configured to remove an occlusion as a single piece by not breaking the occlusion into multiple pieces. This may minimize or eliminate the creation of emboli distal to the location of the clot. In an embodiment, once the expandable member 3905 is expanded at the location of the occlusion, the expandable member is maintained in that location for a period of time in order to create a perfusion channel through the occlusion that causes the thrombus to be lysed by the resultant blood flow passing through the thrombus. In such an embodiment, it is possible but not necessary that the expandable member 3905 capture a portion of the thrombus for retrieval outside the patient. When a sufficient portion of the thrombus has been lysed to create a desired flow channel through the obstruction, or outright removal of the obstruction is achieved by the resultant blood flow, the expandable member 3905 may be withdrawn into the catheter or access sheath and subsequently removed from the patient. The expandable portion may capture some or all of the thrombus while being withdrawn into the sheath.

It should be appreciated that other mechanical thrombectomy catheters may be used in a similar manner with the vascular access and reverse flow system as described above. Mechanical thrombectomy devices may coil-tipped retrievers, stent retrievers, expandable cages, wire or filament loops, graspers, brushes, or the like. These clot retrievers may include aspiration lumens to lower the risk of embolic debris leading to ischemic complications. Alternately, thrombectomy devices may include clot disruption elements such as fluid vortices, ultrasound or laser energy elements, balloons, or the like, coupled with flushing and aspiration to remove the thrombus. Some exemplary devices and methods are described in the following U.S. patents and Patent Publications, which are all incorporated by reference in their entirety: U.S. Pat. No. 6,663,650, U.S. Pat. No. 6,730,104; U.S. Pat. No. 6,428,531, U.S. Pat. No. 6,379,325, U.S. Pat. No. 6,481,439, U.S. Pat. No. 6,929,632, U.S. Pat. No. 5,938,645, U.S. Pat. No. 6,824,545, U.S. Pat. No. 6,679,893, U.S. Pat. No. 6,685,722, U.S. Pat. No. 6,436,087, U.S. Pat. No. 5,794,629, U.S. Patent Pub. No. 20080177245, U.S. Patent Pub. No. 20090299393, U.S. Patent Pub. No. 20040133232, U.S. Patent Pub. No. 20020183783, U.S. Patent Pub. No. 20070198028, U.S. Patent Pub. No. 20060058836, U.S. Patent Pub. No. 20060058837, U.S. Patent Pub. No. 20060058838, U.S. Patent Pub. No. 20060058838, U.S. Patent Pub. No. 20030212384, and U.S. Patent Pub. No. 20020133111.

Figure 40:
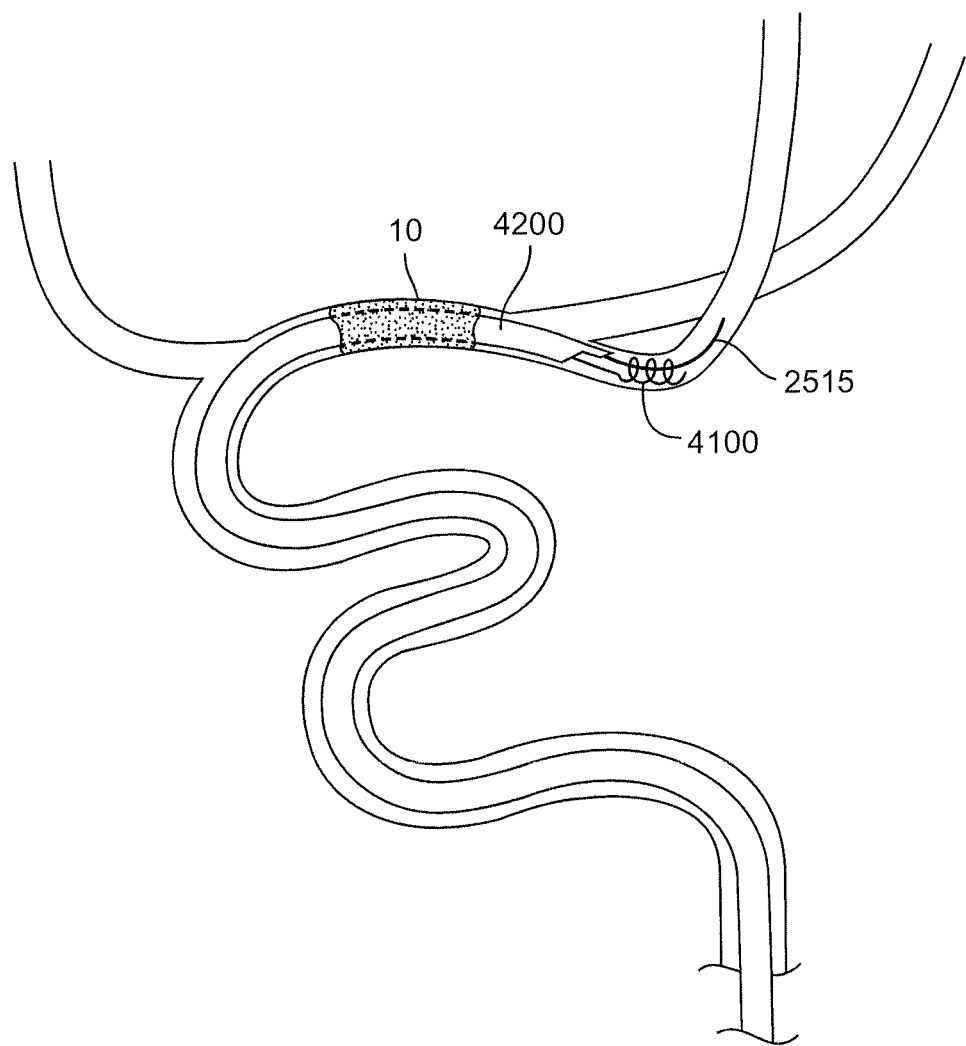
FIG. 40 shows a microcatheter that includes at least two lumens.

A major drawback to prior thrombectomy devices is the need to re-cross the occlusion with a guidewire and microcatheter if the thrombectomy device did not remove enough of the occlusion to restore adequate flow, and additional attempts are needed to remove the occlusion. Currently, a single-lumen microcatheter is used to deliver the thrombectomy device. The microcatheter is placed over a guidewire, the guidewire is then removed and the thrombectomy device is delivered. When removing the occlusion both the microcatheter and device are pulled back and the access across the occlusion is lost. Thus if the attempt at removal was unsuccessful or incomplete and an additional attempt is required, the guidewire and microcatheter must again cross the occlusion. As mentioned above, this extra step of re-crossing the occlusion takes time and incurs risk of distal vessel injury. An embodiment of this disclosure, shown in FIG. 40, is a microcatheter 4200 which includes at least two lumens, one lumen for a guide wire 2515 and the second to deliver a thrombectomy device 4100 such as a stentriever or coil retriever. The presence of a second lumen for the guide wire may add outer profile to a microcatheter over a microcatheter with just a single lumen. However, the reduced time and risk that may be provided by a second guidewire lumen can be advantageous. In addition, for use transcarotidly, the guidewire and/or the catheter walls may be scaled down to be less than conventional wall thicknesses, to lower the overall increase needed to add the extra lumen.

Exemplary Embodiments of Perfusion Devices

In an embodiment, the system may include a way to perfuse the cerebral vasculature distal to the thrombotic blockage and ischemic brain tissue via a perfusion catheter delivered, for example, through the arterial access device 2010 to a site distal to the thrombotic occlusion 10. The perfusion catheter is adapted to deliver a perfusion solution to a desired location. Perfusion solution may include, for example, autologous arterial blood, either from the flow line of a passive reverse flow circuit 3500 or from another artery, oxygenated solution, or other neuroprotective agent. In addition, the perfusion solution may be hypothermic to cool the brain tissue, another strategy which has been shown to minimize brain injury during periods of ischemia. The perfusion catheter may also be used to deliver a bolus of an intra-arterial thrombolytic agent pursuant to thrombolytic therapy. Typically, thrombolytic therapy may take up to 1-2 hours or more to clear a blockage after the bolus has been delivered. Mechanical thrombectomy may also take up to 1 to 2 hours to successfully recanalize the blocked artery. Distal perfusion of the ischemic region may minimize the level of brain injury during the stroke treatment procedure. Embodiments of distal perfusion are described below.

Figure 41:
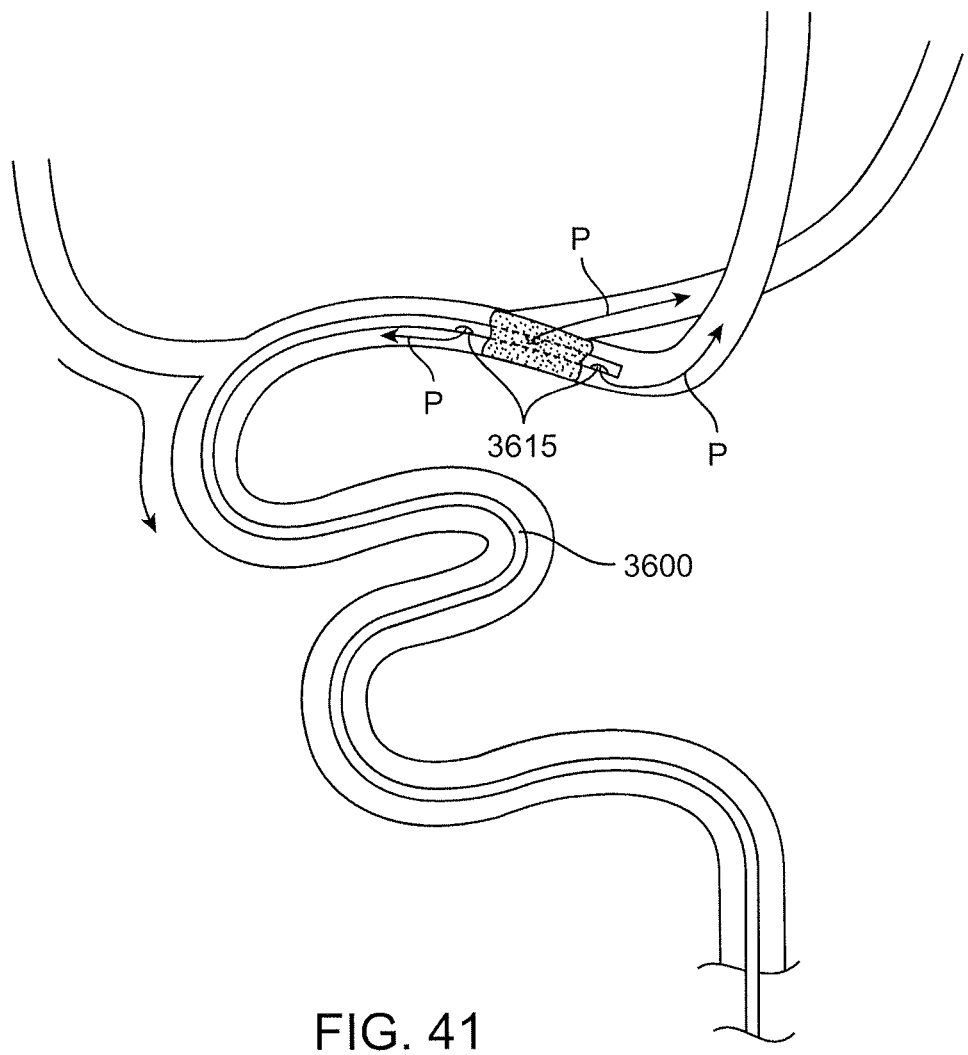
FIG. 41-42 illustrates embodiments of a distal perfusion catheter.

FIG. 41 shows a perfusion catheter 3600 positioned across the thrombotic blockage 10, to enable perfusion distal to the blockage. In an embodiment, the catheter is 3600 positioned over a guidewire placed through a lumen in the catheter. The lumen may serve as both a guidewire lumen and a perfusion lumen. Once placed, the guidewire may be removed to maximize the throughspace of the lumen available for perfusion. Alternately, the guidewire lumen and the perfusion lumen may be two separate lumens within the catheter, so that the guidewire may remain in place in the guidewire lumen during perfusion without interfering with the perfusion lumen. Perfusion exit holes 3615, which communicate with the perfusion lumen, are located in a distal region of the catheter 3600. This perfusion lumen may be connected to a perfusion source such as a perfusion pump or syringe and may be used for perfusing fluid such as neuroprotective agents and/or oxygenated blood such as the patient's own arterial blood via the perfusion exit holes 3615 as exhibited by the arrows P in FIG. 41, which represent the flow of perfusion solution out of the catheter 3600. Alternately, the catheter 3600 may be positioned relative to the blockage 10 such that the perfusion exit holes 3615 are initially positioned just proximal to, or within, the thrombotic blockage 10 during a bolus of thrombolytic infusion. The catheter can then be re-positioned so that at least some of the perfusion exit holes 3615 are located distal of the blockage 10 to provide distal perfusion with blood or an equivalent solution to the ischemic penumbra. The perfusion catheter may be used in conjunction with mechanical or aspiration thrombectomy as above. The catheter may be positioned through the lumen of access device 2010 or catheter 2030. The catheter may be placed side by side with mechanical thrombectomy element in the lumen, or may be co-axial with mechanical thrombectomy device.

Figure 42:
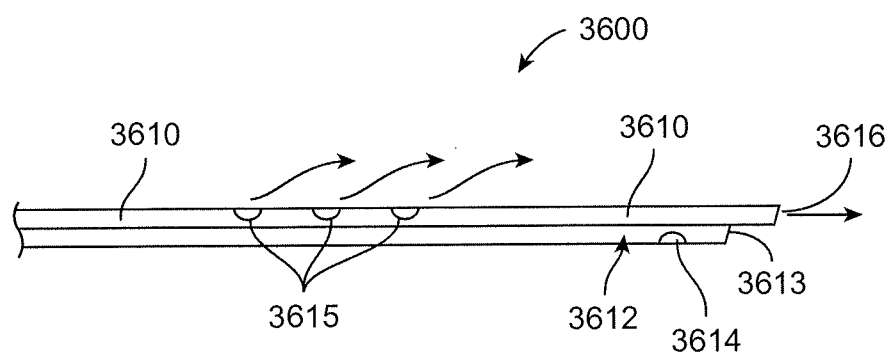

FIG. 42 shows another embodiment of a perfusion catheter 3600 with a perfusion lumen 3610 that communicates with side holes 3615 and/or an end opening 3616 for perfusing fluid, and a second lumen 3612 for pressure monitoring. The pressure monitoring lumen 3612 is closed off at a distal-most end 3613. A side opening 3614 to the lumen 3612 is located proximal of the distal-most end 3613 for measuring perfusion pressure. The catheter 3600 is shown without an expandable occlusion element although it could include an expandable occlusion element such as an occlusion balloon. The occlusion element may be positioned either distal to or proximal to the side holes 3615. In an embodiment, the perfusion source may be controlled by the perfusion pressure measurement to maintain perfusion pressure below 200 mm Hg. In an embodiment, the perfusion flow rate is controlled to maintain perfusion in the range of about 50 ml/min to about 250 ml/min.

Figure 43:
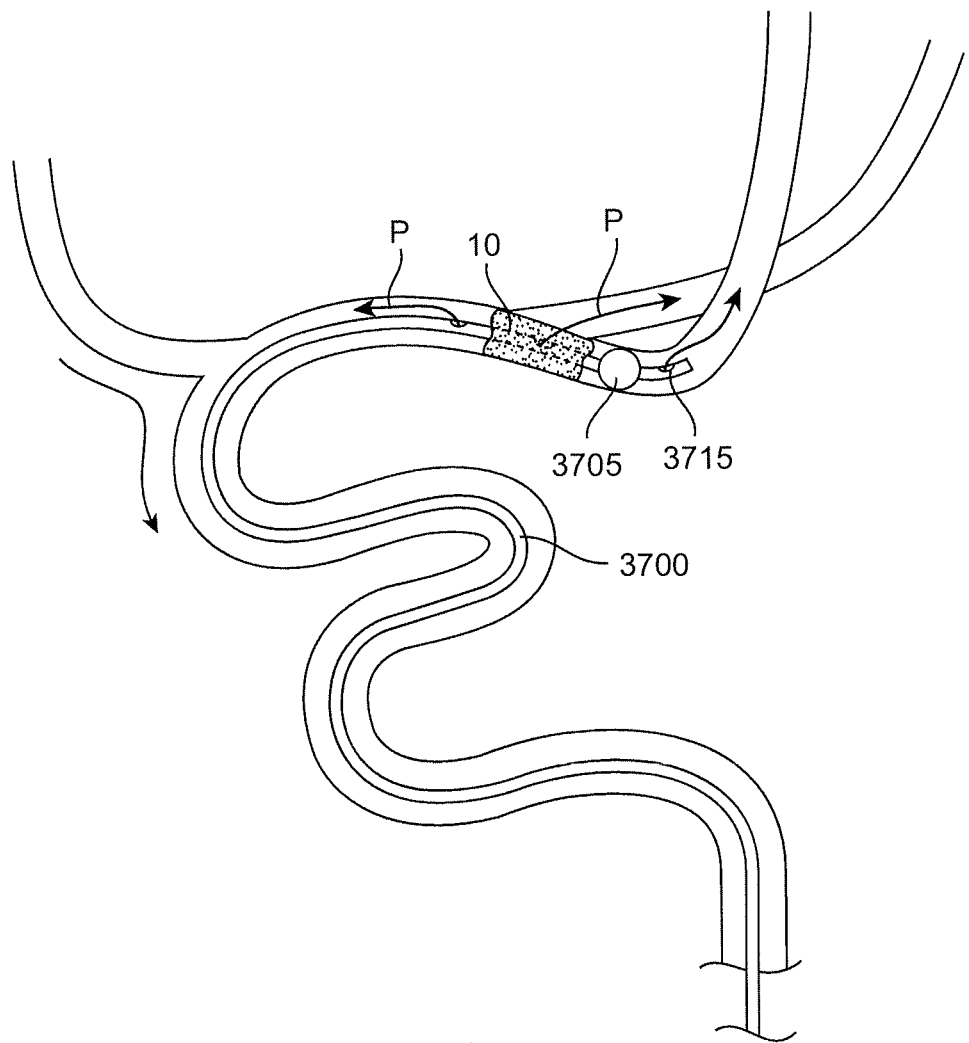
FIG. 43-45 illustrate different embodiments of distal perfusion catheters with an occlusion balloon.
Figure 44:
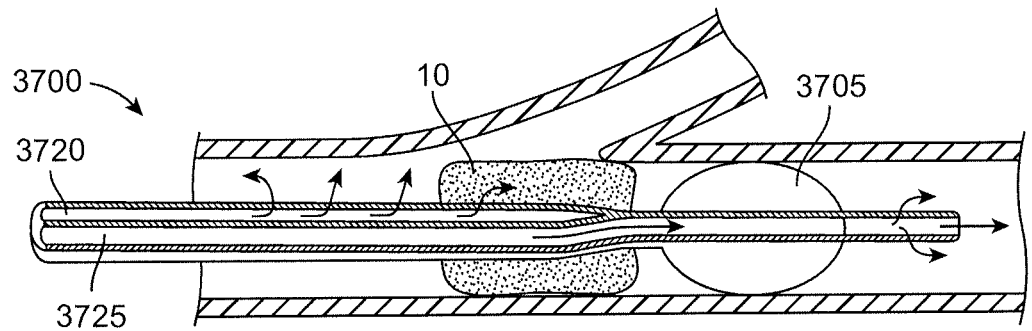
Figure 45:
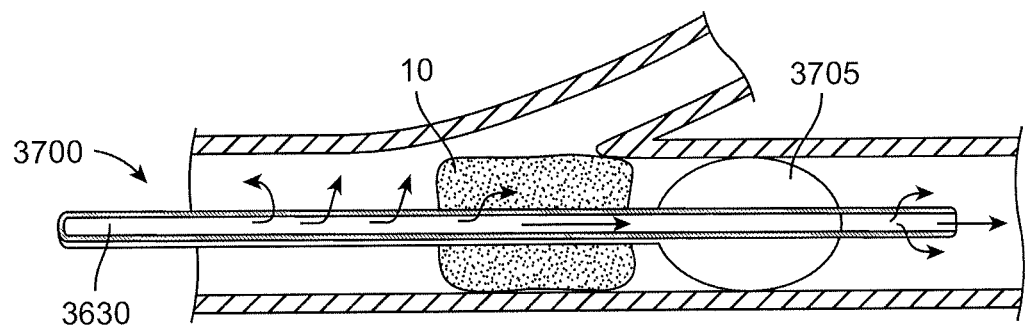

In an alternate embodiment, as shown in FIG. 43, distal perfusion catheter 3700 includes an occlusion balloon 3705, with perfusion exit holes 3715 positioned distal to, and/or proximal to the occlusion balloon 3705. As with the previous embodiment, the perfusion catheter 3700 may be used in conjunction with recanalization therapies such as thrombectomy devices, aspiration mechanism or intra-arterial thrombolytic infusion. The catheter 3700 is placed in the vasculature so that the occlusion balloon 3705 is positioned distal to the blockage 10. The catheter 3700 may be configured to perfuse the region distal of the balloon 3705 with blood or equivalent, and the region proximal of the balloon 3705 with thrombolytic agents. In this regard, the catheter 3700 may include separate perfusion lumens 3720 and 3725 that communicate with separate perfusion exit holes, as shown in FIG. 44. Alternately, as shown in FIG. 45, the distal and proximal perfusion exit holes are connected to the same perfusion lumen 3630, and regions both distal and proximal to the occlusion balloon are used to infuse blood or alternate perfusion solution. Not shown in either FIGS. 43 and 44 is a separate lumen for inflation and deflation of occlusion balloon 3705. This lumen may be embedded into the wall of the catheter.

Figure 46:
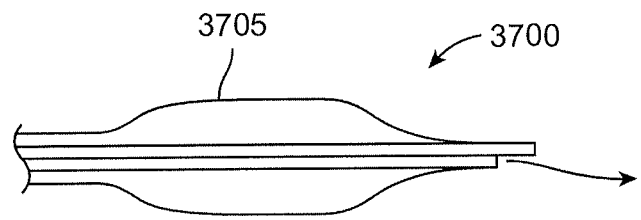
FIG. 46 shows a distal region of a perfusion catheter with an expandable device.

In another embodiment, as shown in FIG. 46, the expandable occlusion device 3705 is a dilatation balloon which may provide a dilatation force on the thrombus while the catheter 3700 is perfusing the distal vasculature.

Figure 47:
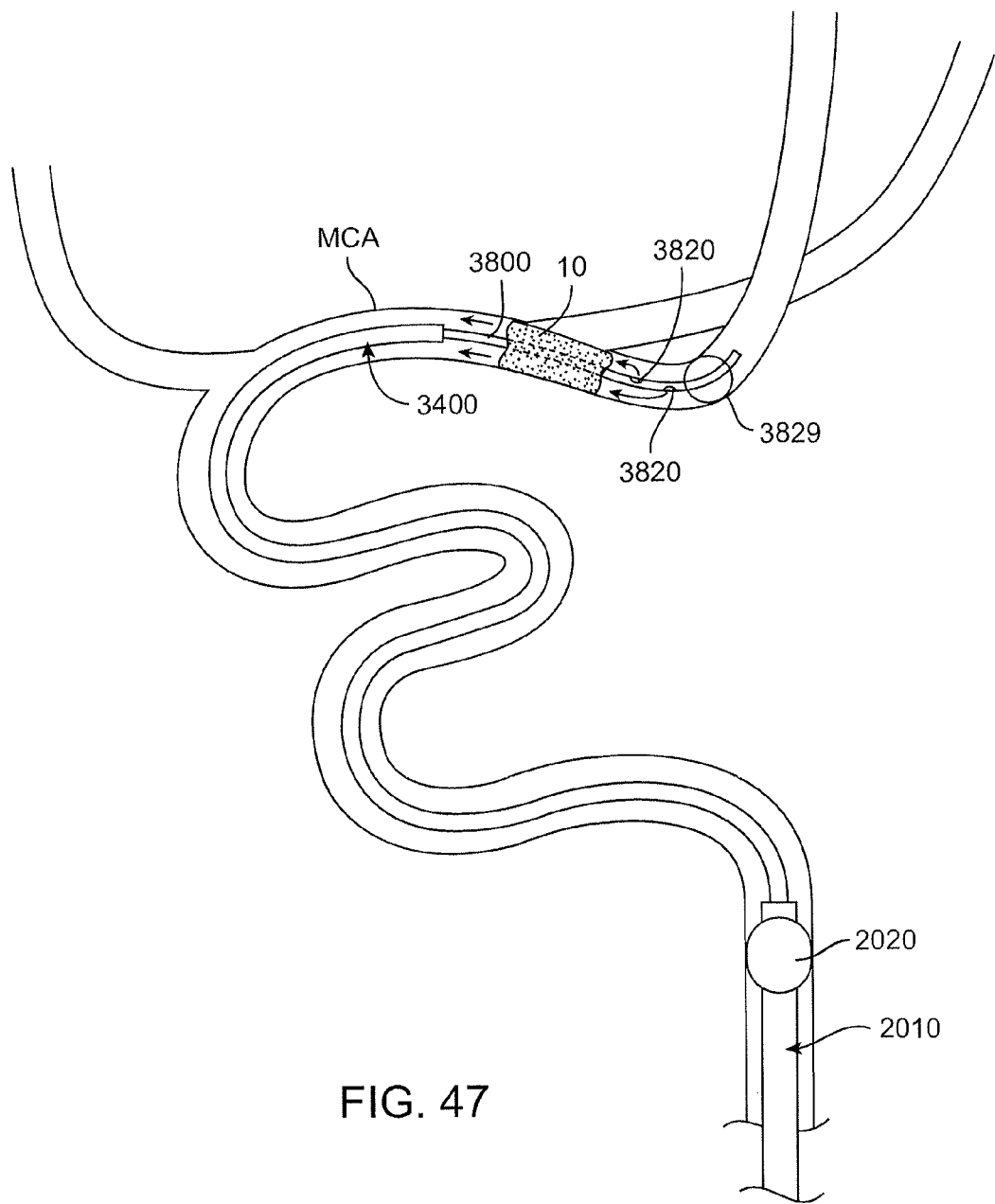
FIG. 47 shows a proximal perfusion catheter being deployed distal of the occlusion via the arterial access device or catheter.

The perfusion catheter may also provide perfusion to aid in thrombus removal. FIG. 47 shows a proximal perfusion catheter 3800 being deployed distal of the occlusion via the arterial access device 2010 or catheter 3401. The proximal perfusion catheter 3800 includes an expandable occlusion element 3829 such as an occlusion balloon. The proximal perfusion catheter 3800 also includes one or more perfusion exit holes 3820 at a location proximal to the occlusion element 3829. The perfusion exit holes 3820 communicate with an internal perfusion lumen in the perfusion catheter 3800 for perfusion of fluid out through the perfusion exit holes 3820. With reference still to FIG. 46, the proximal perfusion catheter 3800 is deployed into the vasculature via the arterial access device so that the occlusion element 3829 of the perfusion catheter is positioned and expanded distal to the thrombus 10 with the perfusion exit holes 3820 positioned proximal to the occlusion element 3829 and distal to the thrombus 10. Such an arrangement provides back pressure to assist in removal of the thrombus 10. In addition, the occlusion element 3829 serves as distal emboli protection. Any of a variety of perfusion fluids may be used including, for example, oxygenated blood, neuroprotection agents, thrombolytics, as well as other fluids, which may be adjusted to a desired temperature. The arterial access device 2010 can be used for aspiration in the arrangement of FIG. 47. The arterial access device 2010 may have occlusion balloon 2020 as well as passive or active aspiration mechanisms. The perfusion catheter facilitates removal of the thrombus into the arterial access device 2010 and thence through the flow line 2025 and out of the patient.

In addition to providing pressure distal to the occlusion, the perfusion fluid from proximal perfusion catheter 3800 can supply blood to smaller vessels (perforators) originating in or just proximal to the occlusion. The shaft of the perfusion catheter 3800 may also be used as a rail or conduit for delivery of a therapeutic device such as stentriever or thrombectomy device.

In an embodiment, the perfusion lumen and the guide wire lumen are two separate lumens, configured for example as in FIG. 42. In an alternate embodiment, the perfusion lumen of the perfusion catheter 3800 also serves as a guide wire lumen. In such an arrangement, a valve is desirably located at the distal end opening of the perfusion/guide wire lumen. When the guide wire is pushed distally out of the distal end opening of the guide wire lumen, the guide wire opens the valve. The valve automatically closes when the guide wire is retracted proximally back into the lumen. In this manner, the valve seals the distal end opening of the lumen after the guide wire is retracted. The valve can also be a pressure relief valve such that if the perfusion pressure is too high, the valve opens to release the pressure.

Figure 48A:
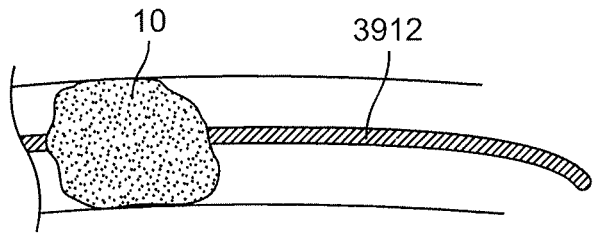
FIG. 48A-48D illustrates steps in usage of a distal balloon catheter configured to perfuse distal and/or proximal to the balloon.
Figure 48B:
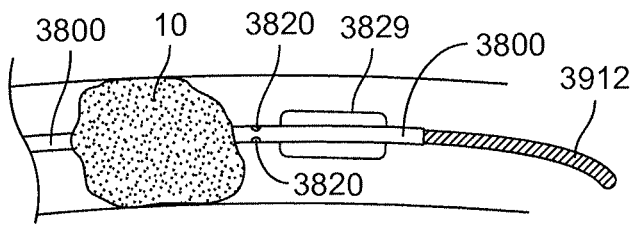
Figure 48C:
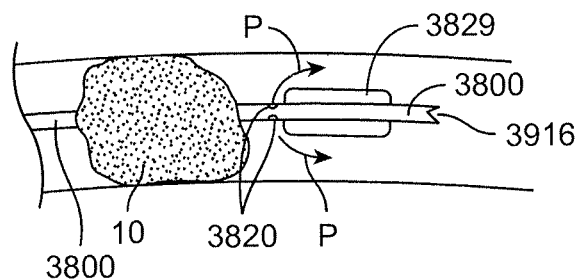
Figure 48D:
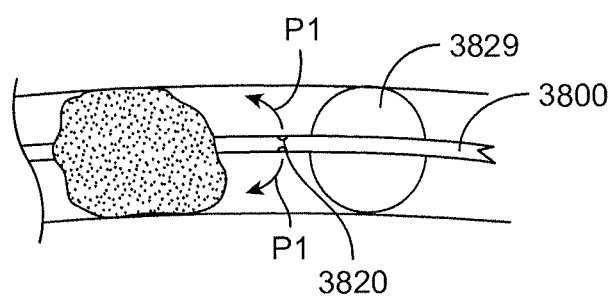

FIGS. 48A-48D show an exemplary method of use of proximal perfusion catheter 3800. FIG. 48A shows an enlarged view of a guide wire 3912 positioned across the thrombus 10 in a cerebral artery. In FIG. 48B, a distal region of the perfusion catheter 3800 has been positioned across the thrombus 10 (via the guide wire 3912) with the unexpanded occlusion element 3829 positioned distal of the thrombus 10. The guide wire 3912 protrudes out of the distal end of the guide wire lumen of the perfusion catheter 3800. In FIG. 48C, the guide wire is not shown as it has been retracted back into the guide wire lumen of the perfusion catheter 3800. If the guide wire lumen also serves as a perfusion lumen for the perfusion catheter 3800, a distal valve 3916 (such as a duckbill valve) at the distal end of the guide wire/perfusion lumen has automatically closed such that the lumen can now be used for perfusion via the perfusion exit holes 3820, as represented by the arrows P in FIG. 48C. When the occlusion element 3829 is unexpanded (as shown in FIG. 48C), the perfusion exit holes 3820 can be used to perfuse distally. In FIG. 48D, the expandable occlusion element 3829 has been expanded in the artery. The perfusion exit holes 3820 can then be used for perfusion proximal of the occlusion element 3829, as represented by the arrows P1 in FIG. 48D.

Perfusion catheters 3600 or 3800 may include an element for monitoring blood pressure. In an embodiment, the pressure monitoring element is a dedicated internal lumen in the perfusion catheter 3600 or 3800, wherein the lumen is fluid-filled and connected to a pressure transducer on the proximal end of the perfusion catheter. A pressure transducer on the catheter itself may also be used. Alternately, a pressure measuring guide wire may be inserted through an internal lumen of the perfusion catheter 3600 or 3800 to a location where pressure is to be monitored.

Alternatively, cerebral perfusion can include cerebral retroperfusion as described by Frazee et al. This embodiment involves selective cannulation and occlusion of the transverse sinuses via the internal jugular vein, and infusion of blood via the superior sagittal sinus to the brain tissue, during treatment of ischemic stroke. The following articles, which are incorporated herein by reference in their entirety, described cerebral retroperfusion and are incorporated by reference in their entirety: Frazee, J. G. and X. Luo (1999). "Retrograde transvenous perfusion." Crit Care Clin 15(4): 777-88, vii.; and Frazee, J. G., X. Luo, et al. (1998). "Retrograde transvenous neuroperfusion: a back door treatment for stroke." Stroke 29(9): 1912-6. This perfusion, in addition to providing protection to the cerebral tissue, may also cause a retrograde flow gradient in the cerebral arteries. Used in conjunction with the system 100, a retroperfusion component may provide oxygen to brain tissue, as well as aid in capture of embolic debris into the reverse flow line during recanalization of the thrombotic occlusion 10.

It should be appreciated that other perfusion catheters or systems may be used with the system 100, for example those described by U.S. Pat. Nos. 6,435,189 and 6,295,990, which are incorporated by reference in their entirety.

Exemplary Methods and Devices for Transcarotid Vessel Closure

Any type of closing element, including a self-closing element, a suture-based closing element, or a hydrostatic seal element, may be deployed on or about the penetration in the wall of the common carotid artery prior to withdrawing the arterial access device 2010 at the end of the procedure. Described herein are vessel closure methods and devices that have been specifically configured for transcarotid vessel closure. The following U.S. Patent Applications, which are incorporated herein by reference in their entirety, describe exemplary closure devices and methods: U.S. Patent Publication No. 20100042118, entitled "Suture Delivery Device", and U.S. Patent Publication No. 20100228269, entitled "Vessel Closure Clip Device". Additional examples of transcarotid vessel closure devices and methods are described in U.S. Provisional Application Ser. No. 61/994,623, filed May 16, 2014, which is incorporated by reference herein in its entirety. U.S. Provisional Application Serial No. 62/074,964 entitled "Vessel Access and Closure Assist System and Method" and filed Nov. 4, 2014 and U.S. patent application Ser. No. 12/540,341 entitled "Suture Closure Device" are also incorporated herein by reference in their entirety.

The closing element may be deployed at or near the beginning of the procedure in a step termed "pre-closure", or, the closing element could be deployed as the sheath is being withdrawn. In an embodiment, vessel closure can be accomplished by a suture-based blood vessel closure device. The suture-based vessel closure device can place one or more sutures across a vessel access site such that, when the suture ends are tied off after sheath removal, the stitch or stitches provide hemostasis to the access site. The sutures can be applied either prior to insertion of the procedural sheath through the arteriotomy or after removal of the sheath from the arteriotomy. The device can maintain temporary hemostasis of the arteriotomy after placement of sutures but before and during placement of a procedural sheath, if a pre-closure step us used, and can also maintain temporary hemostasis after withdrawal of the procedural sheath but before tying off the suture. Some exemplary suture-based blood vessel disclosure devices are described in the following U.S. patents, which are incorporated herein by reference in their entirety: U.S. Pat. Nos. 6,562,052; 7,001,400; and 7,004,952.

In an embodiment, the system includes an ultrasound probe element, which when used with an ultrasound imaging system is configured to identify the desired site of carotid arterial access to determine that is suitable for percutaneous puncture, for example to verify that there is no vascular disease in the vessel. The probe will also visualize surrounding anatomy such as the internal jugular vein, to ensure that access can be achieved without comprising these other structures. In addition, the probe may be used to visualize the access site after vessel closure to verify that hemostasis has been achieved. If needed, the probe may be used to provide localized compression at the site of the puncture as needed to ensure hemostasis. For example, after vessel closure the probe is used to image the closure site. If blood is seen flowing from the site, the probe is pressed down to compress the site. The user periodically relaxes the pressure on the probe to assess if hemostasis has been achieved. If it has not, pressure is reapplied. If it has, the probe may be removed.

Figure 49:
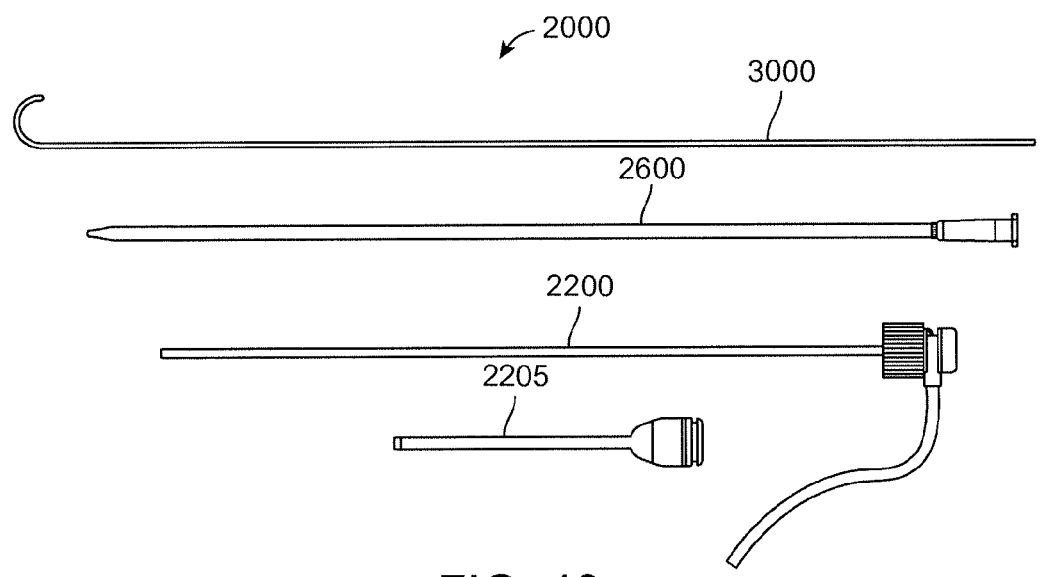
FIGS. 49-50 shows an embodiment of an arterial access system which facilitates usage of a vessel closure device.
Figure 50:
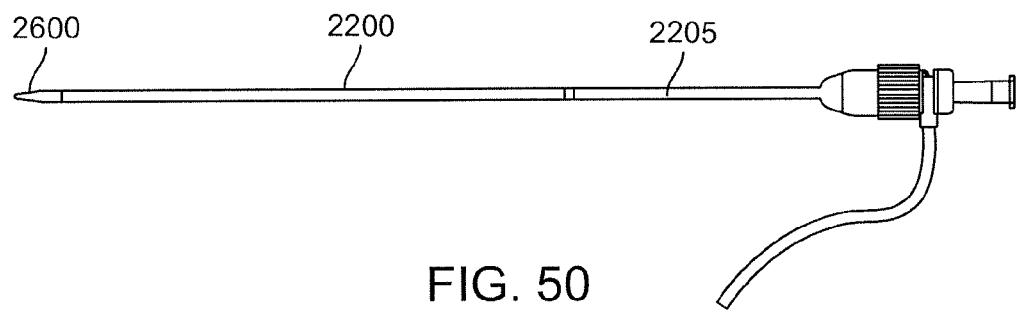

In an embodiment shown in FIG. 49 the arterial access system 2000 includes devices to facilitate the delivery of a vessel closure device onto a blood vessel for closing the opening in the wall of the blood vessel. In an embodiment, the system 2000 is packaged as a kit that includes a procedural introducer sheath 2200, a sheath dilator 2600, an introducer guide wire 3000, and a vessel closure device delivery sheath 2205. In an embodiment, the kit also includes a vessel closure device applier. In an embodiment, the vessel closure device delivery system is configured for use in a transcarotid procedure performed at least partially on a blood vessel located in the neck of a patient, such as the carotid arteries including the common carotid artery. FIG. 50 shows the arterial access system 200 assembled for insertion over the guidewire 3000 into the artery.

Exemplary Methods of Use

As illustrated in FIG. 1, the arterial access device 2010 is transcarotidly introduced directly into the common carotid artery CCA of the patient. This may be done with a percutaneous puncture or a direct cut-down. In the case of a puncture, ultrasound imaging may be used to accurately make the initial arterial puncture. The arterial access device 2010 is threaded through the vasculature such that the distal tip is positioned in the common carotid artery or the proximal or distal cervical, petrous, or cavernous portion of the internal carotid artery ICA. A removable proximal extension may be used to place the arterial access device 2010 under fluoroscopy without exposing the user's hand to radiation. U.S. Patent Publication No. 2011/0034986, filed Jul. 12, 2010, describes exemplary embodiments of removable proximal extensions and is incorporated herein by reference.

Once the arterial access device is positioned, a diagnostic angiogram may be performed via a microcatheter which has been configured for transcarotid access and which is placed through the arterial access device. Diagnostic angiograms are performed throughout the procedure to determine the progress of the procedure.

A catheter 2030 is placed through the arterial access device 2010 or the guide catheter 2105 and positioned such that the distal tip reaches the treatment site. If desired, a coaxial system of devices comprising a guide wire, a microcatheter, and the catheter 2030 are inserted together through the arterial access device 2010 and advanced towards the treatment site. Alternately, a tapered dilator with or without a microcatheter tip may be substituted for the microcatheter. Alternately, a microcatheter and guide wire may be placed inside the tapered dilator. The removable proximal extension, if used, may be removed prior to introduction of the telescoping devices, or the devices may be inserted through the removable proximal extension. The microcatheter, or tapered dilator, and guide wire are then advanced to access and cross the cerebral occlusion. The microcatheter or dilator may be used to perform the angiogram of the cerebral circulation proximal and distal to the occlusion. The microcatheter may also used as a rail to advance the catheter.

Typically, the largest size catheter will be selected which is able to be safely navigated to the occlusion, to maximize the force and luminal area for aspiration of the occlusion. Aspiration is then initiated through the catheter. This may be done manually, with an aspiration pump, or with another aspiration source, or via the flow controller as described above. If the thrombus is too large or too strongly embedded into the vasculature such that it is not possible to remove the occlusion via aspiration alone, further steps are taken to remove the occlusion. A thrombectomy device 15 may be deployed through the arterial access device to remove the clot. During clot retrieval, passive or active aspiration may be applied via the arterial access device, or the guide catheter to minimize or eliminate the amount of distal emboli.

If the catheter is unable to reach the treatment site, or if a secondary more distal treatment site needs to be reached after removal of a first occlusion, a second, smaller diameter catheter may be inserted through the first catheter, and positioned at the distal treatment site. Alternately, the first catheter may be removed and exchanged for the second catheter. A guidewire and/or microcatheter may be placed through the first catheter to facilitate the exchange.

Figure 26:
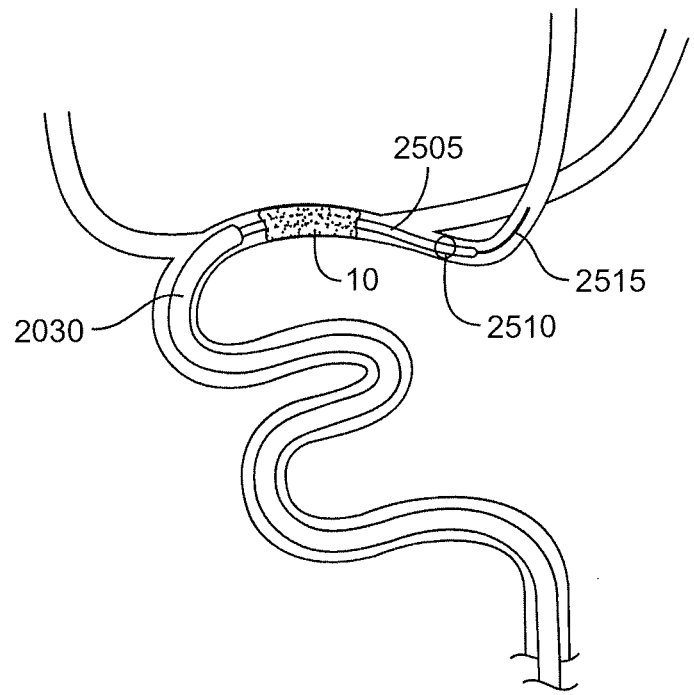
FIG. 26 shows an example of a microcatheter with an anchor device.

If there is difficulty navigating the catheter of the desired size to the treatment site, a device may be deployed distal to the site and expanded to act as an anchor to aid in advancing the catheter as shown in FIGS. 26 and 27. If desirable, a second catheter may be used in a telescoping manner to create support for the first catheter to access the proximal face of the occlusion. Alternately, a tapered dilator as shown in FIG. 25A or FIG. 25B may be used in addition to or in place of the microcatheter to facilitate navigation of the catheter. The arterial access device 2010 and the catheter 2030 may be connected to an element for passive or active aspiration, as shown in FIGS. 32-34, or a flow controller 3400 as shown in FIG. 35. In one embodiment, the arterial access device 2010 is connected to passive aspiration and the catheter 2030 is connected to active aspiration. In another embodiment, both devices are connected to active aspiration. During the procedure, the user may open or close the connections to the passive and/or active aspiration sources as desired.

At any time during the procedure, a balloon on the arterial access device 2010 may be inflated at this point to reduce forward arterial pressure on the occlusion. The inflated balloon may also increase the stability of the arterial access in the vessel to increase the support for advancement of devices through the arterial access device. Additionally, the arterial access device 2010 or guide catheter 2015 may be connected to passive or active aspiration as desired to provide embolic protection while not compromising perfusion of the brain. This may be accomplished by selective periods of reverse, stopped, and antegrade flow. At the conclusion of the procedure, the arterial access sheath may be closed by methods as described previously. Ultrasound may again be employed, in this instance to ascertain and/or ensure hemostasis. If appropriate, the ultrasound probe may be used to apply pressure at the access site until hemostasis is achieved.

In a variation of this procedure, a guide catheter 2105 is inserted through the arterial access device 2010 which has been previously inserted into the CCA, as shown in FIG. 3. In this scenario, the guide catheter 2105 may be removed and cleared onto a table during the procedure or may be exchanged for another size or type of catheter as needed without loss of arterial access. In addition, there is no need to exchange the sheath at the conclusion of the procedure before utilizing a vessel closure device. The arterial access device 2010 may incorporate a proximal extension such that during the procedure there is limited exposure of radiation to the users' hands. In an embodiment, the proximal extension is removable and is removed prior to closure of the access site with a vessel closure device.

In yet a further embodiment, the system is used to provide distal protection and/or perfusion during the procedure. In this embodiment, a perfusion catheter is inserted through the arterial access device 2010 or through the catheter 2030, and positioned across the lumen and inflated at a point distal to the occlusion. The perfusion catheter may be connected to a perfusion pump to perfuse oxygenated blood or perfusion solution to the ischemic brain via a distal opening in the perfusion catheter. In an embodiment, the perfusion catheter is a balloon-tipped catheter. The balloon is inflated at a point distal to the occlusion. This balloon acts to prevent emboli from progressing distally during removal or recanalization of the occlusion. The perfusion catheter may also be connected to a flush source to perfuse proximal to the occlusion balloon via proximal ports in the perfusion catheter. This maneuver essentially provides a back pressure on the occlusion and may aid it its removal.

In the instance where there is also a carotid artery stenosis which requires treatment either before or after treatment of the cerebral occlusion, an angioplasty balloon or stent may be deployed in the stenosis via the introducer sheath. If embolic protection is desirable during intervention of the carotid stenosis, the introducer sheath may have an occlusion balloon and a connection to a reverse flow line as shown in FIG. 38, and the CAS procedure may be conducted under reverse flow embolic protection as described in U.S. Pat. No. 8,157,760, which is incorporated herein by reference. Alternately, the arterial access device 2010 may have two occlusion balloons as shown in FIG. 12, with an opening to allow balloon angioplasty or stenting of the carotid stenosis, and subsequent introduction of devices such as a catheter into the ICA and cerebral circulation for treatment of the cerebral or intracranial arteries.

In yet another method of use, a telescoping system as depicted in FIG. 31A is used to access and aspirate a cerebral occlusion in a rapid fashion, from either a transfemoral or transcarotid access site. A puncture is first formed in an artery at an arterial access site, and a sheath guide wire is inserted into the artery. The arterial access device with a tapered dilator are inserted into the artery over the sheath guide wire. For the carotid artery access method, the arterial access device, sheath and sheath guide wire are designed for transcarotid access. The arterial access device 2820 is then advanced and the distal tip is positioned in the common or internal carotid artery. The sheath and guidewire are then removed. If the arterial access device has an occlusion element 2815, at any point in the procedure the occlusion element may be inflated to occlude the common or internal carotid artery to reduce the risk of distal emboli to cerebral vessels. A telescoping catheter 2830 is positioned through the lumen of the arterial access device to a target occlusion site. The catheter 2830 may be pre-assembled with a guide wire to aid in positioning, and inserted as a system into the access device 2820. Alternately, the guide wire is placed first across the occlusion site and the catheter is back-loaded onto the guide wire and into the sheath. The catheter may also be pre-loaded onto a microcatheter or tapered inner member such as that depicted in FIG. 8 or 9, and the system inserted into the access device 2820 and thence into the carotid vasculature and advanced to the occlusion site. Once the catheter is positioned at the occlusion site, the overlap region and/or sealing element between the catheter and the access device provides a seal between the two devices. All internal devices such as guidewires, microcatheters, or tapered inner members are removed. Aspiration is applied to a side arm of the arterial access device, for example via side arm 2027 as shown in FIG. 1. Aspiration may be via a syringe, a pump, or other means as disclosed above. If the occlusion is soft enough, aspiration is sufficient to remove the occlusion through the catheter and arterial access device and into the aspiration device via a side arm 2027 on the arterial access device. If the occlusion is too hard to be completely removed in this manner but is "corked" or otherwise caught into the distal end and/or distal lumen of the catheter 2830 via the aspiration force, the occlusion may be removed by pulling back on the catheter 2830. As this maneuver may increase the risk of distal emboli, it may be a desirable time to inflate the occlusion element 2815 on the access device as described above. Once the clot has been pulled completely into the lumen of the access device 2820, the catheter 2830 may be removed rapidly from the access device 2830. If the clot detaches from the catheter 2830 during this step, it may be removed easily through the larger lumen of the arterial access device via the side arm 2027. Because the clot may be protruding from the distal tip of the catheter by as much as several centimeters, the user may want to pull the distal marker of the catheter several centimeters into the arterial access device before rapid removal of the catheter.

This method provides speed and ease of use benefits over traditional configuration wherein the aspiration is applied via a catheter which is inserted the entire length of the arterial access device. For this traditional configuration, aspiration is applied directly to the proximal end of the catheter, and must be applied during the entire time the catheter is being removed from the access device. Likewise the catheter must be removed very slowly, otherwise there is risk that the clot is lost and either lodged back in the vasculature or in the access device. In contrast, for the telescoping method, direct aspiration to the occlusion may be applied via the arterial access device rather than the catheter, and therefore once the clot is entered into the access device the catheter may be rapidly removed. This difference may halve or even further reduce the time for each "pass" of an aspiration attempt. For many stroke procedures, more than one pass is required to completely remove the occlusion Furthermore, the fact that the back half of the aspiration lumen is the larger lumen of the access device rather than the smaller lumen of the catheter makes aspiration more effective. It will be more likely that the clot can be suctioned without "corking" at the tip or in the lumen of the catheter, and increase the rate of aspiration into the aspiration device.

In a variation of this method, a stentriever or similar device may be used as an adjunct to aspiration to remove the occlusion. It may be used initially before placement of the catheter to provide immediate perfusion through the occlusion, may be used to help provide counter-traction and rail support during positioning of the catheter, may aid in dislodging the clot into the catheter, or some or all of the above.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Therefore the spirit and scope of the appended claims should not be limited to the description of the embodiments contained herein.

The invention claimed is:

1. A system of devices for treating an artery, comprising:
an arterial access sheath adapted to introduce an interventional catheter into an artery, the arterial access sheath including a sheath body sized and shaped to be introduced into a common carotid artery via a carotid artery access site, the sheath body defining an internal lumen that provides a passageway for introducing a catheter into the common carotid artery when the sheath body is positioned in the common carotid artery, wherein the sheath body has a proximal section and a distalmost section that is more flexible than the proximal section, and wherein a ratio of an entire length of the distalmost section to an overall length of the sheath body is one tenth to one half the overall length of the sheath body;

a tubular, proximal extension having an internal lumen and being connected to a proximal-most end of the sheath body, the proximal extension having a hemostasis valve that provides access to the internal lumen of the proximal extension, wherein the internal lumen of the proximal extension fluidly communicates with the internal lumen of the sheath body when the proximal extension is connected to the sheath body, wherein the proximal extension has an inner diameter and an outer diameter that is larger than an inner diameter and an outer diameter, respectively, of the sheath body so as to form a step between the sheath body and the proximal extension;

an elongated dilator positionable within the internal lumen of the sheath body, wherein the arterial access sheath and the dilator can be collectively introduced into the common carotid artery; and a first catheter formed of an elongated catheter body having an internal lumen and sized and shaped to be introduced via a carotid artery access site into a common carotid artery through the internal lumen of the arterial access sheath, the catheter body sized and shaped to be navigated distally to an intracranial artery through the common carotid artery via the access location in the carotid artery, wherein the catheter body has a length of 40 cm to 70 cm, and wherein the catheter body has a proximal most section and a distal most section wherein the proximal most section is a stiffest portion of the catheter body, and wherein the catheter body has an overall length and a distal most section length such that the distal most section can be positioned in an intracranial artery and at least a portion of the proximal most section is positioned in the common carotid artery during use;

a second catheter having a tubular distal region that fits co-axially into the internal lumen of the first catheter, the tubular distal region having an outer seal that seals with the internal lumen of the first catheter, the second catheter further having a proximal tether wire attached to the tubular distal region and extending in a proximal direction from the tubular distal region, the tether wire being be of sufficient rigidity to push the catheter without buckling.

2. A system as in claim 1, wherein the distal most section of the catheter body is 5 cm to 15 cm in length.

3. A system as in claim 1, wherein the catheter can achieve an aspiration rate of greater than at least 85% in aspiration rate over a catheter having a length of 115 cm and an internal lumen with a diameter of 0.058 inch, wherein aspiration rate is calculated pursuant to Poiseuille's law for laminar flow in a tube for a fluid having the viscosity of human blood at body temperature.

4. A system as in claim 1, wherein the interventional catheter can achieve an aspiration rate of greater than at least 71% in aspiration rate over a catheter having a length of 105 cm and an internal lumen with a diameter of 0.072inch, wherein aspiration rate is calculated pursuant to Poiseuille's law for laminar flow in a tube for a fluid having the viscosity of human blood at body temperature.

5. A system as in claim 1, wherein the catheter body achieves an actual aspiration rate of at least 205 ml/min for a fluid having the viscosity of human blood at body temperature.

6. A system as in claim 1, wherein the catheter body achieves an actual aspiration rate of at least 321 ml/min for a fluid having the viscosity of human blood at body temperature.

7. A system as in claim 1, wherein the interventional catheter can achieve an actual aspiration rate of greater than at least 59% in aspiration rate over a catheter having a length of 115 cm and an internal lumen with a diameter of 0.058 inch.

8. A system as in claim 1, wherein the interventional catheter can achieve an actual aspiration rate of greater than at least 23% in aspiration rate over a catheter having a length of 105 cm and an internal lumen with a diameter of 0.072 inch.

9. A system as in claim 1,
wherein the sheath body is stepped such that a distal region of the sheath body has a reduced diameter relative to a larger diameter proximal region of the sheath body; and
wherein the catheter body is also stepped such that a distal region of the catheter body has a reduced diameter relative to a larger diameter proximal region of the catheter body.

10. A system as in claim 9, wherein both an inner diameter and outer diameter of the catheter body is stepped.

11. A system as in claim 9, wherein the larger diameter proximal region of the catheter body has a diameter that is between 10-25% larger than a diameter of the distal region of the catheter body.

12. A system as in claim 9, wherein the distal region of the catheter body is 10-25 cm in length.

13. A system as in claim 9, wherein the interventional catheter can achieve an aspiration rate of greater than at least 179% in aspiration rate over a catheter having a length of 115 cm and an internal lumen with a diameter of 0.058 inch, wherein aspiration rate is calculated pursuant to Poiseuille's law for laminar flow in a tube for a fluid having the viscosity of human blood at body temperature.

14. A system as in claim 9, wherein the interventional catheter can achieve an aspiration rate of greater than at least 128% in aspiration rate over a catheter having a length of 105 cm and an internal lumen with a diameter of 0.072 inch, wherein aspiration rate is calculated pursuant to Poiseuille's law for laminar flow in a tube for a fluid having the viscosity of human blood at body temperature.

15. A system as in claim 1, wherein the catheter is telescopically attached to the arterial access sheath such that the catheter can telescopically extend in a distal direction out of a distal end of the arterial access sheath along a longitudinal axis of the arterial access sheath to form a continuous inner lumen between the arterial access sheath and the catheter, wherein the catheter can be telescopically retracted such that the catheter does not extend past the distal end of the arterial access device.

16. A system as in claim 1, wherein the sheath body is 15-30 cm and the catheter is 10 to 15 cm in length.

17. A system as in claim 15, wherein the interventional catheter can achieve an aspiration rate of greater than at least 337% in aspiration rate over a catheter having a length of 115 cm and an internal lumen with a diameter of 0.058 inch, wherein aspiration rate is calculated pursuant to Poiseuille's law for laminar flow in a tube for a fluid having the viscosity of human blood at body temperature.

18. A system as in claim 15, wherein the interventional catheter can achieve an aspiration rate of greater than at least 251% in aspiration rate over a catheter having a length of 105 cm and an internal lumen with a diameter of 0.072 inch, wherein aspiration rate is calculated pursuant to Poiseuille's law for laminar flow in a tube for a fluid having the viscosity of human blood at body temperature.

19. A system as in claim 1, wherein the proximal extension is removably connected to the sheath body.

20. A system as in claim 1, wherein the proximal extension is fixedly connected to the sheath body.

21. A system as in claim 1, wherein the dilator has a distalmost section that is more flexible than a proximalmost section of the dilator.

22. A system as in claim 1, wherein the tether wire includes an internal lumen.

* * * * *